US006673817B1

(12) United States Patent
Zhu et al.

(10) Patent No.: US 6,673,817 B1
(45) Date of Patent: *Jan. 6, 2004

(54) INHIBITORS OF FACTOR XA

(75) Inventors: Bing-Yan Zhu, Belmont, CA (US); Robert M. Scarborough, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/576,635

(22) Filed: May 20, 2000

Related U.S. Application Data

(60) Provisional application No. 60/135,838, filed on May 24, 1999.

(51) Int. Cl.[7] ..................... C07D 207/00; C07D 211/30; C07D 211/32; A61K 31/445
(52) U.S. Cl. ........................................ 514/330; 546/225
(58) Field of Search ................................ 546/189, 225; 514/330

(56) References Cited

U.S. PATENT DOCUMENTS 6,048,900 A * 4/2000 Connell et al. ............. 514/663
6,313,122 B1 * 11/2001 Beight et al. ............ 514/237.5
6,372,759 B1 * 4/2002 Beight et al. ................ 514/318

FOREIGN PATENT DOCUMENTS

| JP | 6-298757 | * 10/1994 |
| WO | WO 98/06694 | 2/1998 |
| WO | WO 98/28269 | 7/1998 |

OTHER PUBLICATIONS

Wallis, R.B., "Inhibitors of Coagulation Factor Xa: From Macromolecular Beginnings to Small Molecules", *Current Opinion in Therapeutic Patents*, Aug. 1, 1993, pp. 1173–1179.

* cited by examiner

*Primary Examiner*—Bruck Kifle
(74) *Attorney, Agent, or Firm*—Townsend and Townsend and Crew LLP

(57) ABSTRACT

Novel compounds, their salts and compositions related thereto having activity against mammalian factor Xa are disclosed. The compounds are useful in vitro or in vivo for preventing or treating coagulation disorders.

20 Claims, No Drawings

INHIBITORS OF FACTOR XA

RELATED APPLICATIONS

This application claims benefit of priority under 35 USC §119(e) to U.S. Provisional Application No. 60/135,838 filed on May 24, 1999, which is herein incorporated in its entirety by reference.

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., Thromb. Res. 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, Haementeria officinalis. A principal component of this saliva was shown to be the polypeptide factor Xa inhibitor, antistasin (ATS), by Nutt, E. et Al, "The Amino Acid Sequence of Antistasin, a Potent Inhibitor of Factor Xa Reveals a Repeated Internal Structure", J. Biol. Chem., M, 10162–10167 (1988). Another potent and highly specific inhibitor of Factor Xa, called tick anticoagulant peptide (TAP), has been isolated from the whole body extract of the soft tick Ornithidoros moubata, as reported by Waxman, L., et al., "Tick Anticoagulant Peptide (TAP) is a Novel Inhibitor of Blood Coagulation Factor Xa" Science, 248, 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naththyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and finctional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In a preferred embodiment, the present invention provides a compound of the formula I:

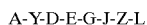

A-Y-D-E-G-J-Z-L wherein:

A is selected from:
(a) $C_1$-$C_6$-alkyl;
(b) $C_3$-$C_8$-cycloalkyl;
(c) phenyl, which is independently substituted with 0–2 $R^1$ subsituents;
(d) naphthyl, which is independently substituted with 0–2 $R^1$ subsituents; and
(e) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ subsituents;

$R^1$ is selected from:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, (CH$_2$)$_m$NR$^2$R$^3$, SO$_2$NR$^2$R$^3$, SO$_2$R$^2$, CF$_3$, OR$^2$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$-$C_4$-alkyl, —CN $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —NO$_2$;

$R^2$ and $R^3$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —NO$_2$;

m is an integer of 0–2;

Y is a member selected from the group consisting of:
a direct link, —C(=O)—, —N(R$^4$)—, —C(=O)—N(R$^4$)—, —N(R$^4$)—C(=O)—, —SO$_2$—, —O—, —SO$_2$—N(R$^4$)— and —N(R$^4$)—SO$_2$—;

$R^4$ is selected from:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —NO$_2$;

D is a direct link or is a member selected from the group consisting of:
(a) phenyl, which is independently substituted with 0–2 $R^{1a}$ subsituents;
(b) naphthyl, which is independently substituted with 0–2 $R^{1a}$ subsituents; and
(c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1a}$ subsituents;

$R^{1a}$ is selected from:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, (CH$_2$)$_m$NR$^{2a}$R$^{3a}$, SO$_2$NR$^{2a}$R$^{3a}$, SO$_2$R$^{2a}$, CF$_3$, OR$^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-4}$alkenyl, $C_{2-6}$alkynyl, $C_{3-8}$cycloalkyl, $C_{0-4}$alkyl$C_{3-8}$cycloalkyl, —CN and —NO$_2$;

$R^{2a}$ and $R^{3a}$ are independently selected from the group consisting of:
H, $C_{1-4}$alkyl, $C_{2-6}$alkenyl, $C_{2-6}$alknyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-4}$alkenyl, $C_{2-6}$alkynyl, $C_{3-8}$cycloalkyl, $C_{0-4}$alkylC3-8cycloalkyl, —CN and —NO$_2$;

E is a member selected from the group consisting of:
—N(R$^5$)—C(=O)—, —C(=O)—N(R$^5$)—, —N(R$^5$)—C(=O)—N(R$^6$)—, —SO$_2$—N(R$^5$)—, —N(R$^5$)—SO$_2$—N(R$^6$)— and —N(R$^5$)—SO$_2$—N(R$^6$)—C(=O)—;

$R^5$ and $R^6$ are independently selected from:
H, $C_{1-4}$alkyl, $C_{2-6}$alkenyl, $C_{2-6}$alynyl, $C_{3-8}$cycloalkyl, C0-4alkyl$C_{3-8}$cycloalkyl, $C_{0-4}$alkylphenyl, $C_{0-4}$alkylnaphthyl, $C_{0-4}$alkytheteroaryl, $C_{1-4}$alkylCOOH and $C_{1-4}$alkylCOOC$_{1-4}$alkyl, wherein from 1–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

G is a member selected from the group consisting of:
a direct link, —CR$^7$R$^8$— and —CR$^{7a}$R$^{8a}$—CR$^{7a}$R$^{8b}$—
wherein R$^7$, R$^8$, R$^{7a}$, R$^{8a}$, R$^{7b}$ and R$^{8b}$ are independently a member selected from from the group consisting of:
hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, —$OR^9$, —$C_{0-4}$alkylCOOR$^9$, —$C_{0-4}$alkylC(=O)NR$^9$R$^{10}$, —$C_{0-4}$alkylC(=O)NR$^9$—CH$_2$—CH$_2$—O—R$^{10}$, —$C_{0-4}$alkylC(=O)NR$^9$(—CH$_2$—CH$_2$—O—R$^{10}$—)$_2$, —N(R$^9$)COR$^{10}$, —N(R$^9$)C(=O)R$^{10}$, —N(R$^9$)SO$_2$R$^{10}$, and a naturally occurring or synthetic amino acid side chain, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —NO$_2$;

R$^9$ and R$^{10}$ are independently selected from:
H, $C_{1-4}$alkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —NO$_2$, and wherein R$^9$ and R$^{10}$ taken together can form a 5–8 membered heterocylic ring;

J is a member selected from the group consisting of:

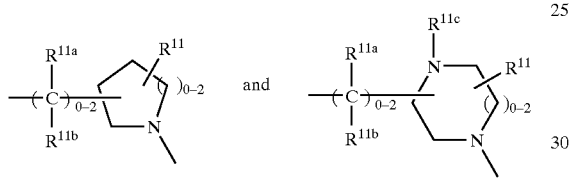

wherein the ring carbons or second ring nitrogen of the amino ring structure and/or the ring carbons on the alkylene bridging groups attached to the amino ring structure may be independently substituted by a total of 0 to 4 R$^{11}$, R$^{11a}$, R$^{11b}$ and R$^{11c}$ groups;

R$^{11}$, R$^{11a}$, R$^{11b}$ and R$^{11c}$ are independently a member selected from the group consisting of:
hydrogen, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, CH$_2$COOC$_{1-4}$alkyl, CH$_2$COOC$_{1-4}$alkylphenyl and CH$_2$COOC$_{1-4}$alkylnaphthyl;

Z is a member selected from the group consisting of:
(a) phenyl, which is independently substituted with 0–2 R$^{1b}$ subsituents;
(b) naphthyl, which is independently substituted with 0–2 R$^{1b}$ subsituents; and
(c) a monocyclic or fused bicyclic heterocyclic ring system having from 5 to 10 ring atoms, wherein 1–4 ring atoms of the ring system are selected from N, O and S, and wherein the ring system may be substituted with 0–2 R$^{1b}$ subsituents;

R$^{1b}$ is selected from:
Halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, —NO$_2$, NR$^{2b}$R$^{3b}$, SO$_2$NR$^{2b}$R$^{3b}$, SO$_2$R$^{2b}$, CF$_3$, OR$^{2b}$, O—CH$_2$—CH$_2$—OR$^{2b}$, O—CH$_2$—COOR$^{2b}$, N(R$^{2b}$)—CH$_2$—CH$_2$—OR$^{2b}$, N(—CH$_2$—CH$_2$—OR$^{2b}$)$_2$, N(R$^{2b}$)—C(=O)R$^{3b}$, N(R$^{2b}$)—SO$_2$—R$^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN and —NO$_2$;

R$^{2b}$ and R$^{3b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN and —NO$_2$;

L is selected from:
H, —CN, C(=O)NR$^{12}$R$^{13}$, (CH$_2$)$_n$NR$^{12}$R$^{13}$, C(=NR$^{12}$)NR$^{12}$R$^{13}$, NR$^{12}$R$^{13}$, OR$^{12}$, —NR$^{12}$C(=NR$^{12}$)NR$^{12}$R$^{13}$, and NR$^{12}$C(=NR$^{12}$)—R$^{13}$;

R$^{12}$ and R$^{13}$ are independently selected from:
hydrogen, —OR$^{14}$, —NR$^{14}$R$^{15}$, $C_{1-4}$alkyl, $C_{0-4}$alkylphenyl, $C_{0-4}$alkylnaphthyl, COOC$_{1-4}$alkyl, COO-$C_{0-4}$alkylphenyl and COO-$C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, and —NO$_2$;

R$^{14}$ and R$^{15}$ are independently selected from:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, and —NO$_2$;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in biological samples such as, for example, stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alknyl") refers to a straight or branched chain aliphatic radical that includes at least two carbons joined by a triple bond. If no number of carbons is specified alkenyl and aikinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2 bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trinethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In a preferred embodiment, the present invention provides a compound according to the formula I:

A-Y-D-E-G-J-Z-L wherein:
A is selected from:
(a) $C_1$–$C_6$-alkyl;
(b) $C_3$–$C_8$-cycloalkyl;
(c) phenyl, which is independently substituted with 0–2 $R^1$ subsituents;
(d) naphthyl, which is independently substituted with 0–2 $R^1$ subsituents; and
(e) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ subsituents;

$R^1$ is selected from:
halo, $C_{1-4}$alkyl, —CN, $(CH_2)_m NR^2 R^3$, $SO_2 NR^2 R^3$, $SO_2 R^2$, $CF_3$, $OR^2$, and a 5–6 membered aromatic heterocyclic system containing from 1–4 heteroatoms selected from N, O and S;

$R^2$ and $R^3$ are independently selected from the group consisting of: H, $C_{1-4}$alkyl and $C_{0-4}$alkylaryl, m is an integer of 0–2;

Y is a member selected from the group consisting of: a direct link, —C(=O)—, —N($R^4$)—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from:
H, $C_{1-4}$alkyl and $C_{0-4}$alkylaryl;.

D is absent or is a member selected from the group consisting of:
(a) aryl, which is independently substituted with 0–2 $R^{1a}$ subsituents; and (b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1a}$ subsituents;

$R^{1a}$ is selected from:
Halo, $C_{1-4}$alkyl, —CN, —NO$_2$, $(CH_2)_m NR^{2a}R^{3a}$, $SO_2NR^{2a}R^{3a}$, $SO_2R^{2a}$, $CF_3$, $OR^{2a}$, and a 5–6 membered aromatic heterocyclic ring containing from 1–4 heteroatoms selected from N, O and S;

$R^{2a}$ and $R^{3a}$ are independently selected from the group consisting of:
H, $C_{1-4}$alkyl and $C_{0-4}$alkylaryl;

E is a member selected from the group consisting of:
—N($R^5$)—C(=O)—, —C(=O)—N($R^5$)—, —N($R^5$)—C(=O)—N($R^6$)—, —SO$_2$—N($R^5$)—, —N($R^5$)—SO$_2$—N($R^6$)— and —N($R^5$)—SO$_2$—N($R^6$)—C(=O)—;

$R^5$ and $R^6$ are independently selected from:
H, $C_{1-4}$alkyl, $C_{0-4}$alkylaryl, $C_{0-4}$alkylheteroaryl, $C_{1-4}$alkylCOOH and $C_{1-4}$alkylCOOC$_{1-4}$alkyl;

G is a member selected from the group consisting of:
a direct link, —CR$^7$R$^8$— and —CR$^{7a}$R$^{8a}$—CR$^{7a}$R$^{8b}$— wherein $R^7$, $R^8$, $R^{7a}$, $R^{8a}$, $R^{7b}$ and $R^{8b}$ are independently a member selected from from the group consisting of:
hydrogen, $C_{1-4}$alkyl, $C_{0-4}$alkyl-$C_{3-8}$cycloalkyl, $C_{0-4}$alkylaryl, —OR$^9$, —C$_{0-4}$alkylCOOR$^9$, —C$_{0-4}$alkylC(=O)NR$^9$R$^{10}$, —N(R$^9$)COR$^{10}$, —N(R$^9$)C(=O)R$^{10}$, —N(R$^9$)SO$_2$R$^{10}$, and common amino acid side chains;

$R^9$ and $R^{10}$ are independently selected from:
H, $C_{1-4}$alkyl and $C_{0-4}$alkylaryl;

J is a member selected from the group consisting of:

and wherein the ring carbons or the second ring nitrogen of the amino ring structure and/or the ring carbons on the alkylene bridging groups attached to the amino ring structure may be independently substituted by a total of 0 to 4 $R^{11}$, $R^{11a}$, $R^{11b}$ and $R^{11c}$ groups;

$R^{11}$, $R^{11a}$, $R^{11b}$ and $R^{11c}$ are independently a member selected from the group consisting of:
hydrogen, —OH, —O—C$_{1-4}$alkyl, —C$_{1-4}$alkyl, C$_{2-6}$alkenyl, C$_{2-6}$alkynyl, C$_{3-8}$cycloalkyl, C$_{0-4}$alkyl-C$_{3-8}$cycloalkyl, C$_{0-4}$alkylphenyl, C$_{0-4}$alkylnaphthyl, C$_{0-4}$alkylheterocyclic ring having from 1 to 4 hetero ring atoms selected from the group consisting of N, O and S, CH$_2$COOC$_{1-4}$alkyl, CH$_2$COOC$_{1-4}$alkylphenyl and CH$_2$COOC$_{1-4}$alkylnaphthyl;

Z is a member selected from the group consisting of:
(a) aryl, which is independently substituted with 0–2 $R^{1b}$ subsituents;and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1b}$ subsituents;

$R^{1b}$ is selected from:
halo, $C_{1-4}$alkyl, —CN, —NO$_2$, NR$^{2b}$R$^{3b}$, SO$_2$NR$^{2b}$R$^{3b}$, SO$_2$R$^{2b}$, CF$_3$, OR$^{2b}$, O—CH$_2$—CH$_2$—OR$^{2b}$, O—CH$_2$—COOR$^{2b}$, N(R$^{2b}$)—CH$_2$—CH$_2$—OR$^{2b}$, N(—CH$_2$—CH$_2$—OR$^{2b}$)$_2$, N(R$^{2b}$)—C(=O)R$^{3b}$, N(R$^{2b}$)—SO$_2$—R$^{3b}$, and a 5–6 membered aromatic heterocyclic ring containing from 1–4 heteroatoms selected from N, O and S;

$R^{2b}$ and $R^{3b}$ are independently selected from the group consisting of:
H, $C_{1-4}$alkyl and $C_{0-4}$alkylaryl;

L is selected from:
H, —CN, C(=O)NR$^{12}$R$^{13}$, (CH$_2$)$_n$NR$^{12}$R$^{13}$, C(=NR$^{12}$)NR$^{12}$R$^{13}$, NR$^{12}$R$^{13}$, OR$^{12}$, —NR$^{12}$C(=NR$^{12}$)NR$^{12}$R$^{13}$ and NR$^{12}$C(=NR$^{12}$)—R$^{13}$;

$R^{12}$ and $R^{13}$ are independently selected from:
hydrogen, —OR$^{14}$, —NR$^{14}$R$^{15}$, C$_{1-4}$alkyl, C$_{0-4}$alkylaryl COOC$_{1-4}$alkyl, and COO—C$_{0-4}$ alkylaryl;

$R^{14}$ and $R^{15}$ are independently selected from:
H and $C_{1-4}$alkyl; and and all pharmaceutically acceptable isomers, salts, hydrates, solvates and prodrug derivatives thereof.

In a further preferred embodiment, the present invention provides a compound according to the formula I:

A-Y-D-E-G-J-Z-L wherein:

A is selected from:
(a) phenyl, which is independently substituted with 0–2 $R^1$ subsituents; and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ subsituents;

$R^1$ is selected from:
halo, $(CH_2)_m NR^2R^3$, SO$_2$NR$^2$R$^3$ and SO$_2$R$^2$;

$R^2$ and $R^3$ are independently selected from the group consisting of:
H and $C_{1-4}$alkyl;

Y is a member selected from the group consisting of:
a direct link, —C(=O)—, —SO$_2$— and —O—;

D is a member selected from the group consisting of:
(a) phenyl, which is independently substituted with 0–2 $R^{1a}$ subsituents; and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1a}$ subsituents;

$R^{1a}$ is selected from:
Halo and $C_{1-4}$alkyl;

$R^{2a}$ and $R^{3a}$ are independently selected from the group consisting of:
H, $C_{1-4}$alkyl, $C_{0-4}$alkylaryl;

E is a member selected from the group consisting of:
—N($R^5$)—C(=O)— and —C(=O)—N($R^5$)—;

$R^5$ and $R^6$ are independently selected from:
H, $C_{1-4}$alkyl, $C_{0-4}$alkylaryl and $C_{0-4}$alkylheteroaryl;

G is a member selected from the group consisting of:
a direct link, —CR$^7$R$^8$— and —CR$^{7a}$R$^{8a}$—CR$^{7a}$R$^{8b}$— wherein $R^7$, $R^8$, $R^{7a}$, $R^{8a}$, $R^{7b}$ and $R^{8b}$ are independently a member selected from from the group consisting of:

hydrogen, $C_{1-4}$alkyl, $C_{0-4}$alkyl-$C_{3-8}$cycloalkyl, $C_{0-4}$alkylaryl, —$OR^9$, —$C_{0-4}$alkyl$COOR^9$, —$CO_{0-4}$alkylC(=O) $NR^9R^{10}$, —$C_{0-4}$alkylC(=O)$NR^9$(—$CH_2$—$CH_2$—O—$R^{10}$, —$C_{0-4}$alkylC(=O)$NR^9$(—$CH_2$—$CH_2$—O—$R^{10}$—$)_2$, —$N(R^9)COR^{10}$, —$N(R^9)C(=O)R^{10}$, —$N(R^9)SO_2R^{10}$, and common amino acid side chains;

$R^9$ and $R^{10}$ are independently selected from:
H and $C_{1-4}$alkyl, wherein the $NR^9R^{10}$ group of $R^7$, $R^8$, $R^{7a}$, $R^{8a}$, $R^{7b}$ and $R^{8b}$ is optionally cyclized to form a 5–8 membered heterocyclic group;

J is a member selected from the group consisting of:

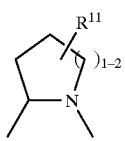 and 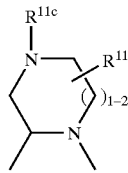

wherein the ring carbons or the second ring nitrogen of the amino ring structure may be substituted by a total of 0 to 2 $R^{11}$ and $R^{11c}$ groups;

$R^{11}$, $R^{11a}$, $R^{11b}$ and $R^{11c}$ are independently a member selected from the group consisting of:
hydrogen, —OH, —O—$C_{1-4}$alkyl, —$C_{1-4}$alkyl, $C_{2-6}$alkenyl, $C_{0-4}$alkylaryl, and a $C_{0-4}$alkylheterocyclic ring having from 1 to 4 hetero ring atoms selected from the group consisting of N, O and S;

Z is a member selected from the group consisting of:
(a) phenyl, which is independently substituted with 0–2 $R^{1b}$ subsituents;
(b) an aromatic heterocyclic ring having from 5 to 10 ring atoms, wherein 1–4 ring atoms are selected from N, O and S, and wherein the ring may be subsituted independently by from 0–2 $R^{1b}$ subsituents; and
(c) a fused aromatic bicyclic heterocyclic ring system having from 5 to 10 ring atoms, wherein 1–4 ring atoms of the ring system are selected from N, O and S, wherein the bicyclic ring system may be substituted with 0–2 $R^{1b}$ subsituents;

$R^{1b}$ is selected from:
halo, $C_{1-4}$alkyl, OH, OBn, O—$CH_2$—$CH_2$—OH, O—$CH_2$—$CH_2$—$OCH_3$, O—$CH_2$—COOH, O—$CH_2$—C(=O)—O—$CH_3$, $NH_2$, NH—$CH_2$—$CH_2$—O—$CH_3$, NH—C(=O)—O—$CH_3$, and NH—$SO_2$—$CH_3$;

L is selected from:
H, C(=O)$NR^{12}R^{13}$, $(CH_2)_nNR^{12}R^{13}$ and C(=$NR^{12}$)$NR^{12}R^{13}$;

$R^{12}$ and $R^{13}$ are independently selected from:
hydrogen and $C_{1-4}$alkyl;

and all pharmaceutically acceptable isomers, salts, hydrates, solvates and prodrug derivatives thereof.

In a further preferred embodiment, the present invention provides a compound according to formula I:

A-D-E-G-J-Z-L wherein

A is a member selected from the group consisting of:

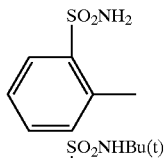
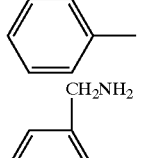
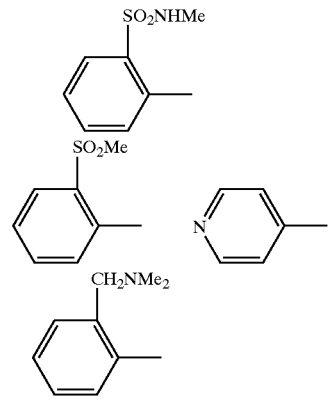

D is a member selected from the group consisting of:

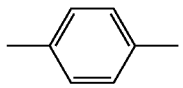 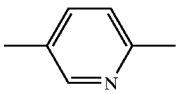
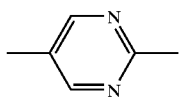 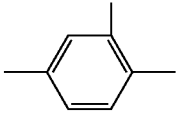
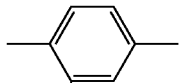 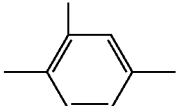
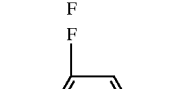 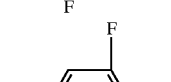
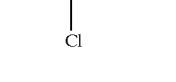 

E is a member selected from the group consisting of:
—C(=O)—NH—, —C(=O)—N(—$CH_3$)—, C(=O)—N(—Bn)—, —NH—C(=O)—, —N(—$CH_3$)—C(=O)— and —N(—Bn)C(=O)—;

G is a member selected from the group consisting of:
a direct link, —CH—(—$NH_2$)—$CH_2$—, —CH—(—NH(C(=O)—$CH_3$))—$CH_2$—, —CH—(—NH(C(=O)—Ph))—$CH_2$—, —CH—(C(=O)—$OR^8$)—, —CH(—$R^7$)—, —$CH_2$—CH(C(=O)—$OR^8$)—, and —$CH_2$—CH(C(=O)—N(—$R^8$, —$R^8$))—;

$R^7$ is a member selected from the group consisting of:
H, phenyl, Bn, —O-loweralkyl and cycohexyl;

$R^8$ is a member selected from the group consisting of:
H, $C_{1-6}$alkyl, —O-loweralkyl and $C_{3-6}$cycloalkyl;

J is a member selected from the group consisting of:

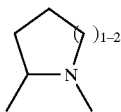 and 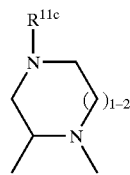

wherein the second ring nitrogen of the amino ring structure may be substituted by a $R^{11c}$ group;

$R^{11c}$ is a member selected from the group consisting of: H, methyl, phenyl and benzyl; and Z and L taken together are a member selected from the group consisting of:

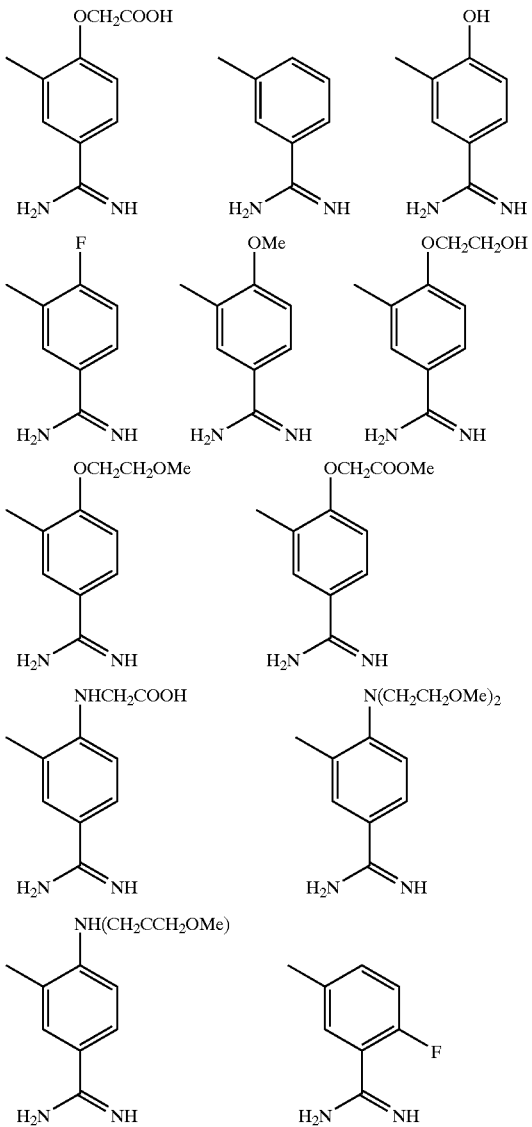

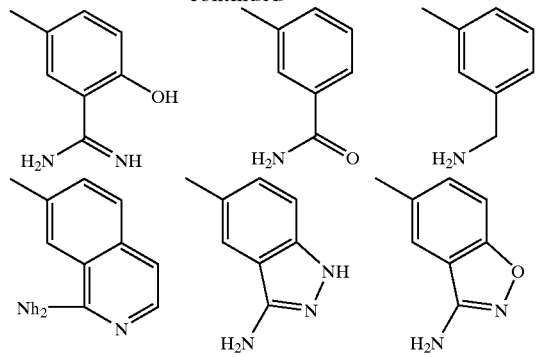

and all pharmaceutically acceptable isomers, salts, hydrates, solvates and prodrug derivatives thereof.

The following non-limiting tables illustrate representative compounds of the present invention:

TABLE 1

Formula II

| $R^{11'}$ | $R^{11''}$ | $R^{1b'}$ | $R^{1b''}$ |
|---|---|---|---|
| H | H | H | H |
| Me | Me | H | OH |

TABLE 1-continued

Formula II

| R[11'] | R[11''] | R[1b'] | R[1b''] |
|---|---|---|---|
| (phenyl-CH3) | (phenyl) | F | H |
| (4-hydroxyphenyl-CH3) | (phenyl-CH2) | —OH | F |

TABLE 1a

Formula IIa

| R[11'] | R[11''] | R[1b'] | R[1b''] |
|---|---|---|---|
| H | H | H | H |
| Me | Me | H | OH |
|  |  | F | H |
| (phenyl-CH3) | (phenyl) |  |  |
| (4-hydroxyphenyl-CH3) | (phenyl-CH2) | —OH | F |

TABLE 1b

Formula IIb

| R[11'] | R[11''] | R[1b'] | R[1b''] |
|---|---|---|---|
| H | H | H | H |
| Me | Me | H | OH |
|  |  | F | H |
| (phenyl-CH3) | (phenyl) |  |  |
|  |  | —OH | F |
| (4-hydroxyphenyl-CH3) | (phenyl-CH2) |  |  |

TABLE 1c

Formula IIc

| R[11] | R[11c] | R[1b'] | R[1b''] |
|---|---|---|---|
| H | H | H | H |
| Me | Me | H | OH |
| (phenyl-CH3) | Me | F | H |

TABLE 1c-continued

Formula IIc

| $R^{11}$ | $R^{11c}$ | $R^{1b'}$ | $R^{1b''}$ |
|---|---|---|---|
| Me | 4-hydroxyphenyl | —OH | F |

TABLE 1d

Formula IId

| $R^{11'}$ | $R^{11''}$ | $R^{1b'}$ | $R^{1b''}$ |
|---|---|---|---|
| H | H | H | H |
| Me | Me | H | OH |
| phenyl | Me | F | H |
| Me | 4-hydroxyphenyl | —OH | F |

TABLE 1e

Formula IIe

| $R^{11}$ | $R^{11c}$ | $R^{1b'}$ | $R^{1b''}$ |
|---|---|---|---|
| H | H | H | H |
| Me | Me | H | OH |
| phenyl | phenyl | F | H |
| 4-hydroxyphenyl | benzyl | —OH | F |

TABLE 2

Formula III

| $R^{11'}$ | $R^{11''}$ | $R^{1b}$ |
|---|---|---|
| H | H | H |
| Me | Me | H |
| phenyl | phenyl | F |
| 4-hydroxyphenyl | benzyl | —OH |

TABLE 2a
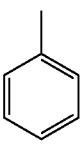
Formula IIIa
| $R^{11'}$ | $R^{11''}$ | $R^{1b}$ |
|---|---|---|
| H | H | H |
| Me | Me | H |
| 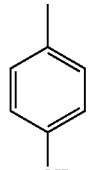 | Me | F |
| Me | 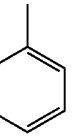 | —OH |
TABLE 2b
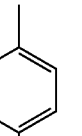
Formula IIIb
| $R^{11'}$ | $R^{11''}$ | $R^{1b}$ |
|---|---|---|
| H | H | H |
| Me | Me | H |
| 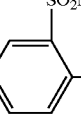 |  | F |
| 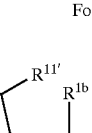 | 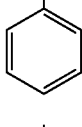 | —OH |
TABLE 2c
Formula IIIc
| $R^{11'}$ | $R^{11c}$ | $R^{1b}$ |
|---|---|---|
| H | H | H |
| Me | Me | H |
|  | Me | F |
| 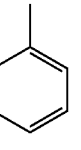 |  |  |
| Me |  | —OH |
|  | (phenol) |  |
TABLE 2d
Formula IIId
| $R^{11'}$ | $R^{11''}$ | $R^{1b}$ |
|---|---|---|
| H | H | H |
| Me | Me | H |
|  | Me | F |

TABLE 2d-continued

Formula IIId

| R$^{11'}$ | R$^{11''}$ | R$^{1b}$ |
|---|---|---|
| Me | *p-hydroxyphenyl* | —OH |

TABLE 2e

Formula IIIe

| R$^{11'}$ | R$^{11c}$ | R$^{1b}$ |
|---|---|---|
| H | H | H |
| Me | Me | H |
| *o-tolyl* | *phenyl* | F |
| *p-hydroxyphenyl* | *benzyl* | —OH |

TABLE 3

Formula IV

| R$^{11'}$ | R$^{11''}$ | R$^{1b}$ |
|---|---|---|
| H | H | H |
| Me | Me | H |
| *p-tolyl* | *phenyl* | F |
| *p-hydroxyphenyl* | *benzyl* | —OH |

TABLE 3a

Formula IVa

| R$^{11'}$ | R$^{11''}$ | R$^{1b}$ |
|---|---|---|
| H | H | H |
| Me | Me | H |
| *p-tolyl* | *phenyl* | F |
| *p-hydroxyphenyl* | *benzyl* | —OH |

TABLE 3b
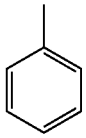
Formula IVb
| R<sup>11'</sup> | R<sup>11"</sup> | R<sup>1b</sup> |
|---|---|---|
| H | H | H |
| Me | Me | H |
|  | 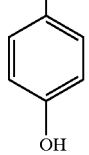 | F |
| 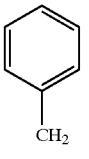 |  | —OH |
TABLE 3c
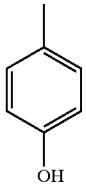
Formula IVc
| R<sup>11'</sup> | R<sup>11c</sup> | R<sup>1b</sup> |
|---|---|---|
| H | H | H |
| Me | Me | H |
| 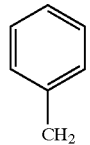 |  | F |
TABLE 3c-continued
Formula IVc
| R<sup>11'</sup> | R<sup>11c</sup> | R<sup>1b</sup> |
|---|---|---|
| 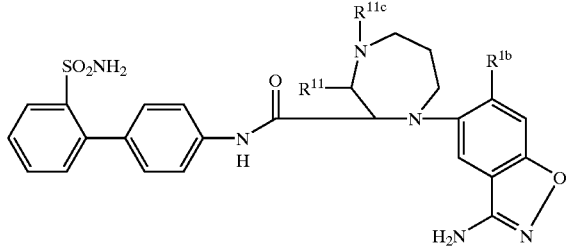 | 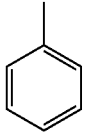 | —OH |
TABLE 3d
Formula IVd
| R<sup>11'</sup> | R<sup>11c</sup> | R<sup>1b</sup> |
|---|---|---|
| H | H | H |
| Me | Me | H |
| 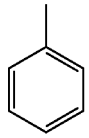 | 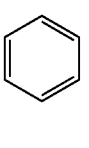 | F |
|  | 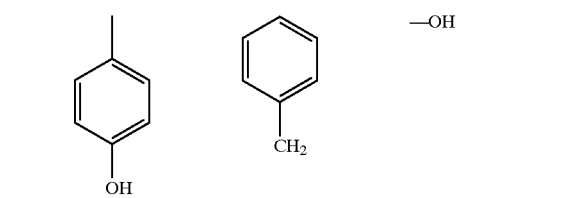 | —OH |

TABLE 3e
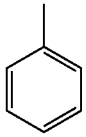
Formula IVe
| R11' | R11'' | R1b |
|---|---|---|
| H | H | H |
| Me | Me | H |
|  | 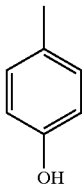 | F |
| 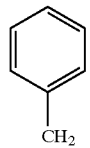 | 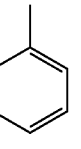 | —OH |
TABLE 4
Formula V
| R11' | R11'' | R1b |
|---|---|---|
| H | H | H |
| Me | Me | H |
| 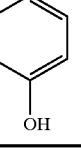 | 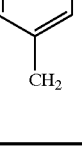 | F |
| 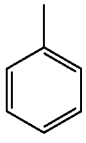 | 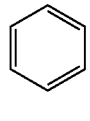 | —OH |
TABLE 4a
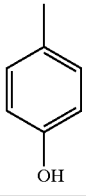
Formula Va
| R11' | R11'' | R1b |
|---|---|---|
| H | H | H |
| Me | Me | H |
| 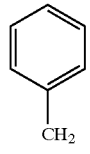 | 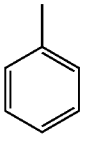 | F |
|  | 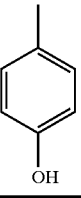 | —OH |
TABLE 4b
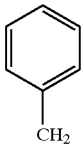
Formula Vb
| R11' | R11'' | R1b |
|---|---|---|
| H | H | H |
| Me | Me | H |
| | | F |
| | | —OH |

TABLE 4c
Formula Vc
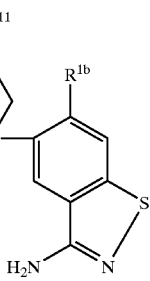
| R[11] | R[11c] | R[1b] |
|---|---|---|
| H | H | H |
| Me | Me | H |
| 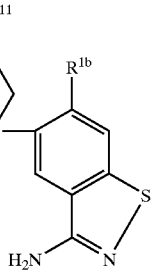 | 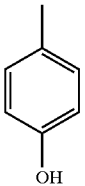 | F |
TABLE 4c-continued
Formula Vc
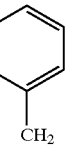
| R[11] | R[11c] | R[1b] |
|---|---|---|
| 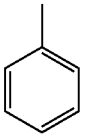 |  | —OH |
TABLE 4d
Formula Vd
| R[11] | R[11c] | R[1b] |
|---|---|---|
| H | H | H |
| Me | Me | H |
| 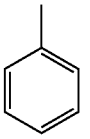 |  | F |
| 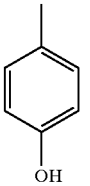 | 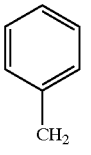 | —OH |

TABLE 4e
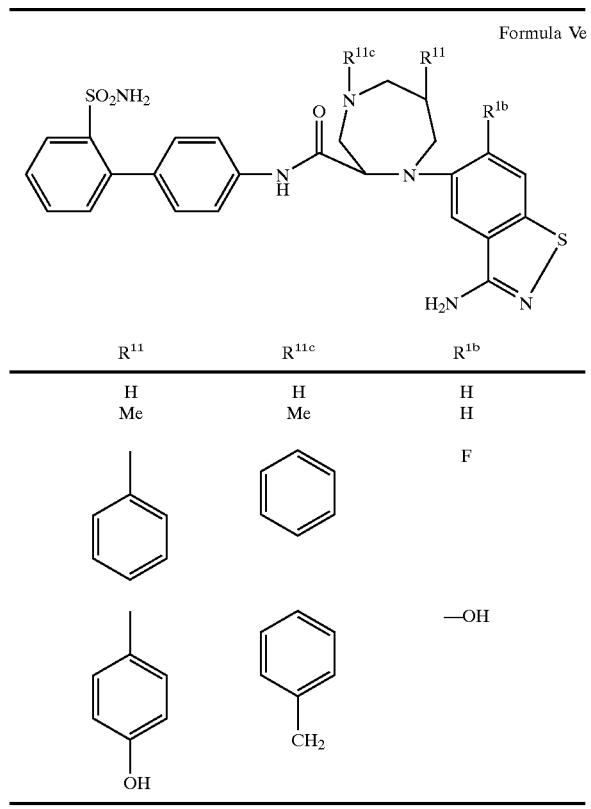
| R[11] | R[11c] | R[1b] |
|---|---|---|
| H | H | H |
| Me | Me | H |
| (phenyl) | (phenyl) | F |
| (4-hydroxyphenyl) | (benzyl) | —OH |
TABLE 5
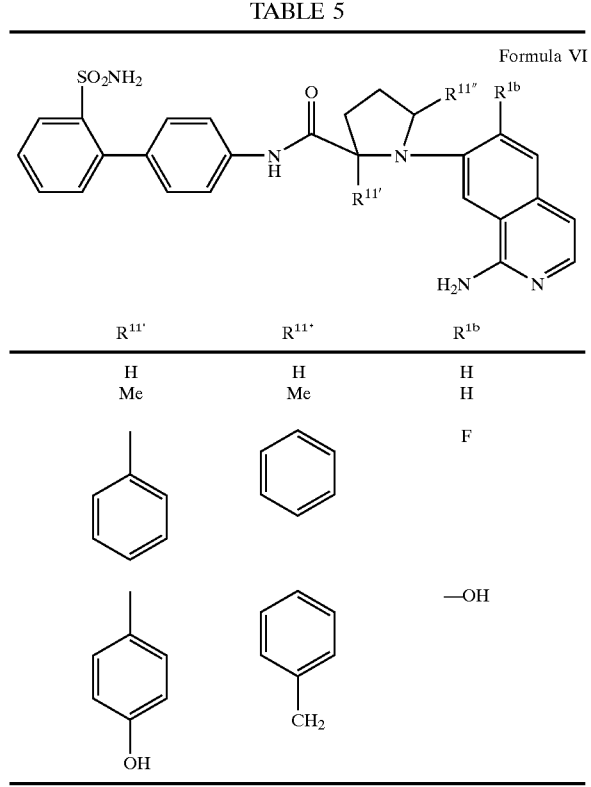
Formula VI
| R[11'] | R[11*] | R[1b] |
|---|---|---|
| H | H | H |
| Me | Me | H |
| (phenyl) | (phenyl) | F |
| (4-hydroxyphenyl) | (benzyl) | —OH |
TABLE 5a
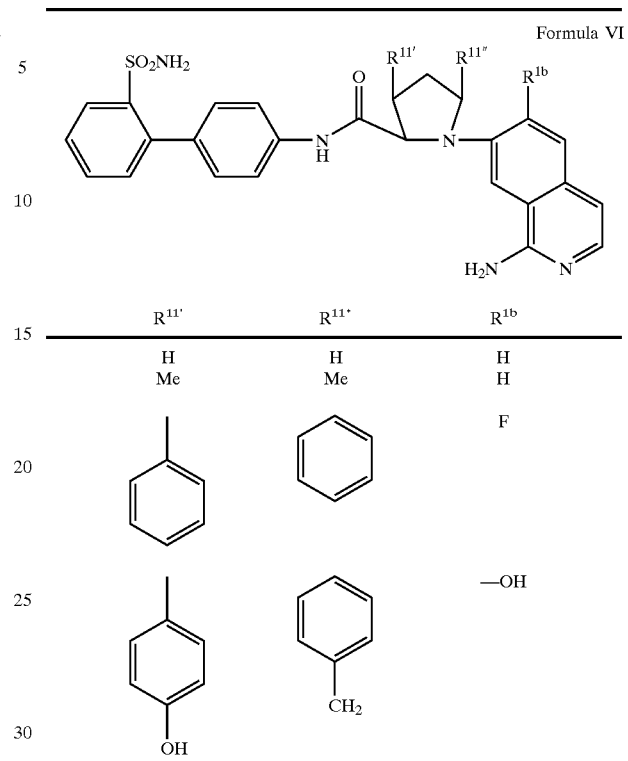
Formula VI
| R[11'] | R[11″] | R[1b] |
|---|---|---|
| H | H | H |
| Me | Me | H |
| (phenyl) | (phenyl) | F |
| (4-hydroxyphenyl) | (benzyl) | —OH |
TABLE 5b
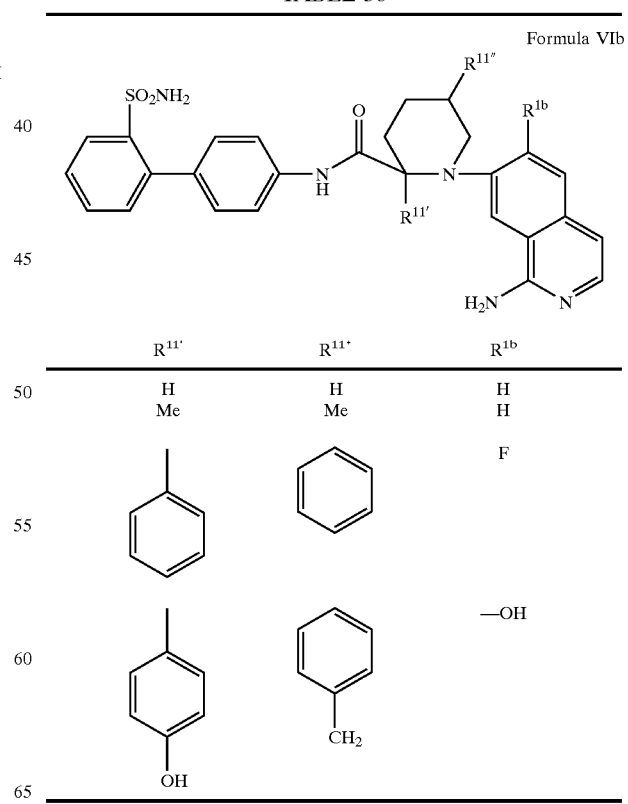
Formula VIb
| R[11'] | R[11*] | R[1b] |
|---|---|---|
| H | H | H |
| Me | Me | H |
| (phenyl) | (phenyl) | F |
| (4-hydroxyphenyl) | (benzyl) | —OH |

TABLE 5c
Formula VIc
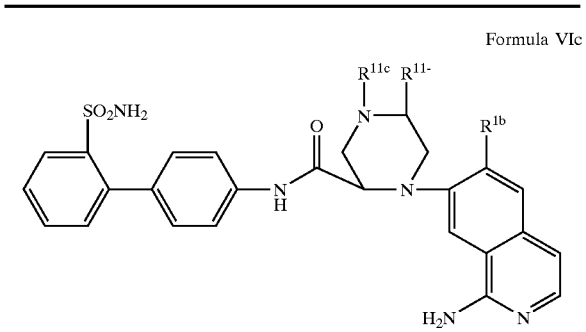
| $R^{11}$ | $R^{11c}$ | $R^{1b}$ |
|---|---|---|
| H | H | H |
| Me | Me | H |
| (phenyl) | (phenyl) | F |
TABLE 5c-continued
Formula VIc
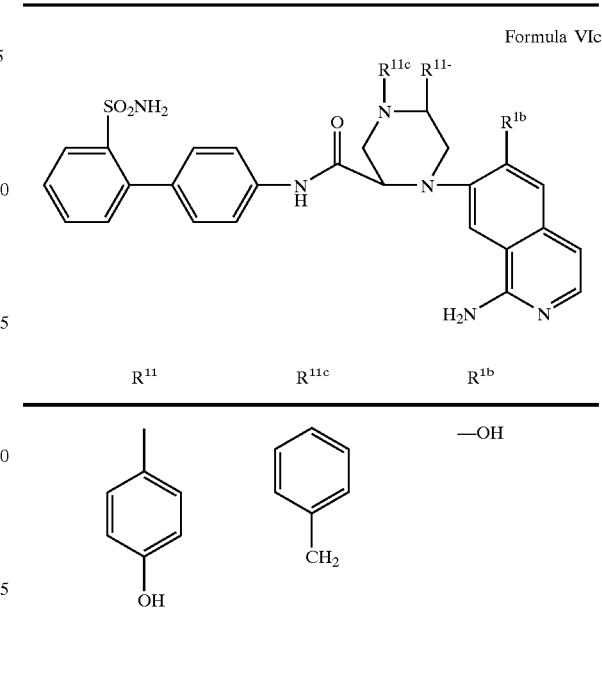
| $R^{11}$ | $R^{11c}$ | $R^{1b}$ |
|---|---|---|
| 4-hydroxyphenyl | benzyl | —OH |
TABLE 5d
Formula VId
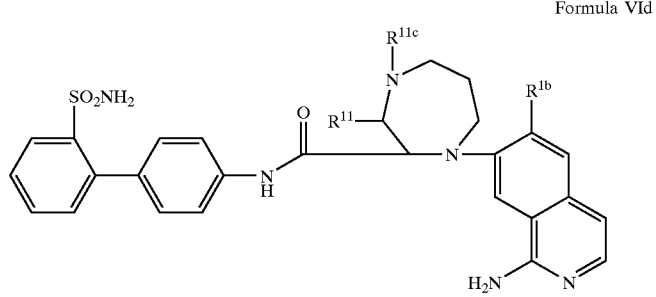
| $R^{11}$ | $R^{11c}$ | $R^{1b}$ |
|---|---|---|
| H | H | H |
| Me | Me | H |
| (phenyl) | (phenyl) | F |
| 4-hydroxyphenyl | benzyl | —OH |

TABLE 5e

Formula VIe

| R11 | R11c | R1b |
|---|---|---|
| H | H | H |
| Me | Me | H |
| phenyl | phenyl | F |
| 4-hydroxyphenyl | benzyl | —OH |

TABLE 6

Formula VII

| R11' | R11'' | R1b |
|---|---|---|
| H | H | H |
| Me | Me | H |
| phenyl | phenyl | F |
| 4-hydroxyphenyl | benzyl | —OH |

TABLE 6a

Formula VIIa

| R11' | R11'' | R1b |
|---|---|---|
| H | H | H |
| Me | Me | H |
| phenyl | phenyl | F |
| 4-hydroxyphenyl | benzyl | —OH |

TABLE 6b

Formula VIIb

| R11' | R11'' | R1b |
|---|---|---|
| H | H | H |
| Me | Me | H |
| phenyl | phenyl | F |
| 4-hydroxyphenyl | benzyl | —OH |

TABLE 6c

Formula VIIc: 2-(sulfamoyl)biphenyl-4'-yl-NH-C(=O)-[piperazine with R11, R11c substituents]-N-isoquinolin-7-yl(R1b)

| R11 | R11c | R1b |
|---|---|---|
| H | H | H |
| Me | Me | H |
| 3-methylphenyl | phenyl | F |
| 4-hydroxyphenyl | benzyl (CH2-phenyl) | —OH |

TABLE 6d

Formula VIId: 2-(sulfamoyl)biphenyl-4'-yl-NH-C(=O)-[diazepane with R11, R11c substituents]-N-isoquinolin-7-yl(R1b)

| R11 | R11c | R1b |
|---|---|---|
| H | H | H |
| Me | Me | H |
| 3-methylphenyl | phenyl | F |

TABLE 6d-continued

Formula VIId

| R11 | R11c | R1b |
|---|---|---|
| 4-hydroxyphenyl | benzyl (CH2-phenyl) | —OH |

TABLE 6e

Formula VIIe: 2-(sulfamoyl)biphenyl-4'-yl-NH-C(=O)-[diazepane with R11, R11c substituents]-N-isoquinolin-7-yl(R1b)

| R11 | R11c | R1b |
|---|---|---|
| H | H | H |
| Me | Me | H |
| 3-methylphenyl | phenyl | F |
| 4-hydroxyphenyl | benzyl (CH2-phenyl) | —OH |

TABLE 7
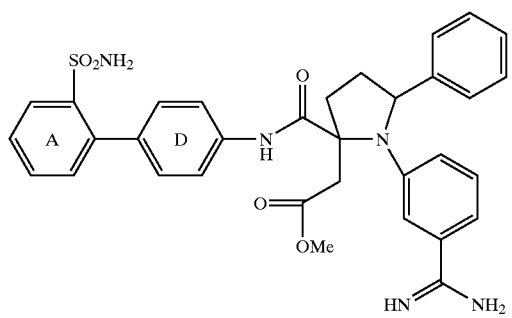
Formula VIII
| A | D | A | D |
|---|---|---|---|
| 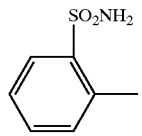 | 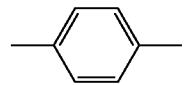 | 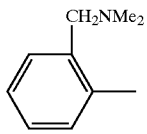 | 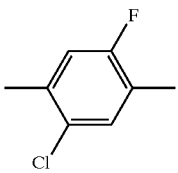 |
| 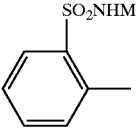 | 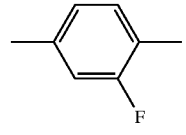 | 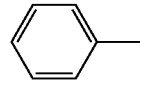 | 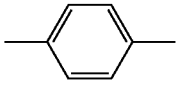 |
| 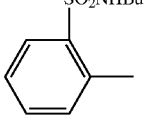 | 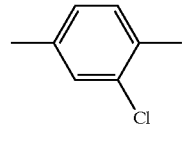 | 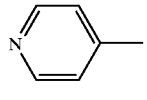 |  |
| 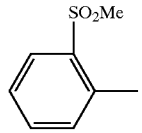 | 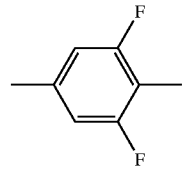 | 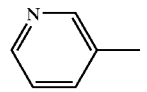 | 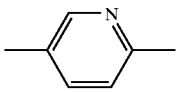 |
| 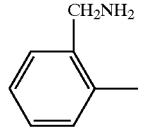 | 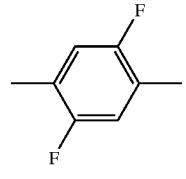 | 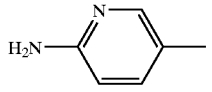 | 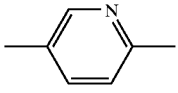 |
| 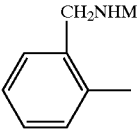 | 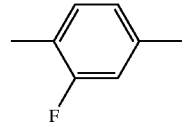 | 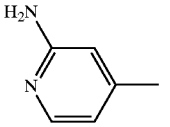 | 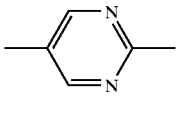 |

TABLE 7a
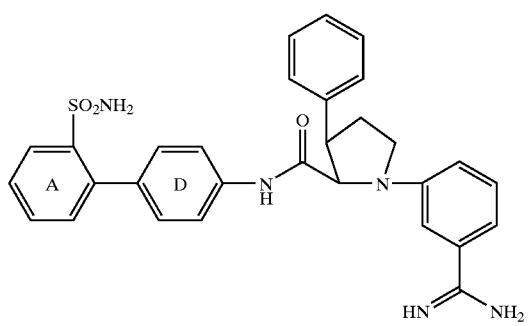
Formula VIIIa
| A | D | A | D |
|---|---|---|---|
| 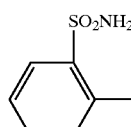 | 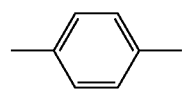 | 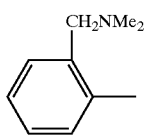 | 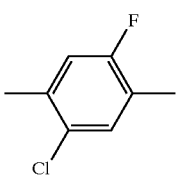 |
| 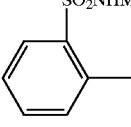 | 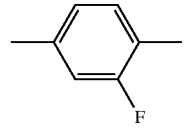 | 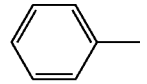 |  |
| 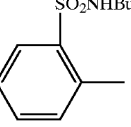 | 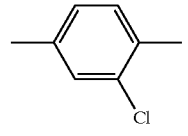 | 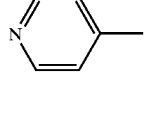 |  |
| 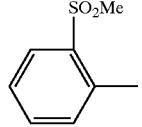 | 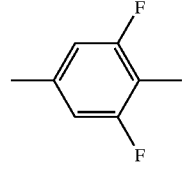 | 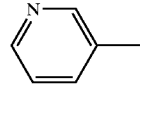 | 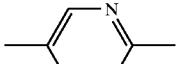 |
| 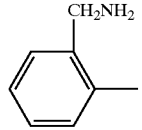 | 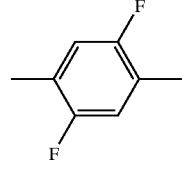 | 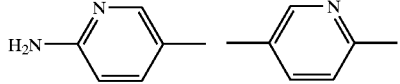 | 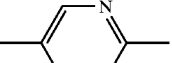 |
| 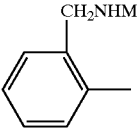 | 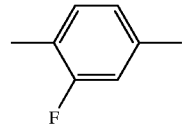 | 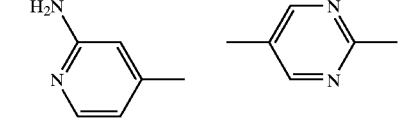 | 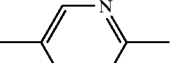 |

TABLE 7c
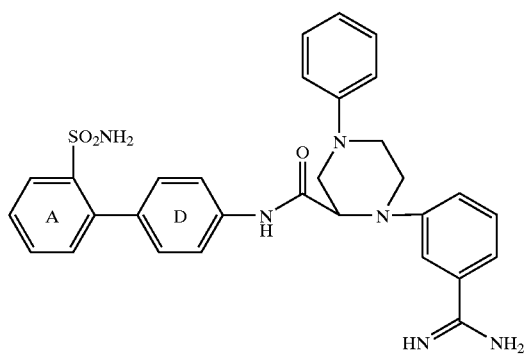
Formula VIIIc
| A | D | A | D |
|---|---|---|---|
| 2-Me-C6H4-SO2NH2 | 1,4-C6H4 | 2-Me-C6H4-CH2NMe2 | 5-F-2-Cl-C6H3 (1,4) |
| 2-Me-C6H4-SO2NHMe | 3-F-C6H3 (1,4) | C6H5 | 1,4-C6H4 |
| 2-Me-C6H4-SO2NHBu(t) | 3-Cl-C6H3 (1,4) | 4-pyridyl | 1,4-C6H4 |
| 2-Me-C6H4-SO2Me | 2,3-diF-C6H2 (1,4) | 3-pyridyl | 2,5-pyridyl |
| 2-Me-C6H4-CH2NH2 | 2,5-diF-C6H2 (1,4) | 2-amino-5-pyridyl | 2,5-pyridyl |
| 2-Me-C6H4-CH2NHMe | 3-F-C6H3 (1,4) | 2-amino-4-pyridyl | 2,5-pyrimidyl |

TABLE 7c
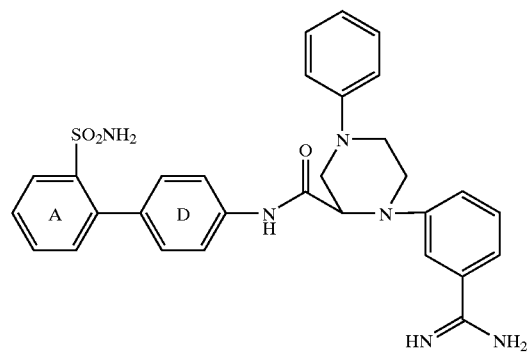

TABLE 7d

Formula VIIId

| A | D | A | D |
|---|---|---|---|
| 2-Me-C6H4-SO2NH2 | 1,4-C6H4 | 2-Me-C6H4-CH2NMe2 | 5-F-2-Cl-C6H3 |
| 2-Me-C6H4-SO2NHMe | 3-F-C6H3 | C6H5 | 1,4-C6H4 |
| 2-Me-C6H4-SO2NHBu(t) | 3-Cl-C6H3 | 4-pyridyl | 1,4-C6H4 |
| 2-Me-C6H4-SO2Me | 3,5-diF-C6H2 | 3-pyridyl | 2,5-pyridyl |
| 2-Me-C6H4-CH2NH2 | 2,5-diF-C6H2 | 2-amino-5-pyridyl | 2,5-pyridyl |
| 2-Me-C6H4-CH2NHMe | 3-F-C6H3 | 2-amino-4-pyridyl | 2,5-pyrimidinyl |

TABLE 7e
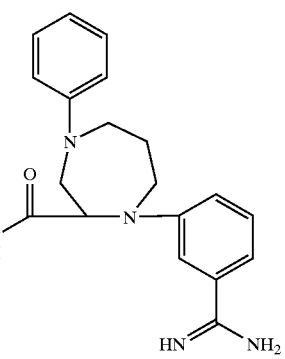

TABLE 8
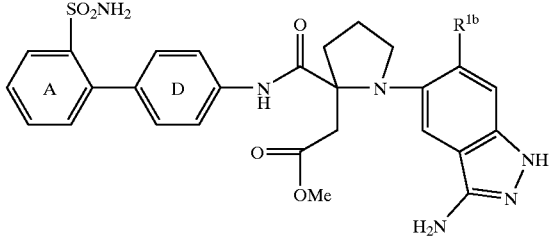
Formula IX
| A | D | A | D |
|---|---|---|---|
| 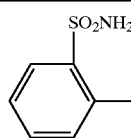 | 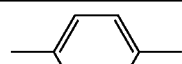 | 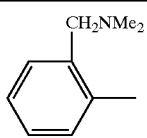 | 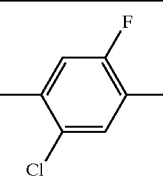 |
| 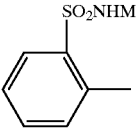 | 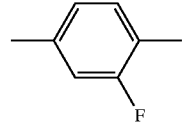 | 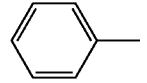 |  |
| 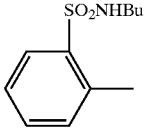 | 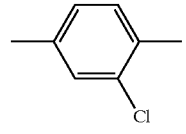 | 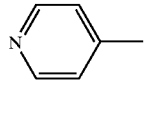 | 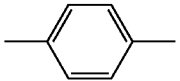 |
| 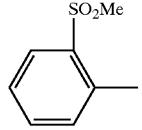 | 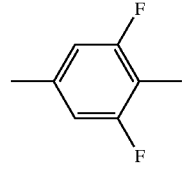 | 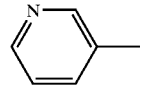 | 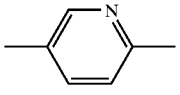 |
| 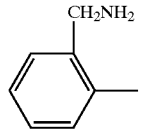 | 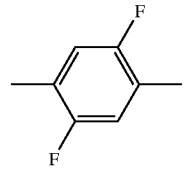 | 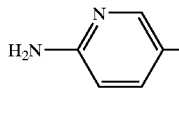 | 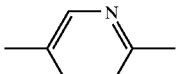 |
| 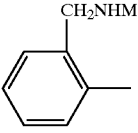 | 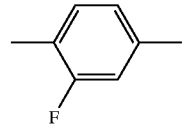 | 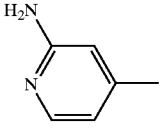 | 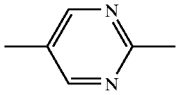 |
wherein $R^{1b}$ is a member selected from the group consisting of H, F, —OH, Br, Cl, —$NH_2$, —O—$CH_2$—O—Ph and —O—$CH_2$—$CH_2$—O—$CH_3$, TABLE 8a Formula IXa wherein $R^{1b}$ is a member selected from the group consisting of H, F, —OH, Br, Cl, —NH$_2$, —O—CH$_2$—O—Ph and —O—CH$_2$—CH$_2$—O—CH$_3$, TABLE 8b Formula IXb

[Structure of Formula IXb showing biphenyl group A-D connected via amide to piperidine bearing methyl ester and 3-amino-1H-indazole with R^{1b} substituent]

| A | D | A | D |
|---|---|---|---|
| 2-methylphenyl with SO$_2$NH$_2$ | 1,4-phenylene | 2-methylphenyl with CH$_2$NMe$_2$ | 2-fluoro-5-chloro-1,4-phenylene |
| 2-methylphenyl with SO$_2$NHMe | 3-fluoro-1,4-phenylene | phenyl | 1,4-phenylene |
| 2-methylphenyl with SO$_2$NHBu(t) | 3-chloro-1,4-phenylene | pyridin-4-yl | 1,4-phenylene |
| 2-methylphenyl with SO$_2$Me | 2,3-difluoro-1,4-phenylene | pyridin-3-yl | pyridin-2,5-diyl |
| 2-methylphenyl with CH$_2$NH$_2$ | 2,4-difluoro-1,5-phenylene | 6-amino-pyridin-3-yl | pyridin-2,5-diyl |
| 2-methylphenyl with CH$_2$NHMe | 3-fluoro-1,4-phenylene | 2-amino-pyridin-4-yl | pyrimidin-2,5-diyl | wherein R$^{1b}$ is a member selected from the group consisting of H, F, —OH, Br, Cl, —NH$_2$, —O—CH$_2$—O—Ph and —O—CH$_2$—CH$_2$—O—CH$_3$, TABLE 8c
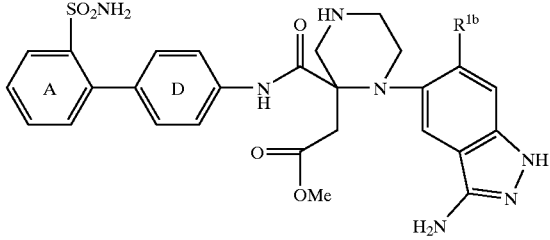
Formula IXc
| A | D | A | D |
|---|---|---|---|
| 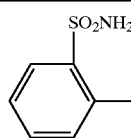 | 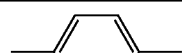 | 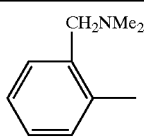 | 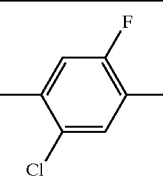 |
| 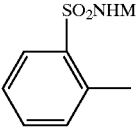 | 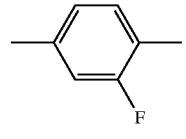 | 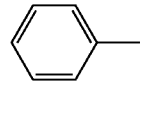 | 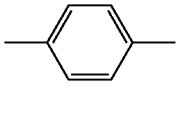 |
| 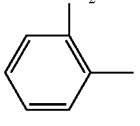 | 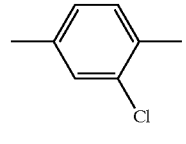 | 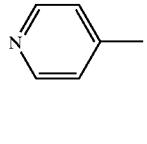 | 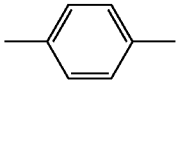 |
| 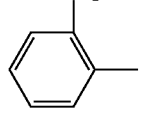 | 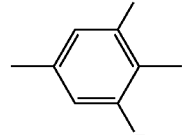 | 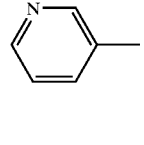 | 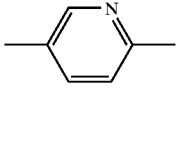 |
| 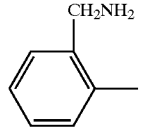 | 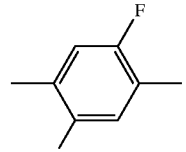 | 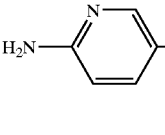 | 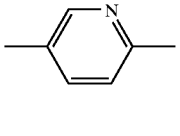 |
| 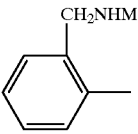 | 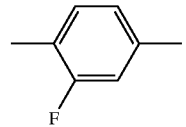 | 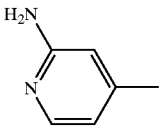 | 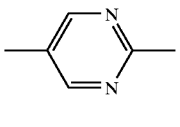 |
wherein $R^{1b}$ is a member selected from the group consisting of H, F, —OH, Br, Cl, —NH$_2$, —O—CH$_2$—O—Ph and —O—CH$_2$—CH$_2$—O—CH$_3$, … TABLE 8d
Formula IXd
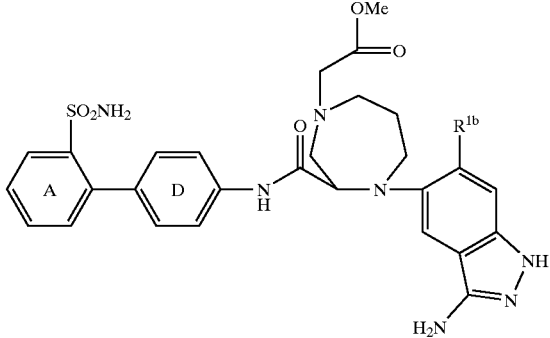
| A | D | A | D |
|---|---|---|---|
| 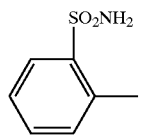 | 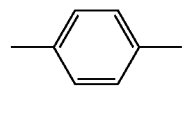 | 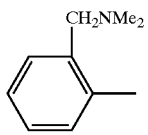 | 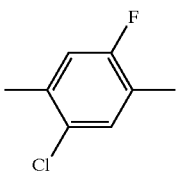 |
| 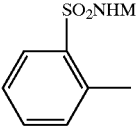 | 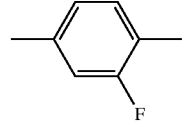 | 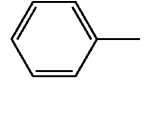 | 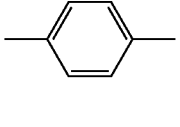 |
| 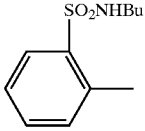 | 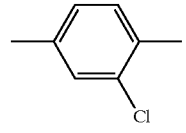 | 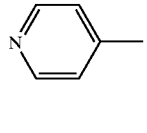 | 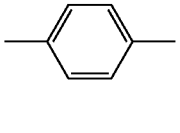 |
| 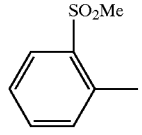 | 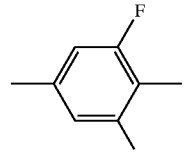 | 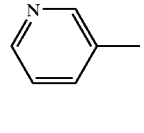 | 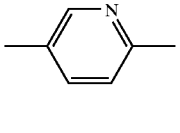 |
| 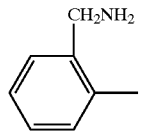 | 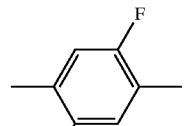 | 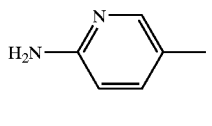 | 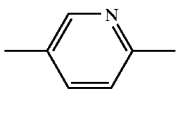 |
| 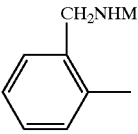 | 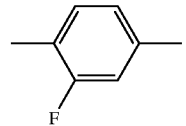 | 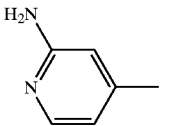 | 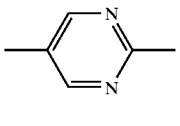 |
wherein $R^{1b}$ is a member selected from the group consisting of H, F, —OH, Br, Cl, —NH$_2$, —O—CH$_2$—O—Ph and —O—CH$_2$—CH$_2$—O—CH$_3$, TABLE 8e Formula IXe wherein $R^{1b}$ is a member selected from the group consisting of H, F, —OH, Br, Cl, —NH$_2$, —O—CH$_2$—O—Ph and —O—CH$_2$—CH$_2$—O—CH$_3$,

TABLE 9

TABLE 9a
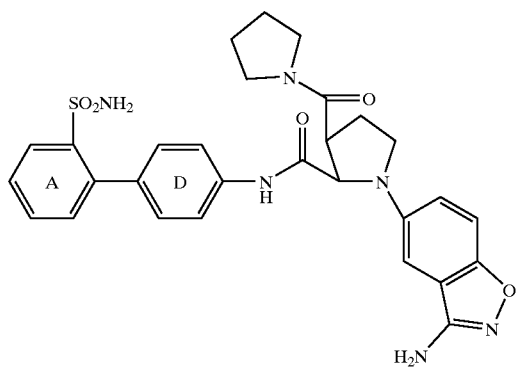

TABLE 9b
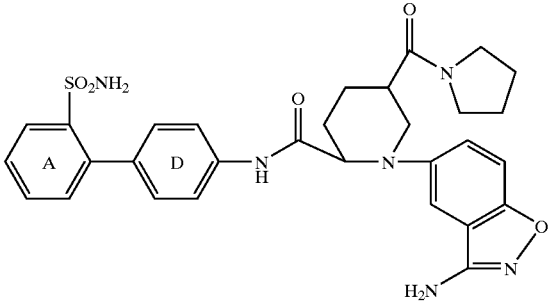
Formula Xb
| A | D | A | D |
|---|---|---|---|
| 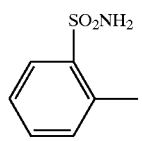 | 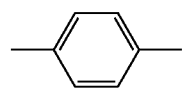 | 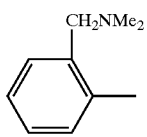 | 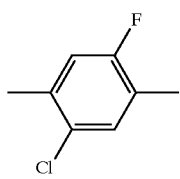 |
| 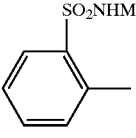 | 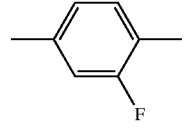 | 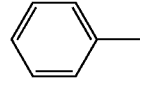 | 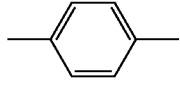 |
| 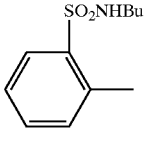 | 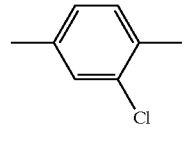 | 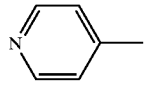 | 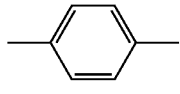 |
| 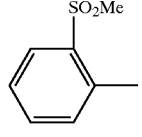 | 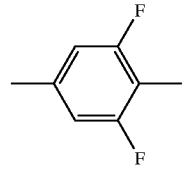 | 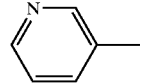 | 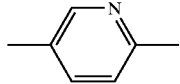 |
| 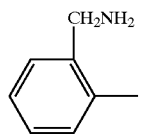 | 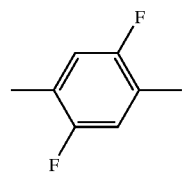 | 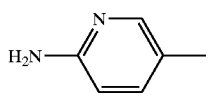 | 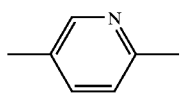 |
| 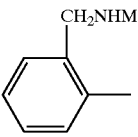 | 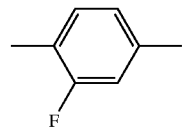 | 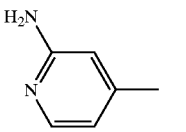 | 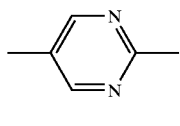 |

TABLE 9c
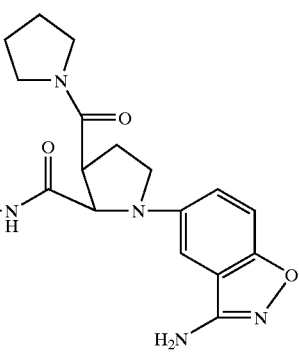
Formula Xc
| A | D | A | D |
|---|---|---|---|
| 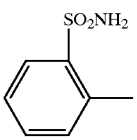 | 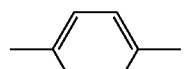 | 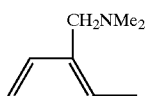 | 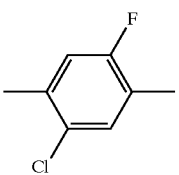 |
| 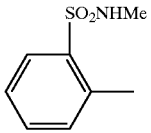 | 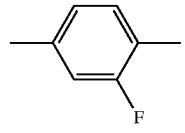 | 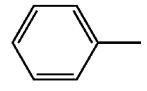 | 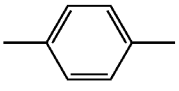 |
| 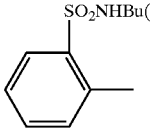 | 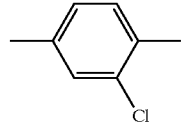 | 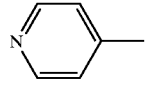 | 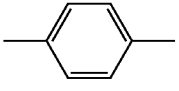 |
| 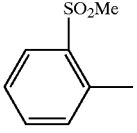 | 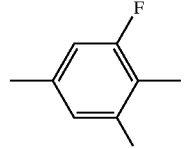 | 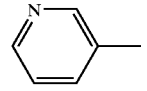 | 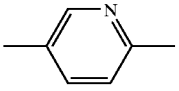 |
| 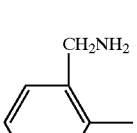 | 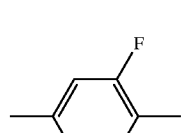 | 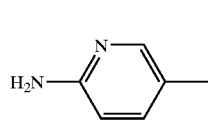 | 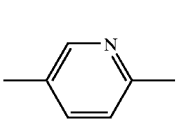 |
| 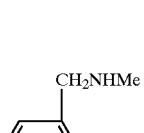 | 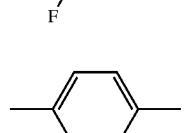 | 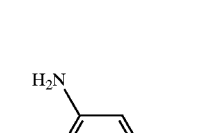 | 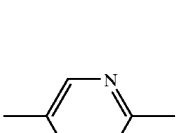 |

TABLE 9d

TABLE 9e
Formula Xe
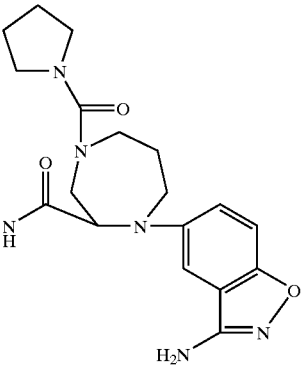
| A | D | A | D |
|---|---|---|---|
| 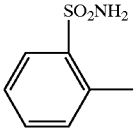 |  | 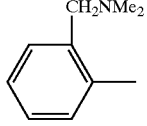 | 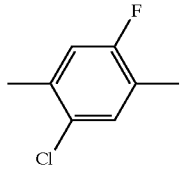 |
| 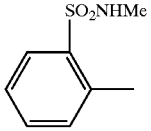 | 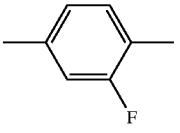 | 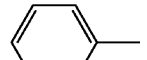 |  |
| 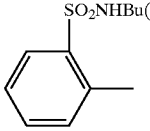 | 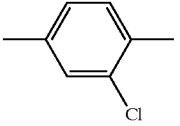 | 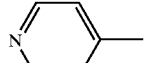 | 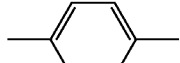 |
| 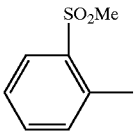 | 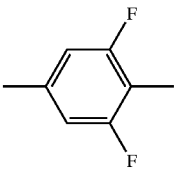 | 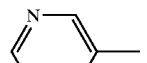 | 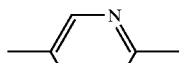 |
| 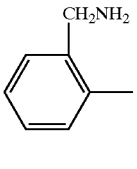 | 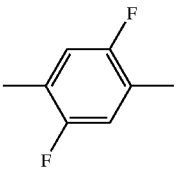 | 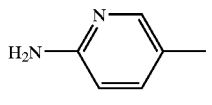 | 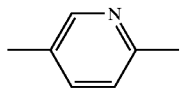 |
| 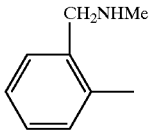 | 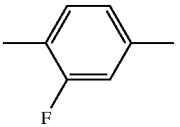 | 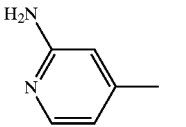 | 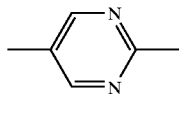 |

TABLE 10
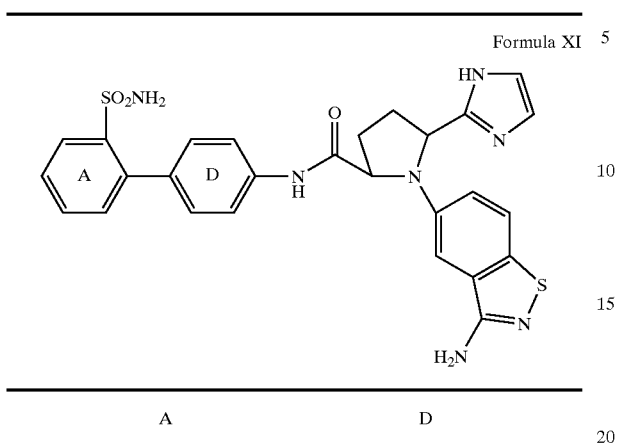
Formula XI
| A | D |
|---|---|
| 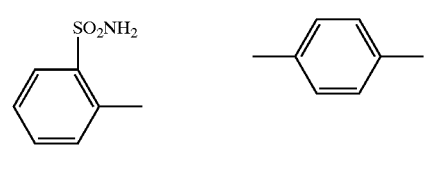 | 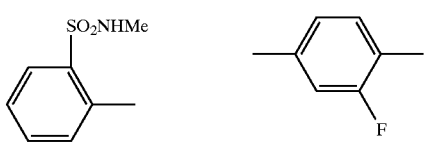 |
| 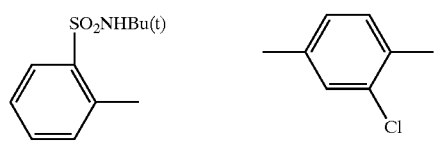 | 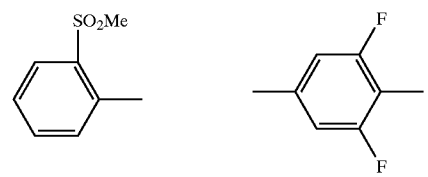 |
| 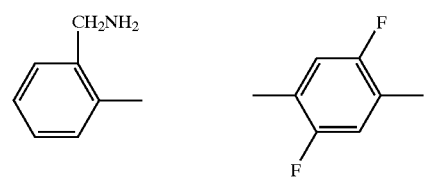 | 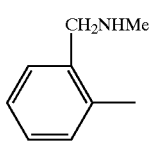 |
TABLE 10-continued
| A | D |
|---|---|
| 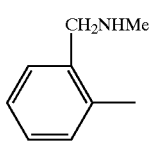 | 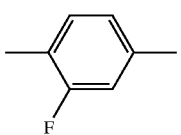 |
| 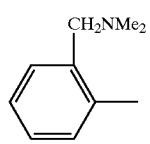 | 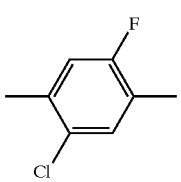 |
| 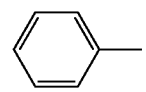 | 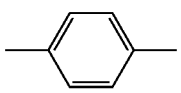 |
| 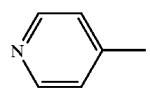 | 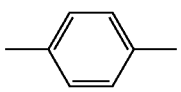 |
| 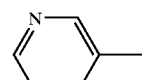 | 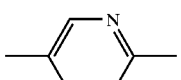 |
| 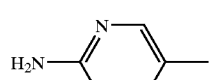 | 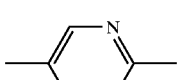 |

TABLE 10a

Formula XIa

| A | D | A | D |
|---|---|---|---|
| 2-methylphenyl-SO₂NH₂ | 1,4-phenylene | 2-methylphenyl-CH₂NMe₂ | 4-fluoro-2-chloro-phenylene |
| 2-methylphenyl-SO₂NHMe | 3-fluoro-1,4-phenylene | phenyl | 1,4-phenylene |
| 2-methylphenyl-SO₂NHBu(t) | 3-chloro-1,4-phenylene | pyridin-4-yl | 1,4-phenylene |
| 2-methylphenyl-SO₂Me | 3,5-difluoro-1,4-phenylene | pyridin-3-yl | pyridin-2,5-diyl |
| 2-methylphenyl-CH₂NH₂ | 3,5-difluoro-1,4-phenylene | 6-amino-pyridin-3-yl | pyridin-2,5-diyl |
| 2-methylphenyl-CH₂NHMe | 3-fluoro-1,4-phenylene | 2-amino-pyridin-4-yl | pyrimidin-2,5-diyl |

TABLE 10b

Formula XIb

| A | D | A | D |
|---|---|---|---|
| 2-methyl-phenyl, SO$_2$NH$_2$ | 1,4-phenylene | 2-methyl-phenyl, CH$_2$NMe$_2$ | 5-fluoro-2-chloro-phenylene |
| 2-methyl-phenyl, SO$_2$NHMe | 3-fluoro-phenylene | phenyl | 1,4-phenylene |
| 2-methyl-phenyl, SO$_2$NHBu(t) | 3-chloro-phenylene | 4-pyridyl | 1,4-phenylene |
| 2-methyl-phenyl, SO$_2$Me | 3,4-difluoro-phenylene | 3-pyridyl | 2,5-pyridyl |
| 2-methyl-phenyl, CH$_2$NH$_2$ | 2,5-difluoro-phenylene | 2-amino-5-pyridyl | 2,5-pyridyl |
| 2-methyl-phenyl, CH$_2$NHMe | 3-fluoro-phenylene | 2-amino-4-pyridyl | 2,5-pyrimidyl |

TABLE 10c
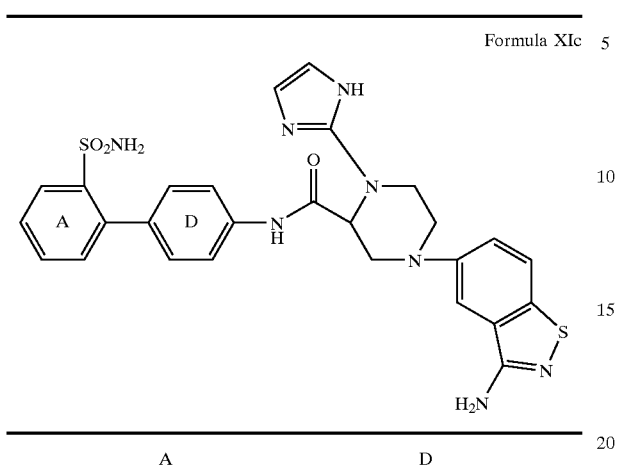
Formula XIc
| A | D |
|---|---|
| 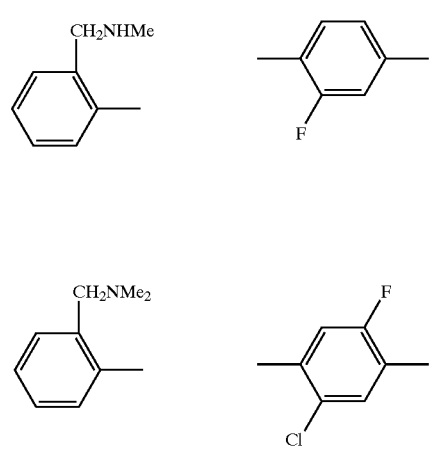 | |
TABLE 10c-continued
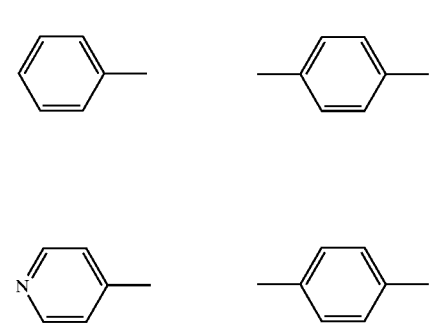

TABLE 10d
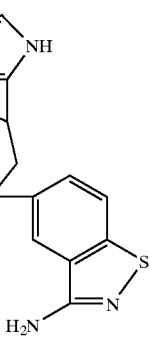
Formula XId
| A | D | A | D |
|---|---|---|---|
| 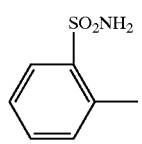 | 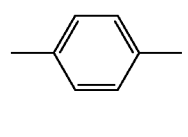 | 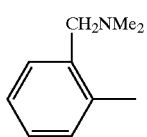 | 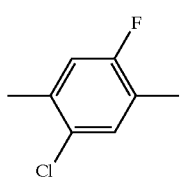 |
| 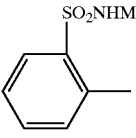 | 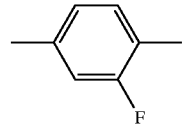 | 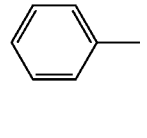 | 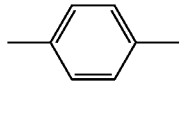 |
| 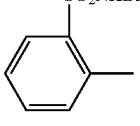 | 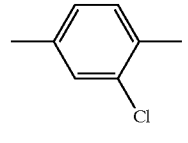 | 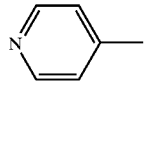 | 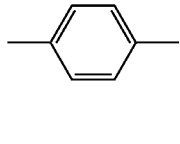 |
| 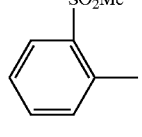 | 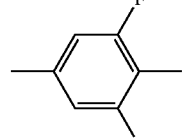 | 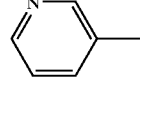 | 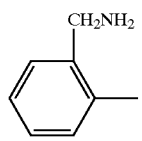 |
| 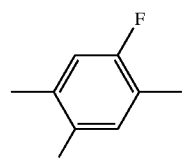 | 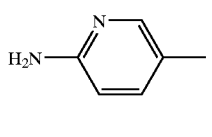 | 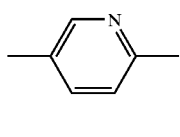 | 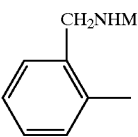 |
| 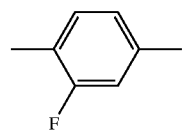 | 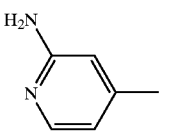 | 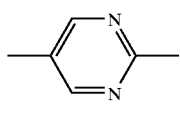 | |

TABLE 10e

Formula XIe

| A | D | A | D |
|---|---|---|---|
| 2-SO₂NH₂-phenyl | 1,4-phenylene | 2-CH₂NMe₂-phenyl | 5-F,2-Cl-1,4-phenylene |
| 2-SO₂NHMe-phenyl | 3-F-1,4-phenylene | phenyl | 1,4-phenylene |
| 2-SO₂NHBu(t)-phenyl | 3-Cl-1,4-phenylene | pyridin-4-yl | 1,4-phenylene |
| 2-SO₂Me-phenyl | 2,3-diF-1,4-phenylene | pyridin-3-yl | pyridin-2,5-diyl |
| 2-CH₂NH₂-phenyl | 2,5-diF-1,4-phenylene | 2-amino-pyridin-5-yl | pyridin-2,5-diyl |
| 2-CH₂NHMe-phenyl | 3-F-1,4-phenylene | 2-amino-pyridin-4-yl | pyrimidin-2,5-diyl |

TABLE 11

Formula XII

| A | D | A | D |
|---|---|---|---|
| 2-SO$_2$NH$_2$-phenyl | 1,4-phenylene | 2-CH$_2$NMe$_2$-phenyl | 5-F, 2-Cl-1,4-phenylene |
| 2-SO$_2$NHMe-phenyl | 3-F-1,4-phenylene | phenyl | 1,4-phenylene |
| 2-SO$_2$NHBu(t)-phenyl | 3-Cl-1,4-phenylene | 4-pyridyl | 1,4-phenylene |
| 2-SO$_2$Me-phenyl | 2,3-F$_2$-1,4-phenylene | 3-pyridyl | 2,5-pyridyl |
| 2-CH$_2$NH$_2$-phenyl | 2,5-F$_2$-1,4-phenylene | 6-NH$_2$-3-pyridyl | 2,5-pyridyl |
| 2-CH$_2$NHMe-phenyl | 3-F-1,4-phenylene | 2-NH$_2$-4-pyridyl | 2,5-pyrimidyl |

TABLE 11a
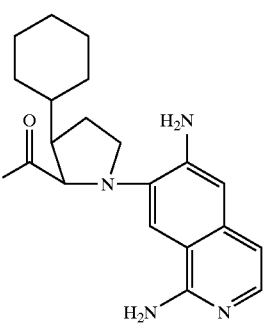
Formula XIIa
| A | D | A | D |
|---|---|---|---|
| 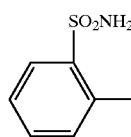 | 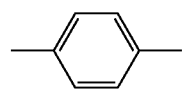 | 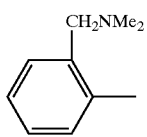 | 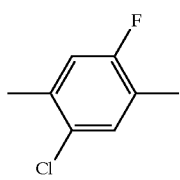 |
| 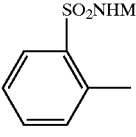 | 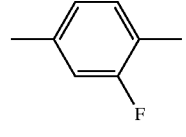 | 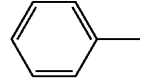 | 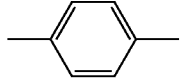 |
| 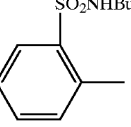 | 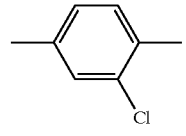 | 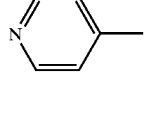 | 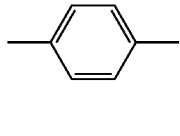 |
| 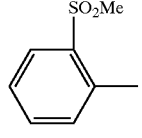 | 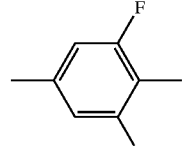 | 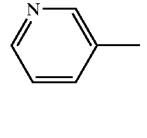 | 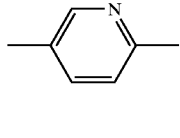 |
| 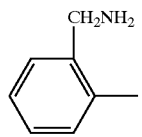 | 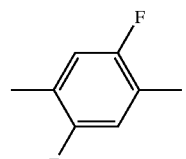 | 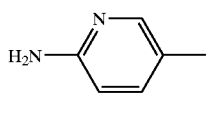 | 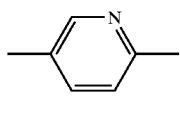 |
| 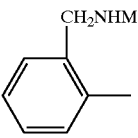 | 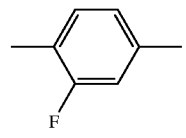 | 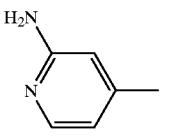 | 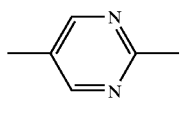 |

TABLE 11b
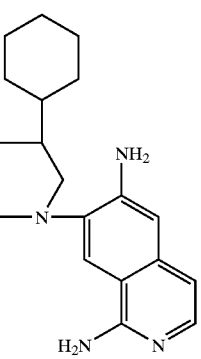
Formula XIIb
| A | D | A | D |
|---|---|---|---|
| 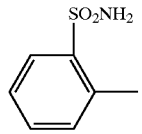 | 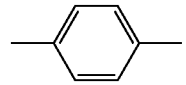 | 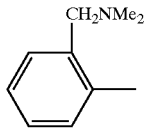 | 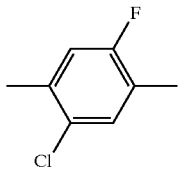 |
|  | 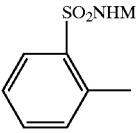 | 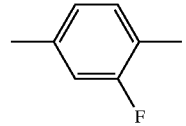 | 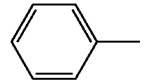 |
| 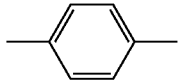 | 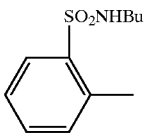 | 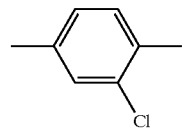 | 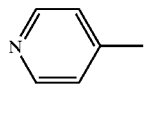 |
| 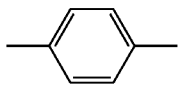 | 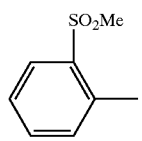 | 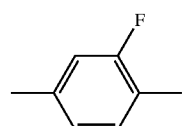 | 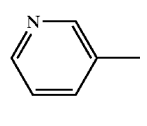 |
| 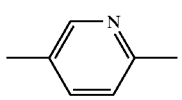 | 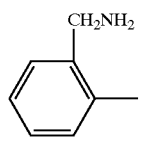 | 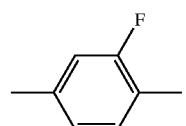 | 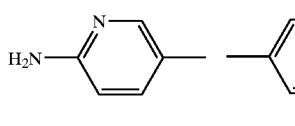 |
|  | 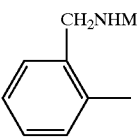 | 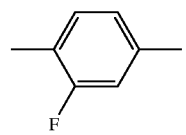 | 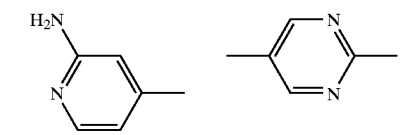 |

TABLE 11c
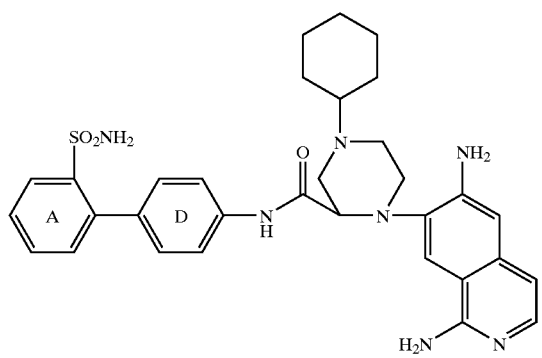
Formula XIIc

TABLE 11d
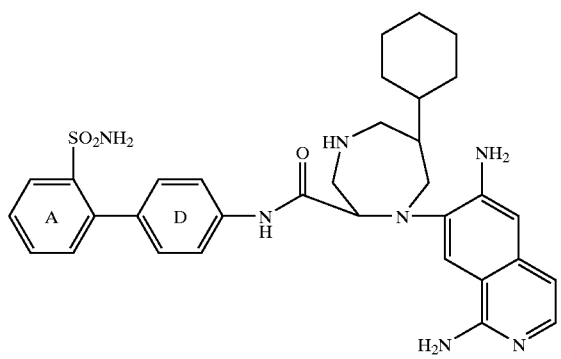
Formula XIId
| A | D | A | D |
|---|---|---|---|
| 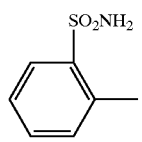 | 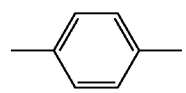 | 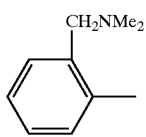 | 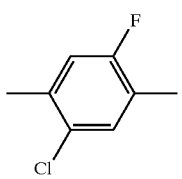 |
| 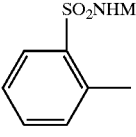 | 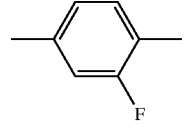 | 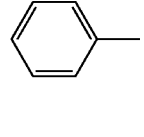 | 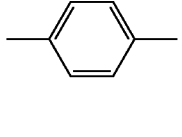 |
| 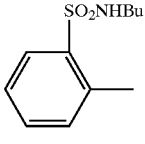 | 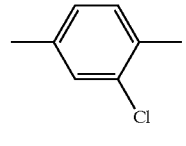 | 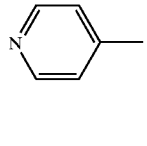 | 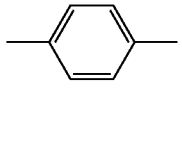 |
| 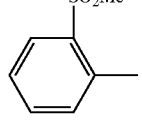 | 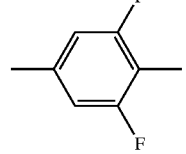 | 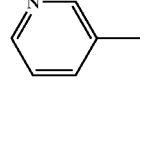 | 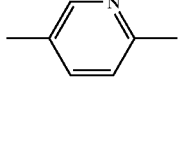 |
| 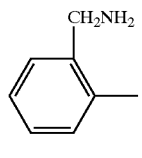 | 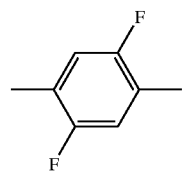 | 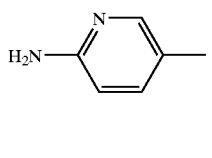 | 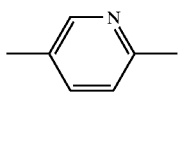 |
| 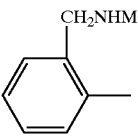 | 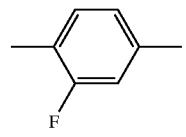 | 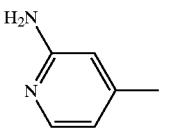 | 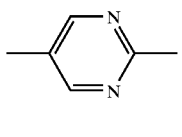 |

TABLE 11e

Formula XIIe

| A | D | A | D |
|---|---|---|---|
| 2-SO₂NH₂-phenyl | 1,4-phenyl | 2-CH₂NMe₂-phenyl | 5-F,2-Cl-phenyl |
| 2-SO₂NHMe-phenyl | 3-F-1,4-phenyl | phenyl | 1,4-phenyl |
| 2-SO₂NHBu(t)-phenyl | 3-Cl-1,4-phenyl | 4-pyridyl | 1,4-phenyl |
| 2-SO₂Me-phenyl | 3,5-diF-1,4-phenyl | 3-pyridyl | 2,5-pyridyl |
| 2-CH₂NH₂-phenyl | 2,5-diF-1,4-phenyl | 6-NH₂-3-pyridyl | 2,5-pyridyl |
| 2-CH₂NHMe-phenyl | 3-F-1,4-phenyl | 2-NH₂-4-pyridyl | 2,5-pyrimidyl |

TABLE 12
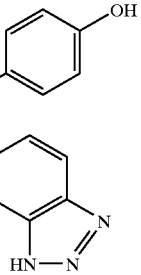
Formula XIII
| A | D | A | D |
|---|---|---|---|
| 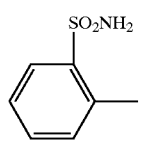 | 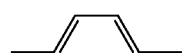 | 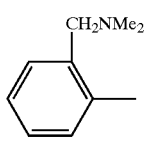 | 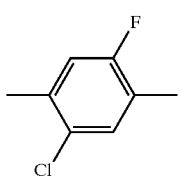 |
| 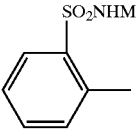 | 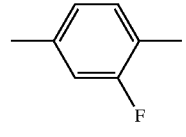 | 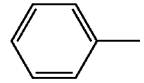 |  |
| 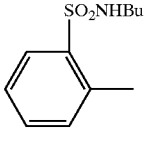 | 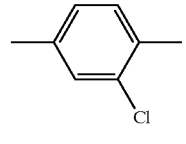 | 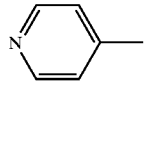 | 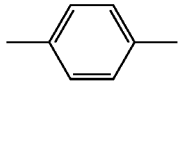 |
| 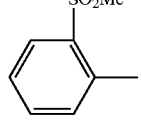 | 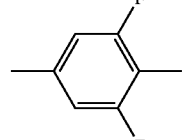 | 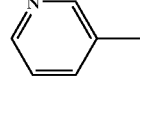 | 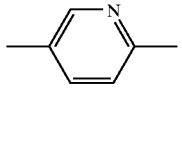 |
| 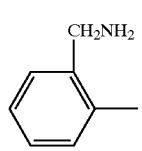 | 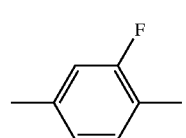 | 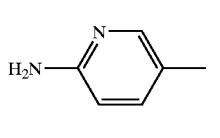 | 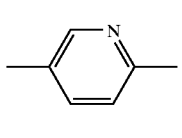 |
| 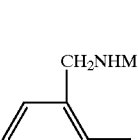 | 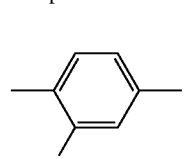 | 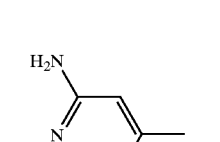 | 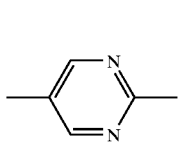 |

TABLE 12a

Formula XIIIa

| A | D | A | D |
|---|---|---|---|
| 2-Me-C₆H₃(SO₂NH₂) | 1,4-C₆H₄ | 2-Me-C₆H₃(CH₂NMe₂) | 5-Cl-2,4-F-C₆H₂ (F at 4, Cl at 5) |
| 2-Me-C₆H₃(SO₂NHMe) | 3-F-1,4-C₆H₃ | C₆H₅ | 1,4-C₆H₄ |
| 2-Me-C₆H₃(SO₂NHBu(t)) | 3-Cl-1,4-C₆H₃ | pyridin-4-yl | 1,4-C₆H₄ |
| 2-Me-C₆H₃(SO₂Me) | 2,3-diF-1,4-C₆H₃ | pyridin-3-yl | pyridin-2,5-diyl |
| 2-Me-C₆H₃(CH₂NH₂) | 2,5-diF-1,4-C₆H₃ | 6-amino-pyridin-3-yl | pyridin-2,5-diyl |
| 2-Me-C₆H₃(CH₂NHMe) | 3-F-1,4-C₆H₃ | 2-amino-pyridin-4-yl | pyrimidin-2,5-diyl |

TABLE 12b
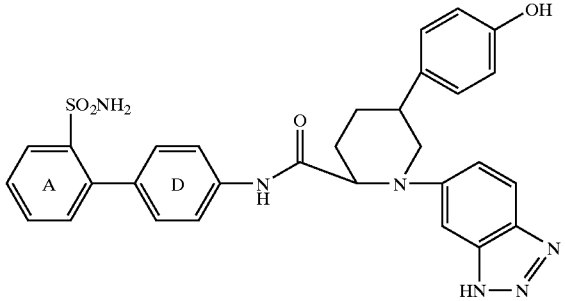
Formula XIII
| A | D | A | D |
|---|---|---|---|
| 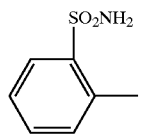 | 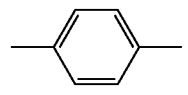 | 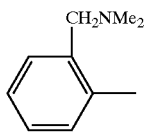 | 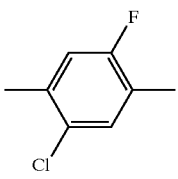 |
| 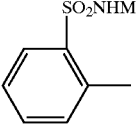 | 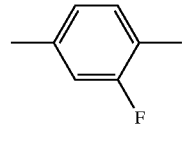 | 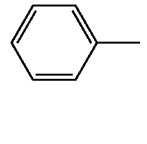 | 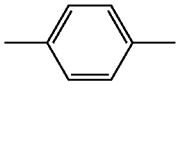 |
| 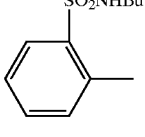 | 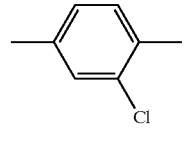 | 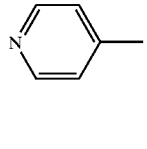 | 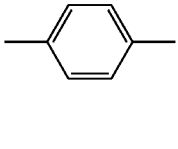 |
| 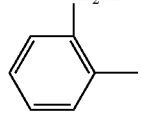 | 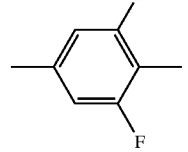 | 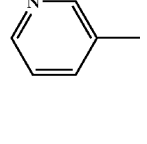 | 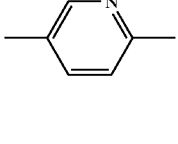 |
| 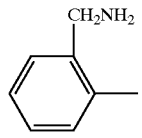 | 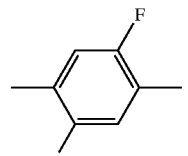 | 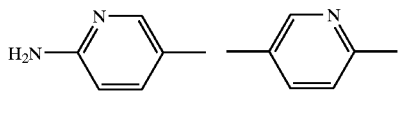 | 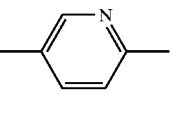 |
| 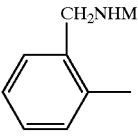 | 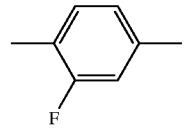 | 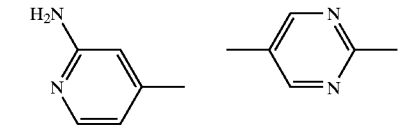 | 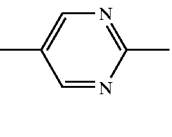 |

TABLE 12c

Formula XIIIc

| A | D | A | D |
|---|---|---|---|
| 2-SO₂NH₂-phenyl (with 2-Me) | 4-phenyl | 2-CH₂NMe₂-phenyl (with 2-Me) | 2-F,5-Cl-phenyl |
| 2-SO₂NHMe-phenyl (with 2-Me) | 3-F-phenyl | phenyl | 4-phenyl |
| 2-SO₂NHBu(t)-phenyl (with 2-Me) | 3-Cl-phenyl | 4-pyridyl | 4-phenyl |
| 2-SO₂Me-phenyl (with 2-Me) | 2,3-diF-phenyl | 3-pyridyl | 2-pyridyl (5-) |
| 2-CH₂NH₂-phenyl (with 2-Me) | 2,5-diF-phenyl (4-F) | 2-NH₂-5-pyridyl | 2-pyridyl (5-) |
| 2-CH₂NHMe-phenyl (with 2-Me) | 3-F-phenyl | 2-NH₂-4-pyridyl | 2-pyrimidinyl (5-) |

TABLE 12d

Formula XIIId

| A | D | A | D |
|---|---|---|---|
| 2-(SO₂NH₂)-phenyl, methyl | 1,4-phenylene | 2-(CH₂NMe₂)-phenyl, methyl | 2-F, 5-Cl-1,4-phenylene |
| 2-(SO₂NHMe)-phenyl, methyl | 3-F-1,4-phenylene | phenyl | 1,4-phenylene |
| 2-(SO₂NHBu(t))-phenyl, methyl | 3-Cl-1,4-phenylene | pyridin-4-yl | 1,4-phenylene |
| 2-(SO₂Me)-phenyl, methyl | 2,3-diF-1,4-phenylene | pyridin-3-yl | 6-pyridin-3-yl (2,5-) |
| 2-(CH₂NH₂)-phenyl, methyl | 2,5-diF-1,4-phenylene | 2-amino-pyridin-5-yl | 2-amino-pyridin-5-yl |
| 2-(CH₂NHMe)-phenyl, methyl | 3-F-1,4-phenylene | 2-amino-pyridin-4-yl | pyrimidin-2,5-diyl |

TABLE 12e

Formula XIIIe

TABLE 13

TABLE 13a

TABLE 13b

Formula XIVb

| A | D | A | D |
|---|---|---|---|
| 2-SO₂NH₂-phenyl | 1,4-phenyl | 3-CH₂NMe₂-pyridin-2-yl | 5-F, 4-Cl-1,3-phenyl |
| 2-SO₂NHMe-phenyl | 3-F-1,4-phenyl | phenyl | 1,4-phenyl |
| 2-SO₂NHBu(t)-phenyl | 3-Cl-1,4-phenyl | pyridin-4-yl | 1,4-phenyl |
| 2-SO₂Me-phenyl | 3,4-diF-1,4-phenyl | pyridin-3-yl | pyridin-2,5-diyl |
| 2-CH₂NH₂-phenyl | 3,5-diF-1,4-phenyl | 6-NH₂-pyridin-3-yl | pyridin-2,5-diyl |
| 2-CH₂NHMe-phenyl | 3-F-1,4-phenyl | 2-NH₂-pyridin-4-yl | pyrimidin-2,5-diyl |

TABLE 13c

Formula XIVc

| A | D | A | D |
|---|---|---|---|
| 2-SO₂NH₂-phenyl | 1,4-phenyl | 2-CH₂NMe₂-pyridin-3-yl | 5-F,2-Cl-phenyl (4-position) |
| 2-SO₂NHMe-phenyl | 3-F-1,4-phenyl | phenyl | 1,4-phenyl |
| 2-SO₂NHBu(t)-phenyl | 3-Cl-1,4-phenyl | pyridin-4-yl | 1,4-phenyl |
| 2-SO₂Me-phenyl | 2,3-diF-1,4-phenyl | pyridin-3-yl | pyridin-2,5-diyl |
| 2-CH₂NH₂-phenyl | 3,5-diF-1,4-phenyl | 2-NH₂-pyridin-5-yl | pyridin-2,5-diyl |
| 2-CH₂NHMe-phenyl | 3-F-1,4-phenyl | 2-NH₂-pyridin-4-yl | pyrimidin-2,5-diyl |

TABLE 14
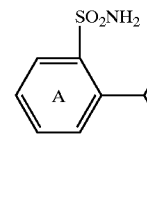
Formula XV
| A | D | A | D |
|---|---|---|---|
| 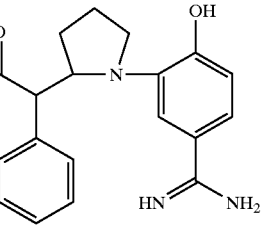 | 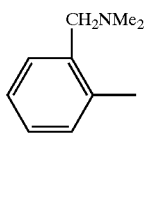 | 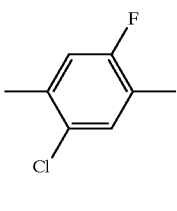 | 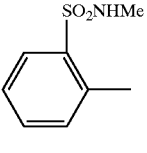 |
| 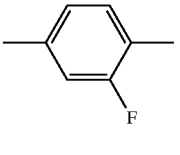 | 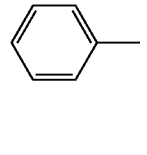 | 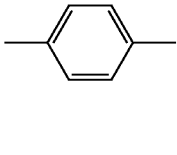 | 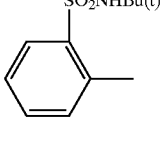 |
| 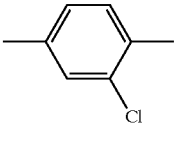 | 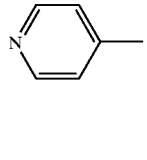 | 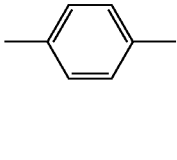 | 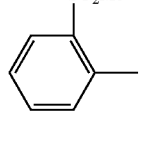 |
| 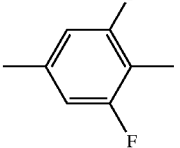 | 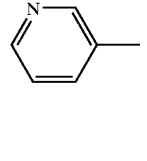 | 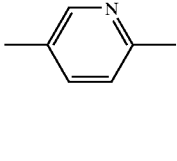 | 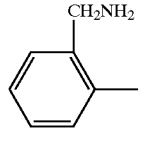 |
| 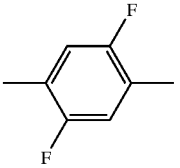 | 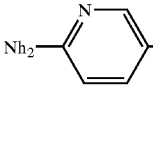 | 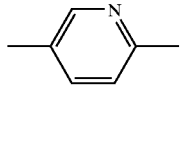 | 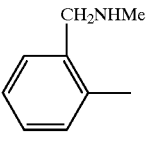 |
| 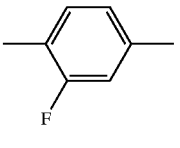 | 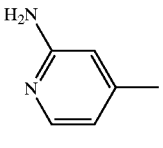 | 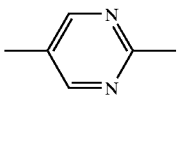 |  |

TABLE 14a

Formula XVa

TABLE 14b
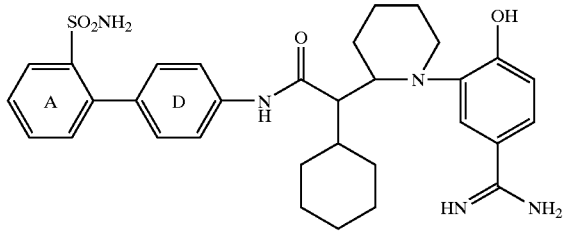
Formula XVb
| A | D | A | D |
|---|---|---|---|
| 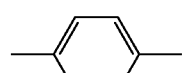 | 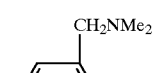 | 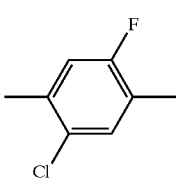 | 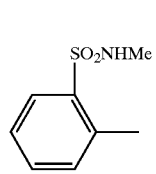 |
| 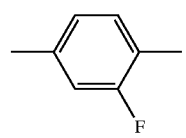 | 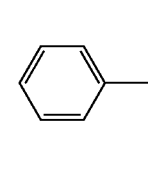 | 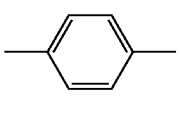 | 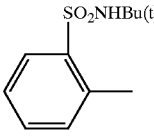 |
| 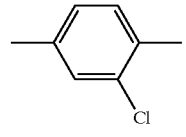 | 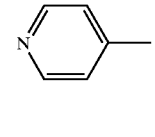 | 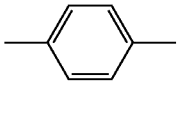 | 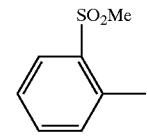 |
| 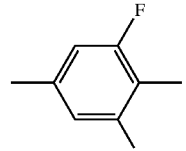 | 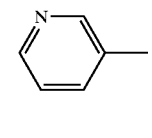 | 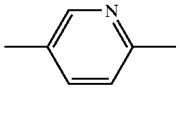 | 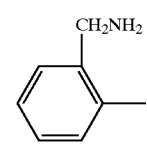 |
| 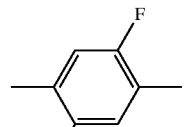 | 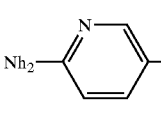 | 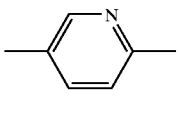 | 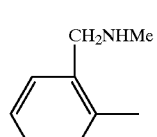 |
| 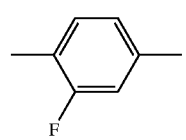 | 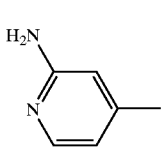 | 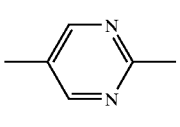 |  |

TABLE 14c
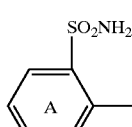
Formula XVc
| A | D | A | D |
|---|---|---|---|
| 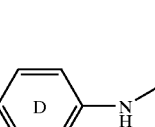 | 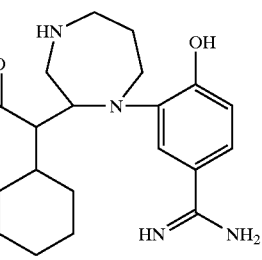 |  | 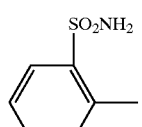 |
| 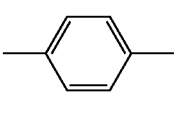 | 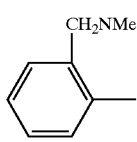 | 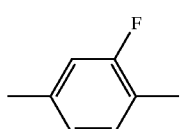 | 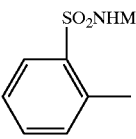 |
| 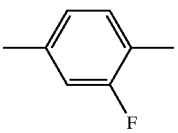 | 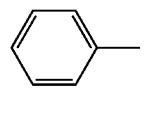 | 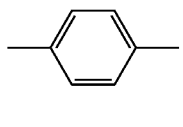 | 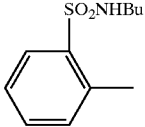 |
| 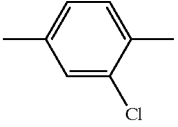 | 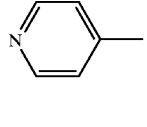 | 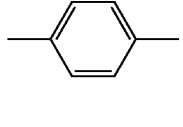 | 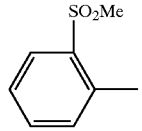 |
| 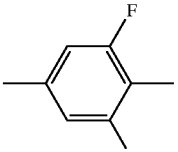 | 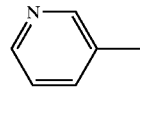 | 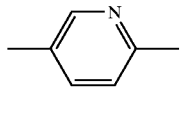 | 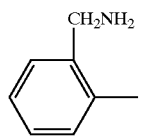 |
| 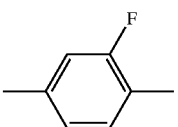 | 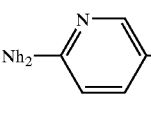 | 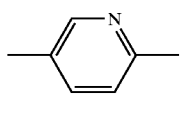 | 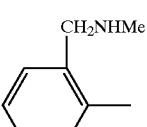 |

TABLE 15

Formula XVI

| A | D | A | D |
|---|---|---|---|
| 2-Me-C6H4-SO2NH2 | 1,4-C6H4 | 2-Me-C6H4-CH2NMe2 | 5-Cl-2,4-F-C6H3 |
| 2-Me-C6H4-SO2NHMe | 3-F-1,4-C6H3 | C6H5 | 1,4-C6H4 |
| 2-Me-C6H4-SO2NHBu(t) | 3-Cl-1,4-C6H3 | 4-pyridyl | 1,4-C6H4 |
| 2-Me-C6H4-SO2Me | 3,5-F2-1,4-C6H2 | 3-pyridyl | 2,5-pyridyl |
| 2-Me-C6H4-CH2NH2 | 3,5-F2-1,4-C6H2 | 6-NH2-3-pyridyl | 2,5-pyridyl |
| 2-Me-C6H4-CH2NHMe | 3-F-1,4-C6H3 | 2-NH2-4-pyridyl | 2,5-pyrimidinyl |

TABLE 15a
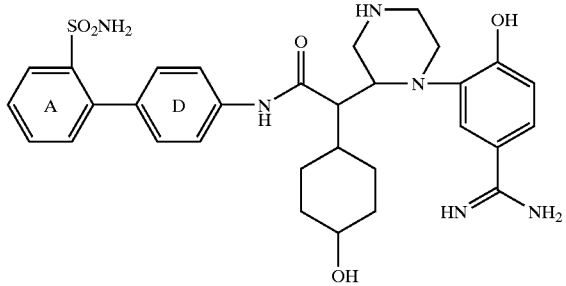
Formula XVIa
| A | D | A | D |
|---|---|---|---|
| SO₂NH₂ (2-Me-phenyl) | 1,4-phenyl | CH₂NMe₂ (2-Me-phenyl) | 5-F, 2-Cl-phenyl |
| SO₂NHMe (2-Me-phenyl) | 3-F-phenyl | phenyl | 1,4-phenyl |
| SO₂NHBu(t) (2-Me-phenyl) | 3-Cl-phenyl | 4-pyridyl | 1,4-phenyl |
| SO₂Me (2-Me-phenyl) | 3,4-diF-phenyl | 3-pyridyl | 2,5-pyridyl |
| CH₂NH₂ (2-Me-phenyl) | 3,5-diF-phenyl | 6-NH₂-3-pyridyl | 2,5-pyridyl |
| CH₂NHMe (2-Me-phenyl) | 3-F-phenyl | 2-NH₂-4-pyridyl | 2,5-pyrimidyl |

TABLE 15b

Formula XVIb

TABLE 15c
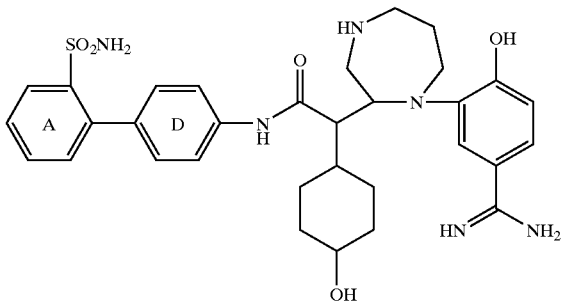
Formula XVIc
| A | D | A | D |
|---|---|---|---|
| 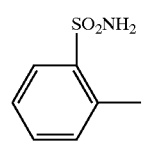 | 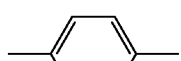 | 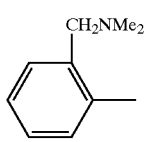 | 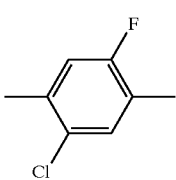 |
| 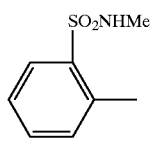 | 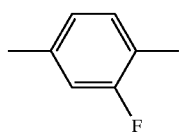 | 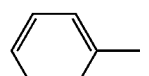 | 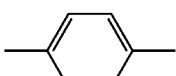 |
| 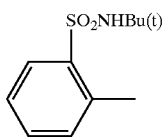 | 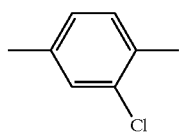 | 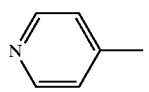 | 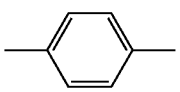 |
| 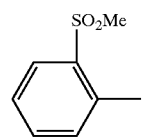 | 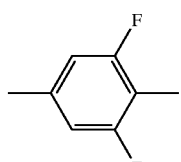 | 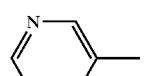 | 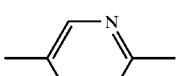 |
| 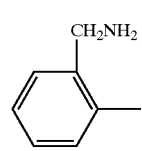 | 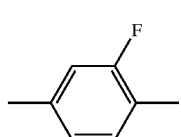 | 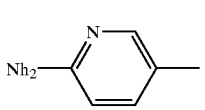 | 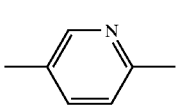 |
| 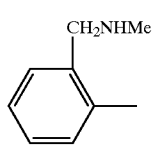 | 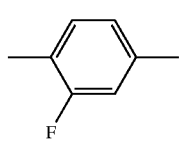 | 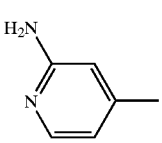 | 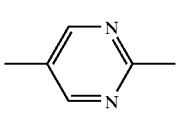 |

TABLE 16
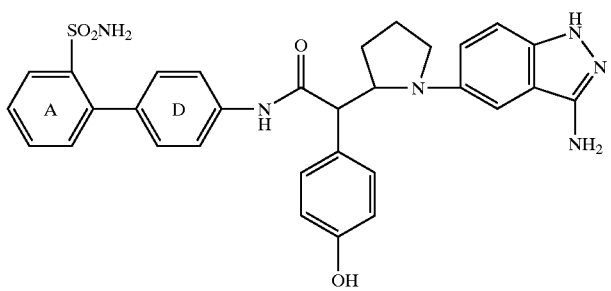
Formula XVII
| A | D | A | D |
|---|---|---|---|
| 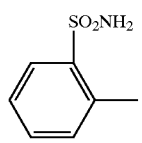 | 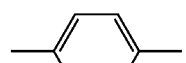 | 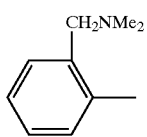 | 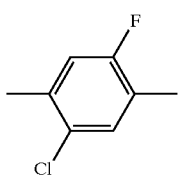 |
| 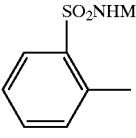 | 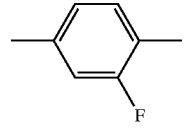 | 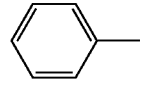 | 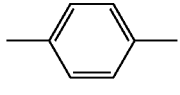 |
| 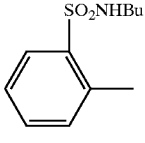 | 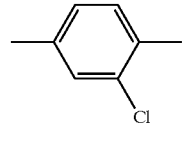 | 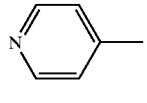 | 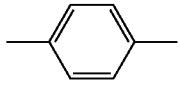 |
| 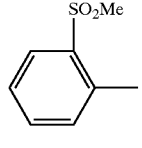 | 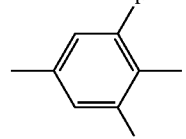 | 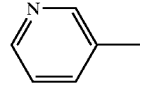 | 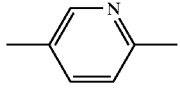 |
| 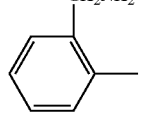 | 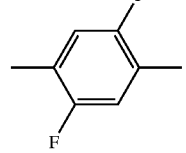 | 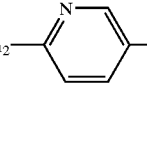 | 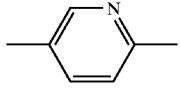 |
| 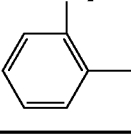 | 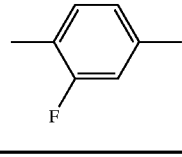 | 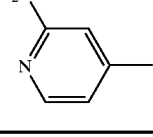 | 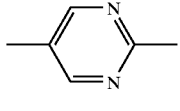 |

TABLE 16a
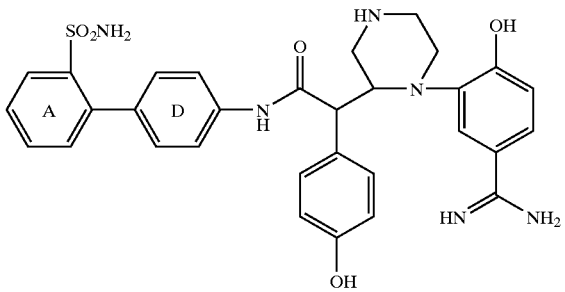
Formula XVIIa
| A | D | A | D |
|---|---|---|---|
| 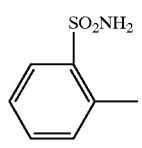 | 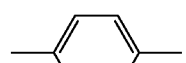 | 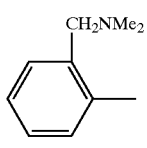 | 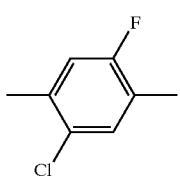 |
| 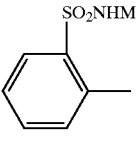 | 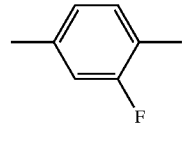 | 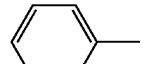 | 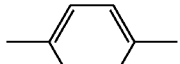 |
| 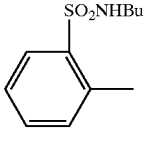 | 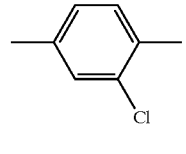 | 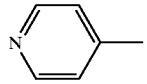 |  |
| 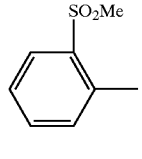 | 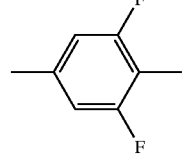 | 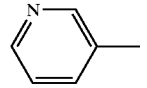 |  |
| 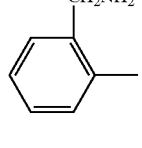 | 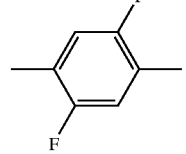 | 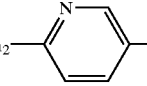 |  |
| 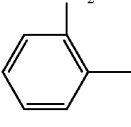 | 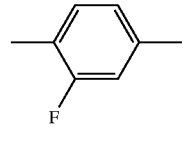 | 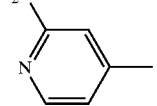 | 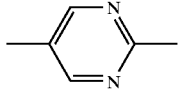 |

TABLE 16b
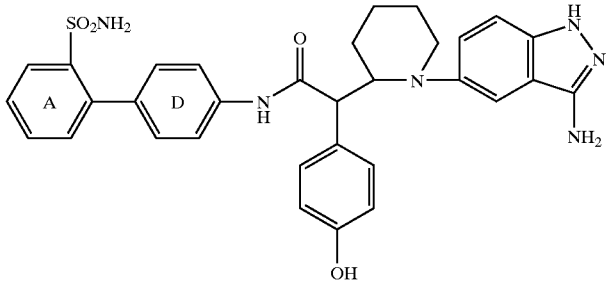
Formula XVIIb
| A | D | A | D |
|---|---|---|---|
| 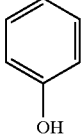 | 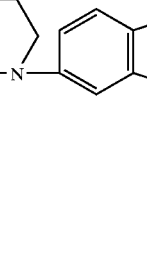 | 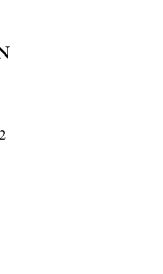 | 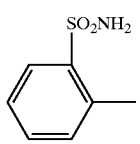 |
| 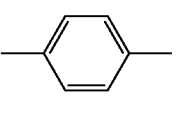 | 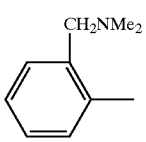 | 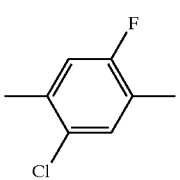 | 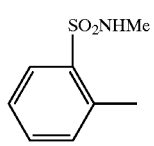 |
| 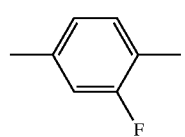 | 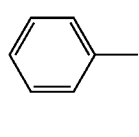 | 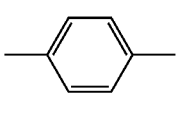 | 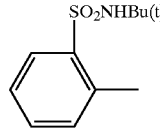 |
| 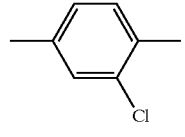 | 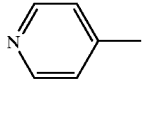 | 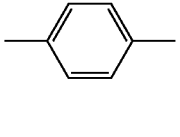 | 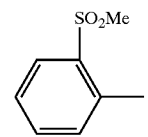 |
| 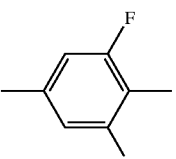 | 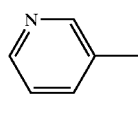 | 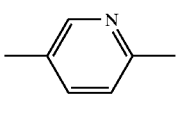 | 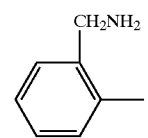 |
| 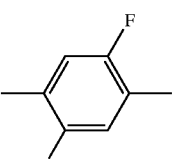 | 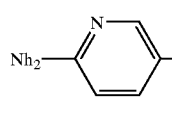 | 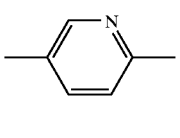 | 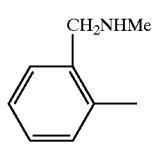 |

TABLE 16c
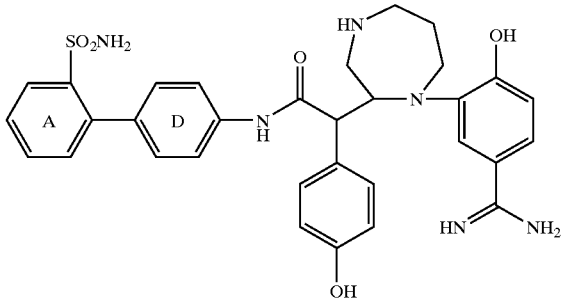
Formula XVIIc
| A | D | A | D |
|---|---|---|---|
| 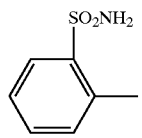 | 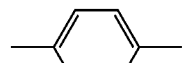 | 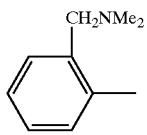 | 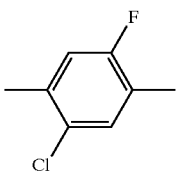 |
| 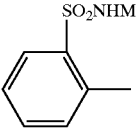 | 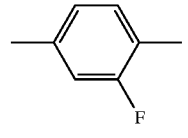 | 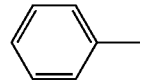 |  |
| 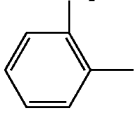 | 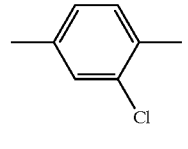 | 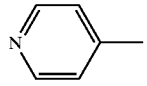 |  |
| 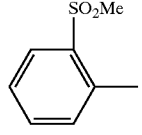 | 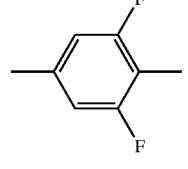 | 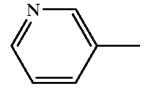 |  |
| 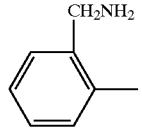 | 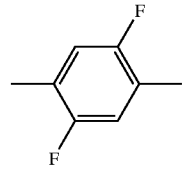 | 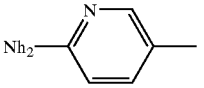 | 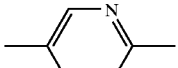 |
| 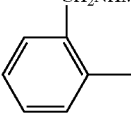 | 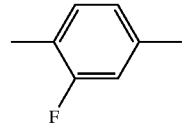 | 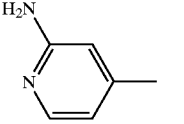 |  |

TABLE 17
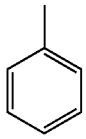
Formula XVIII
| R⁷ | R¹¹ | R¹ᵇ' | R¹ᵇ" |
|---|---|---|---|
| H | H | H | H |
| Me | H | H | OH |
|  | 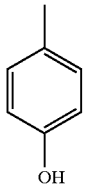 | F | H |
| 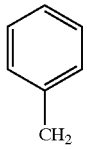 | 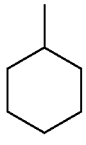 | —OH | F |
| 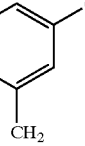 | 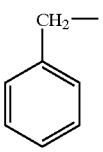 | OH | OH |
| 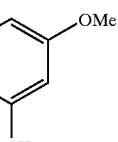 | 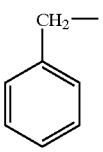 | —NH₂ | H |
TABLE 17a
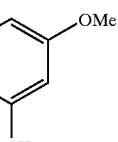
Formula XVIIIa
| R⁷ | R¹¹ | R¹ᵇ' | R¹ᵇ" |
|---|---|---|---|
| H | H | H | H |
| Me | H | H | OH |
| 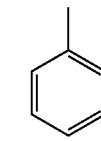 | 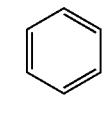 | F | H |
| 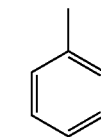 | 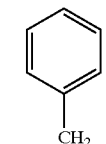 | —OH | F |
| 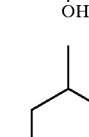 | 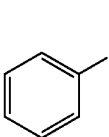 | OH | OH |
|  |  | —NH₂ | H |
TABLE 17b
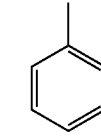
Formula XVIIIb
| R⁷ | R¹¹ | R¹ᵇ' | R¹ᵇ" |
|---|---|---|---|
| H | H | H | H |
| Me | H | H | OH |
| 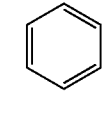 | | F | H |

TABLE 17b-continued

Formula XVIIIb

| R⁷ | R¹¹ | R¹ᵇ' | R¹ᵇ" |
|---|---|---|---|
| 4-hydroxyphenyl | benzyl | —OH | F |
| cyclohexyl | 3-hydroxybenzyl | OH | OH |
| benzyl | 3-methoxybenzyl | —NH₂ | H |

TABLE 17c

Formula XVIIIc

| R⁷ | R¹¹ | R¹ᵇ' | R¹ᵇ" |
|---|---|---|---|
| H | H | H | H |
| Me | H | H | OH |
| 4-methylphenyl | phenyl | F | H |

TABLE 17c-continued

Formula XVIIIc

| R⁷ | R¹¹ | R¹ᵇ' | R¹ᵇ" |
|---|---|---|---|
| 4-hydroxyphenyl | benzyl | —OH | F |
| cyclohexyl | 3-hydroxybenzyl | OH | OH |
| benzyl | 3-methoxybenzyl | —NH₂ | H |

TABLE 18

Formula XIX

| R1 | R2 | R1 | R2 |
|---|---|---|---|
| H | H | | |
| 4-hydroxyphenyl | benzyl | | |
| Me | H | cyclohexyl | 3-hydroxybenzyl |

TABLE 18-continued

Formula XIX

| R1 | R2 | R1 | R2 |
|---|---|---|---|
| 4-methylphenyl | phenyl | benzyl (CH2-phenyl) | 3-methoxybenzyl |

TABLE 18a

Formula XIXa

| R7 | R11c | R7 | R11c |
|---|---|---|---|
| H | H | 4-hydroxyphenyl | benzyl (CH2-phenyl) |
| Me | H | cyclohexyl | 3-hydroxybenzyl |
| 4-methylphenyl | phenyl | benzyl (CH2-phenyl) | 3-methoxybenzyl |

TABLE 18b
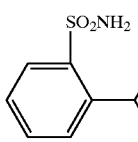
Formula XIXb
| R⁷ | R¹¹ | R⁷ | R¹¹ |
|---|---|---|---|
| H | H | 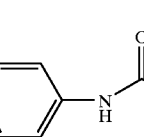 | 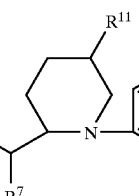 |
| Me | H | 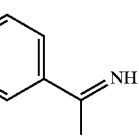 | 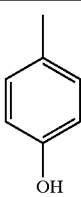 |
| 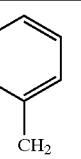 | 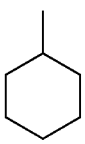 | 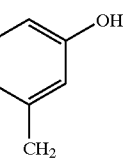 | 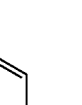 |
TABLE 18c
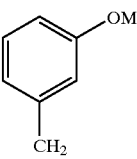
Formula XIXc
| R⁷ | R¹¹ᶜ | R⁷ | R¹¹ᶜ |
|---|---|---|---|
| H | H | 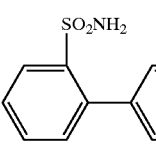 | 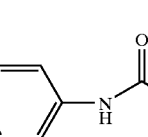 |
| Me | H | 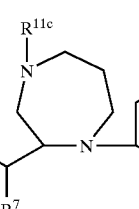 | 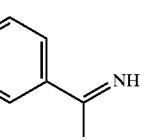 |

TABLE 18c-continued

Formula XIXc

| R[7] | R[11c] | R[7] | R[11c] |
|---|---|---|---|
| 4-methylphenyl | phenyl | benzyl (CH₂-phenyl) | 3-methoxybenzyl |

TABLE 19

Formula XX

| R[7] | R[11] | R[7] | R[11] |
|---|---|---|---|
| H | H | 4-hydroxyphenyl | benzyl |
| Me | H | cyclohexylmethyl | 3-hydroxybenzyl |
| 4-methylphenyl | phenyl | benzyl | 3-methoxybenzyl |

TABLE 19a

Formula XXa

| R⁷ | R¹¹ᶜ | R⁷ | R¹¹ᶜ |
|---|---|---|---|
| H | H | 4-hydroxyphenyl | benzyl (CH₂-phenyl) |
| Me | H | cyclohexyl | 3-hydroxybenzyl |
| 4-methylphenyl | phenyl | benzyl (CH₂-phenyl) | 3-methoxybenzyl |

TABLE 19b

Formula XXb

| R⁷ | R¹¹ | R⁷ | R¹¹ |
|---|---|---|---|
| H | H | 4-hydroxyphenyl | benzyl (CH₂-phenyl) |
| Me | H | cyclohexyl | 3-hydroxybenzyl |

TABLE 19b-continued
Formula XXb
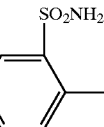
| R[7] | R[11] | R[7] | R[11] |
|---|---|---|---|
|  | 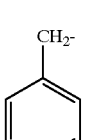 | 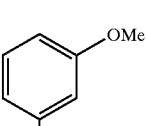 | 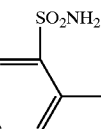 |
TABLE 19c
Formula XXc
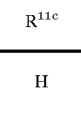
| R[7] | R[11c] | R[7] | R[11c] |
|---|---|---|---|
| H | H | 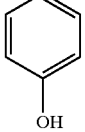 | 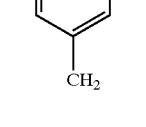 |
| Me | H | 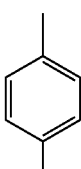 | 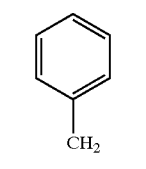 |
| 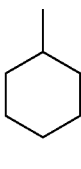 | 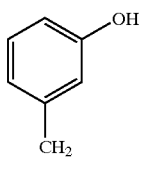 | 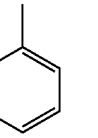 | 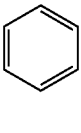 |

TABLE 20
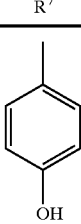
Formula XXI
| R⁷ | R¹¹ | R⁷ | R¹¹ |
|---|---|---|---|
| H | H | 4-hydroxyphenyl | benzyl (CH₂-Ph) |
| Me | H | cyclohexyl | 3-hydroxybenzyl |
| 2-methylphenyl | phenyl | benzyl | 3-methoxybenzyl |
TABLE 21
Formula XXII
| R⁷ | R¹¹ | R⁷ | R¹¹ |
|---|---|---|---|
| H | H | 4-hydroxyphenyl | benzyl |
| Me | H | cyclohexyl | 3-hydroxybenzyl |

TABLE 21-continued

Formula XXII

| R⁷ | R¹¹ | R⁷ | R¹¹ |
|---|---|---|---|
| (phenyl) | (phenyl) | CH₂-phenyl | 3-OMe-phenyl-CH₂ |

TABLE 20a

Formula XXIa

| R⁷ | R¹¹ᶜ | R⁷ | R¹¹ᶜ |
|---|---|---|---|
| H | H | 4-OH-phenyl | phenyl-CH₂ |
| Me | H | cyclohexyl | 3-OH-phenyl-CH₂ |
| (methyl) | phenyl | CH₂-phenyl | 3-OMe-phenyl-CH₂ |

TABLE 21a

Formula XXIIa

| R⁷ | R¹¹ᶜ | R⁷ | R¹¹ᶜ |
|---|---|---|---|
| H | H | 4-OH-phenyl | phenyl-CH₂ |
| Me | H | cyclohexyl | 3-OH-phenyl-CH₂ |
| (methyl) | phenyl | CH₂-phenyl | 3-OMe-phenyl-CH₂ |

TABLE 20b
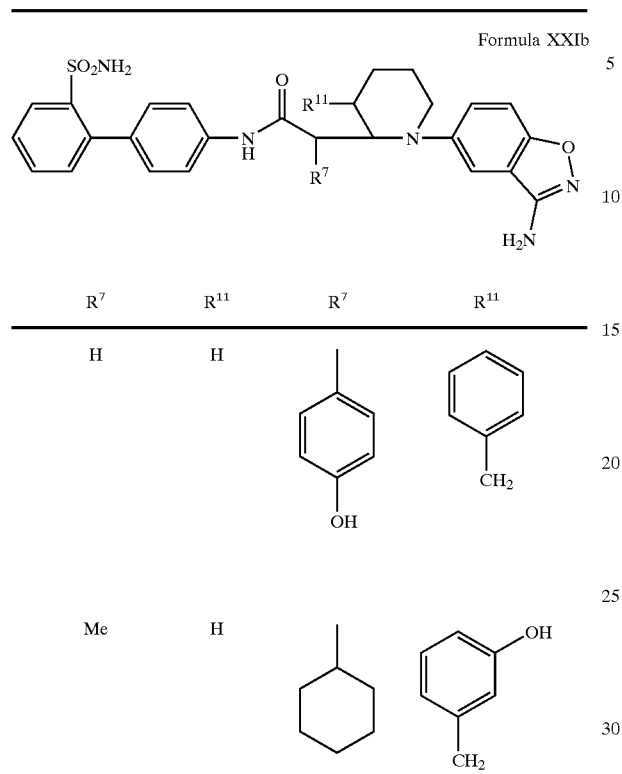
TABLE 21b
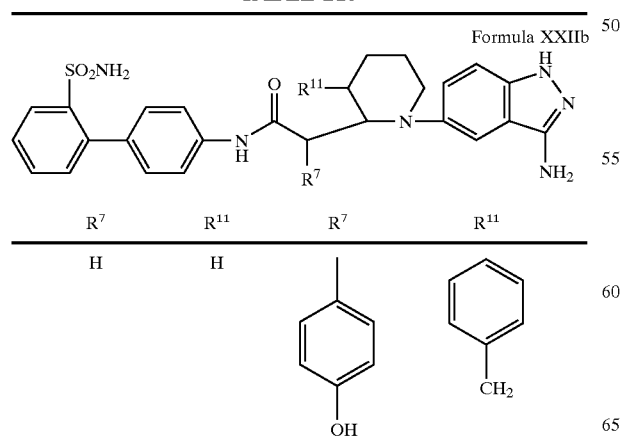
TABLE 21b-continued
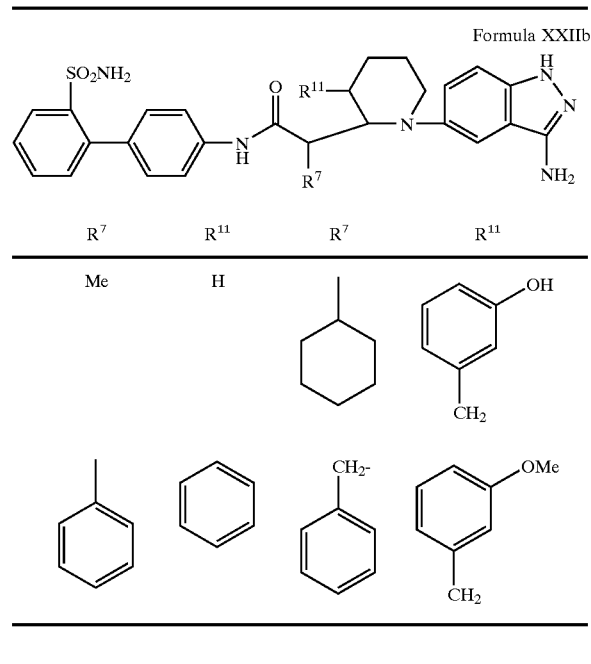
TABLE 20c
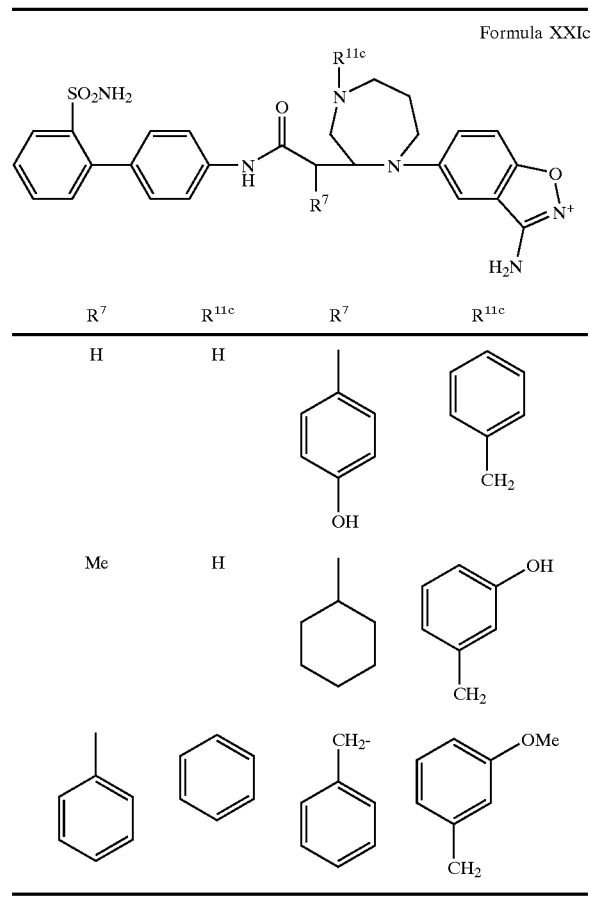

TABLE 21c
Formula XXIIc
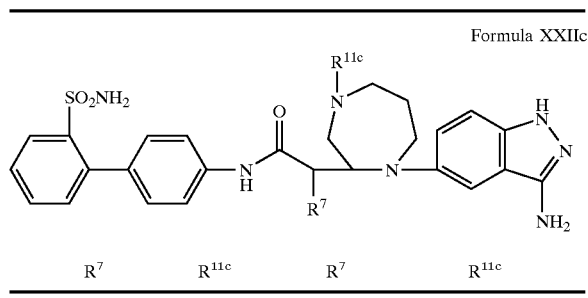
| R[7] | R[11c] | R[7] | R[11c] |
|---|---|---|---|
| H | H | 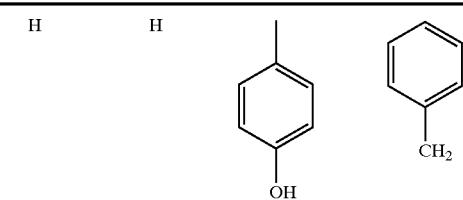 | |
| Me | H | 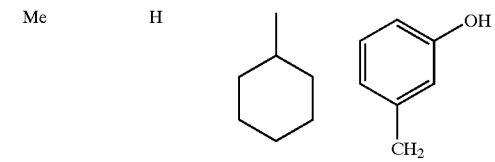 | |
| 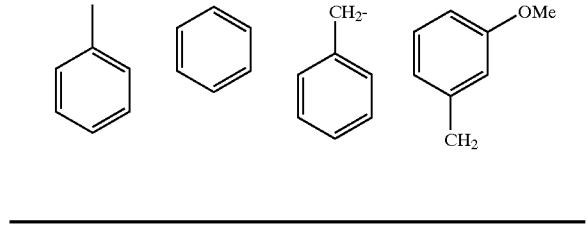 | | | |
TABLE 22
Formula XXIII
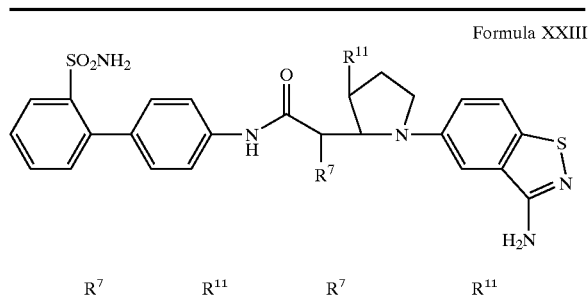
| R[7] | R[11] | R[7] | R[11] |
|---|---|---|---|
| H | H | 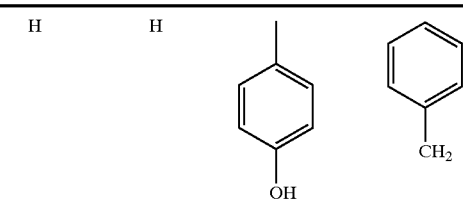 | |
TABLE 22-continued
Formula XXIII
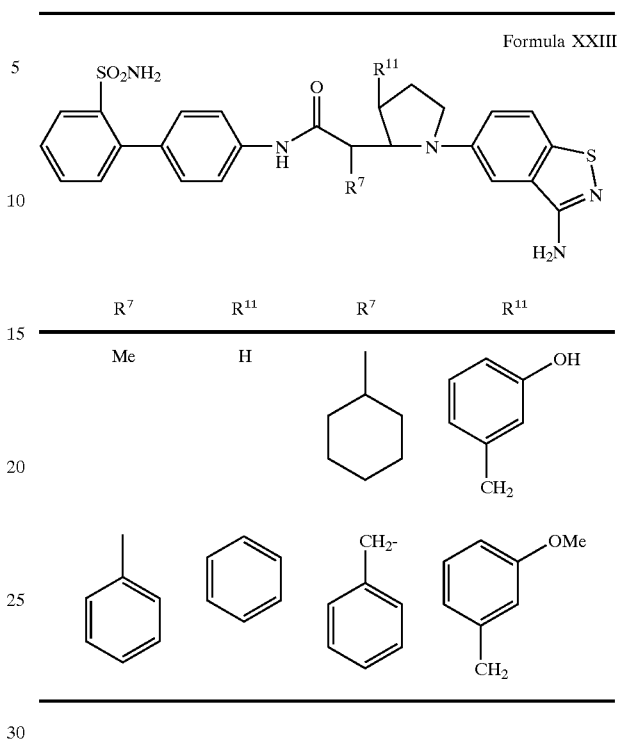
| R[7] | R[11] | R[7] | R[11] |
|---|---|---|---|
| Me | H | 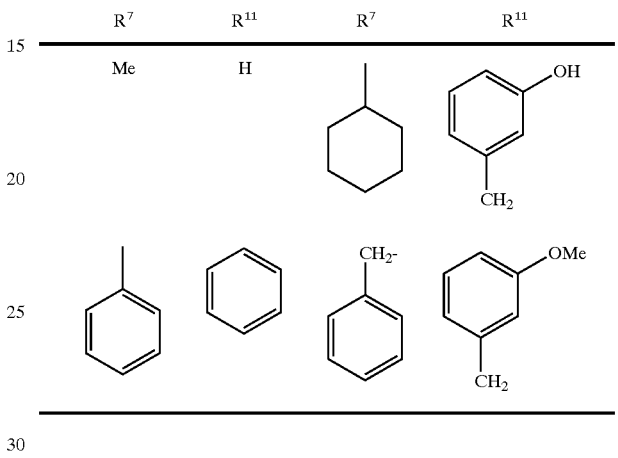 | |
| 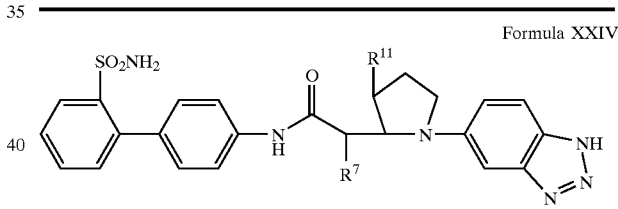 | | | |
TABLE 23
Formula XXIV
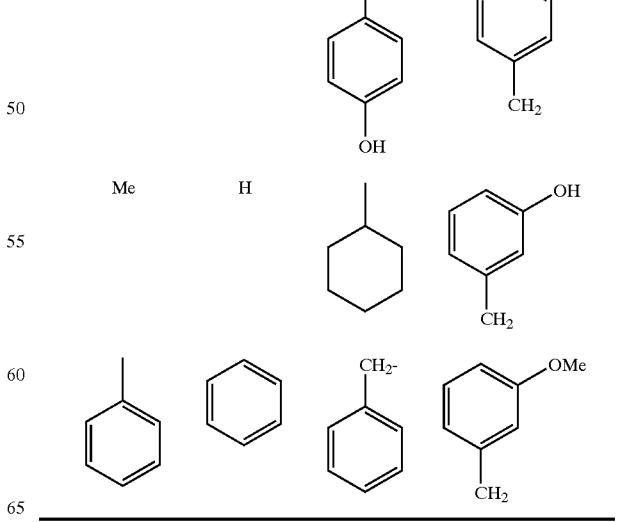
| R[7] | R[11] | R[7] | R[11] |
|---|---|---|---|
| H | H | | |
| Me | H | | |

TABLE 22a

Formula XXIIIa

| $R^7$ | $R^{11c}$ | $R^7$ | $R^{11c}$ |
|---|---|---|---|
| H | H | 4-hydroxyphenyl | benzyl |
| Me | H | cyclohexyl | 3-hydroxyphenyl |
| 4-methylphenyl | phenyl | benzyl | 3-methoxyphenyl |

TABLE 23a

Formula XXIVa

| $R^7$ | $R^{11c}$ | $R^7$ | $R^{11c}$ |
|---|---|---|---|
| H | H | 4-hydroxyphenyl | benzyl |
| Me | H | cyclohexyl | 3-hydroxyphenyl |

TABLE 23a-continued

Formula XXIVa

| $R^7$ | $R^{11c}$ | $R^7$ | $R^{11c}$ |
|---|---|---|---|
| 4-methylphenyl | phenyl | benzyl | 3-methoxyphenyl |

TABLE 22b

Formula XXIIIb

| $R^7$ | $R^{11}$ | $R^7$ | $R^{11}$ |
|---|---|---|---|
| H | H | 4-hydroxyphenyl | benzyl |
| Me | H | cyclohexyl | 3-hydroxyphenyl |
| 4-methylphenyl | phenyl | benzyl | 3-methoxyphenyl |

TABLE 23b
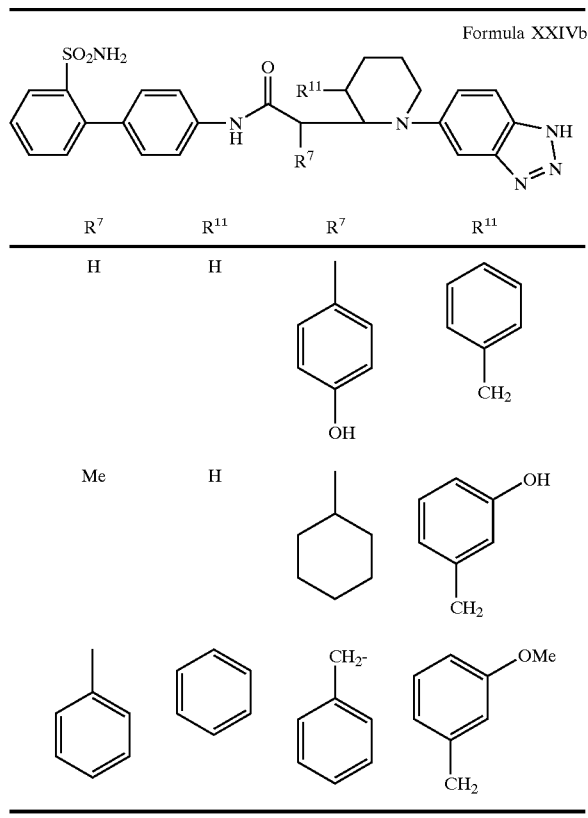
TABLE 22c
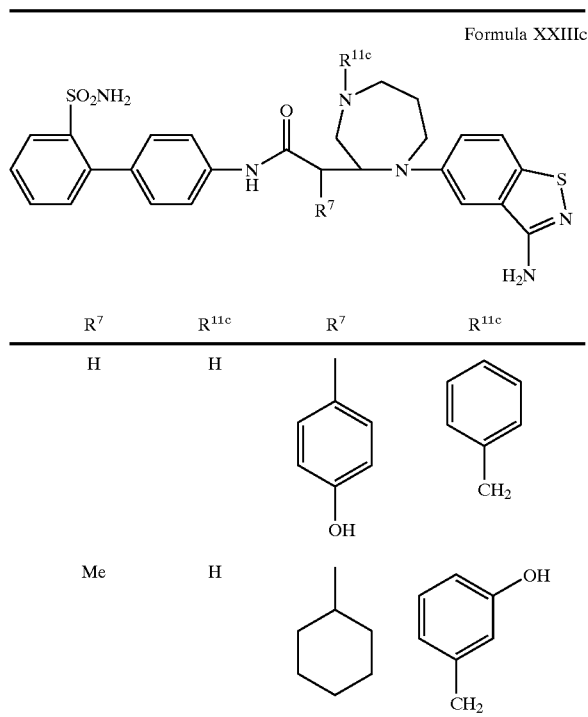
TABLE 22c-continued
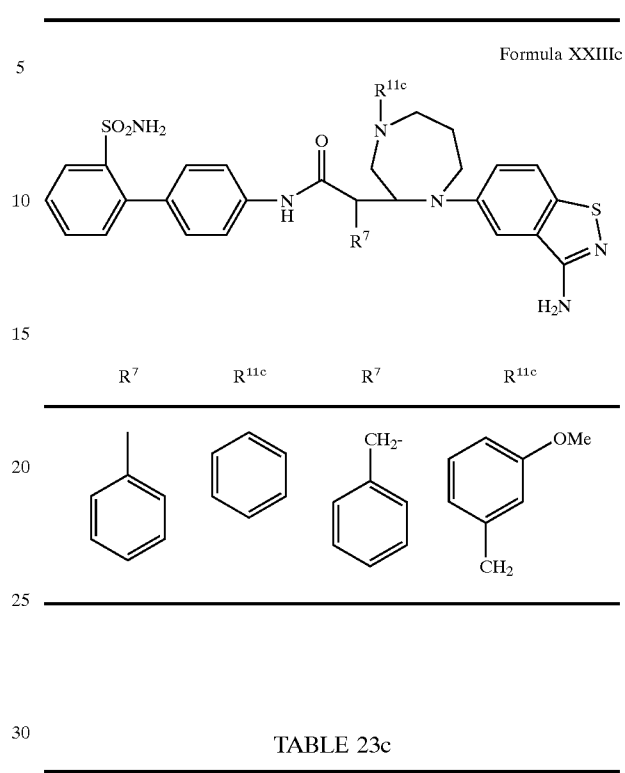
TABLE 23c
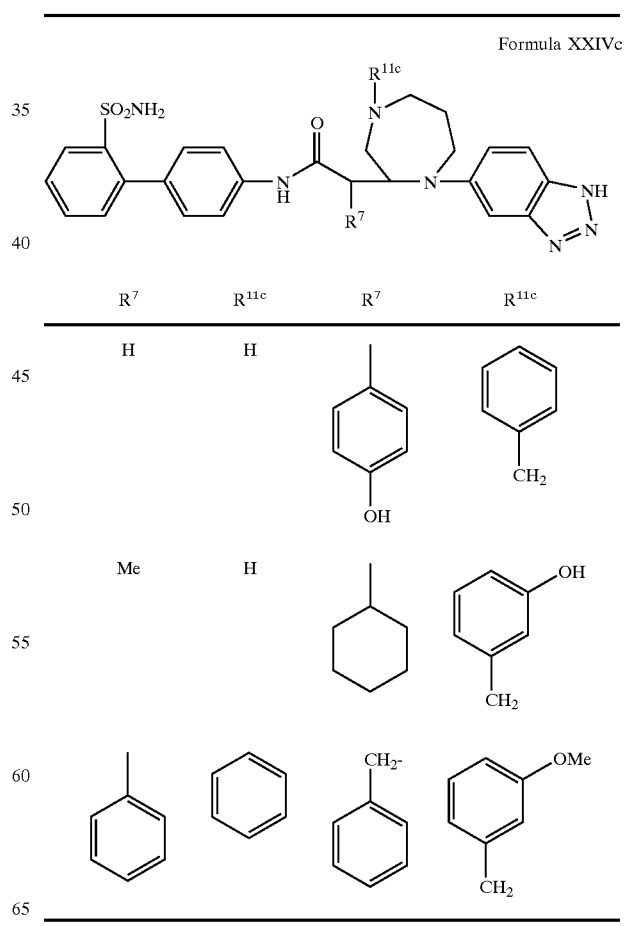

TABLE 24
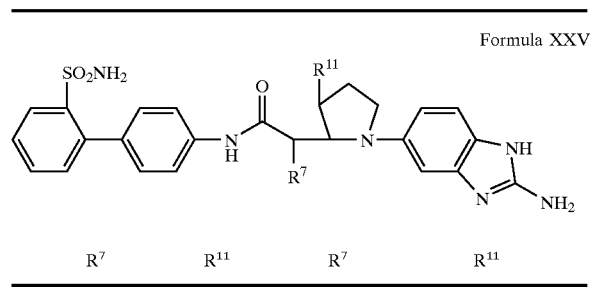
Formula XXV
| R⁷ | R¹¹ | R⁷ | R¹¹ |
|---|---|---|---|
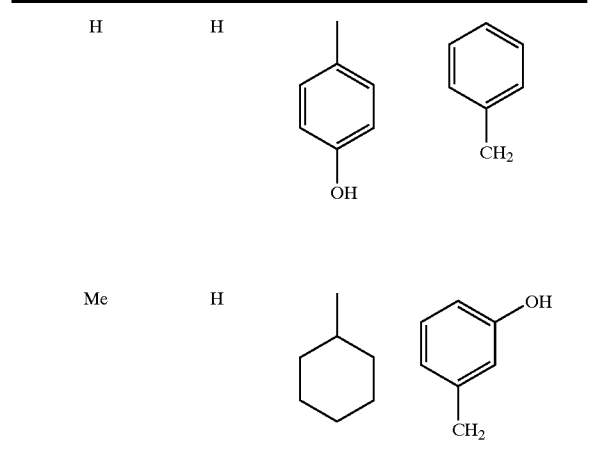
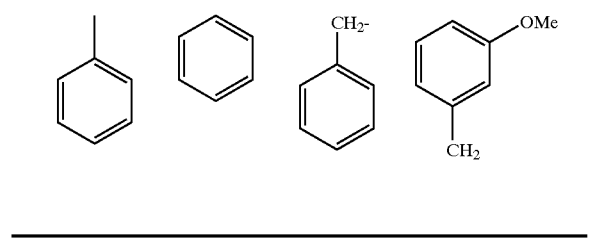
TABLE 24a
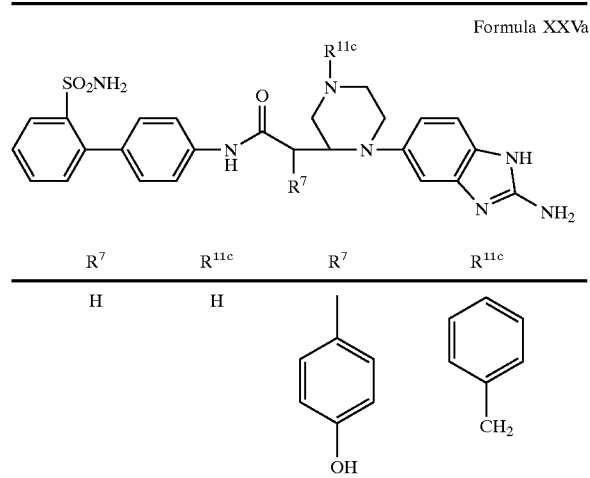
Formula XXVa
| R⁷ | R¹¹ᶜ | R⁷ | R¹¹ᶜ |
|---|---|---|---|
TABLE 24a-continued
Formula XXVa
| R⁷ | R¹¹ᶜ | R⁷ | R¹¹ᶜ |
|---|---|---|---|
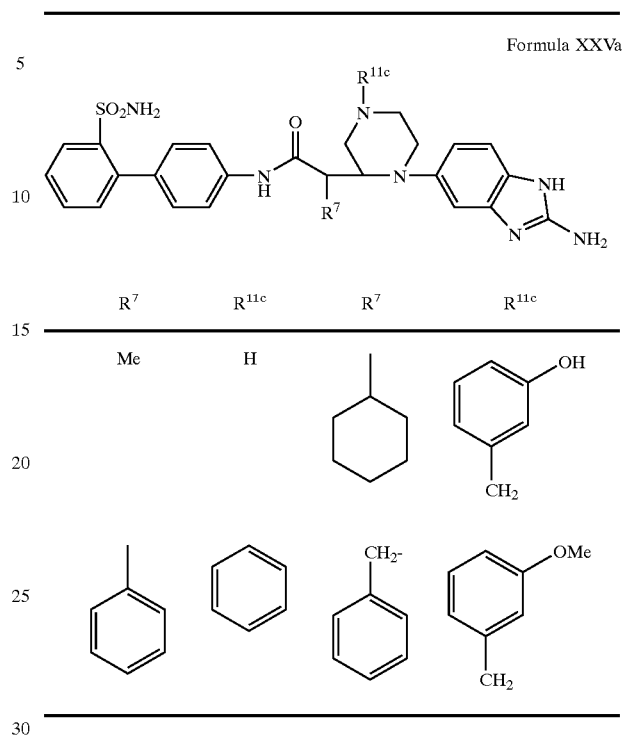
TABLE 24b
Formula XXVb
| R⁷ | R¹¹ | R⁷ | R¹¹ |
|---|---|---|---|
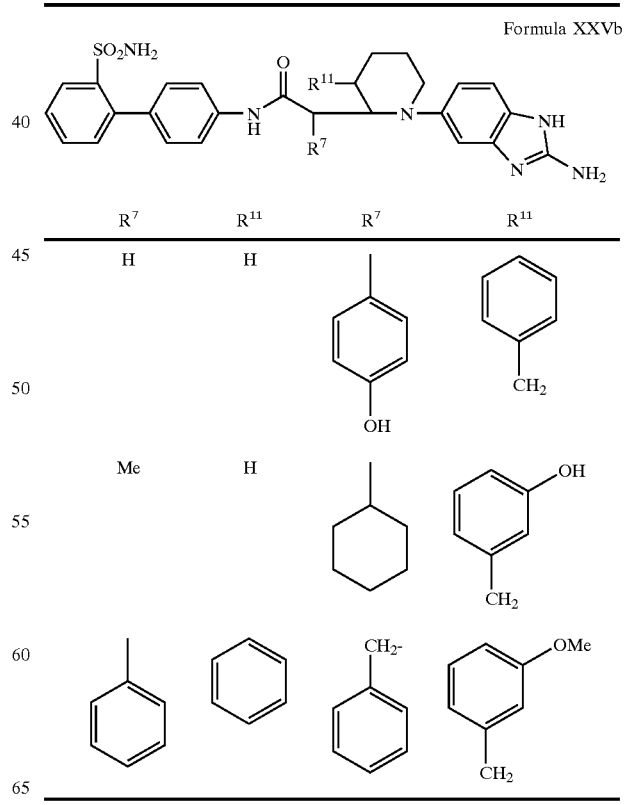

TABLE 24c

Formula XXVc

| $R^7$ | $R^{11c}$ | $R^7$ | $R^{11c}$ |
|---|---|---|---|
| H | H | 4-hydroxyphenyl | benzyl |
| Me | H | cyclohexyl | 3-hydroxyphenylmethyl |
| 4-methylphenyl | phenyl | benzyl | 3-methoxyphenylmethyl |

TABLE 29c

Formula XXXc

| $R^{11}$ | $R^{11c}$ | $R^{11}$ | $R^{11c}$ |
|---|---|---|---|
| H | H | 4-hydroxyphenyl | benzyl |

TABLE 29c-continued

Formula XXXc

| $R^{11}$ | $R^{11c}$ | $R^{11}$ | $R^{11c}$ |
|---|---|---|---|
| Me | H | cyclohexyl | 3-hydroxyphenylmethyl |
| 4-methylphenyl | phenyl | benzyl | 3-methoxyphenylmethyl |

TABLE 26

Formula XXVI

| $R^{11'}$ | $R^{11''}$ | $R^{11'}$ | $R^{11''}$ |
|---|---|---|---|
| H | H | 4-hydroxyphenyl | benzyl |
| Me | H | cyclohexyl | 3-hydroxyphenylmethyl |
| 4-methylphenyl | phenyl | benzyl | 3-methoxyphenylmethyl |

TABLE 25a
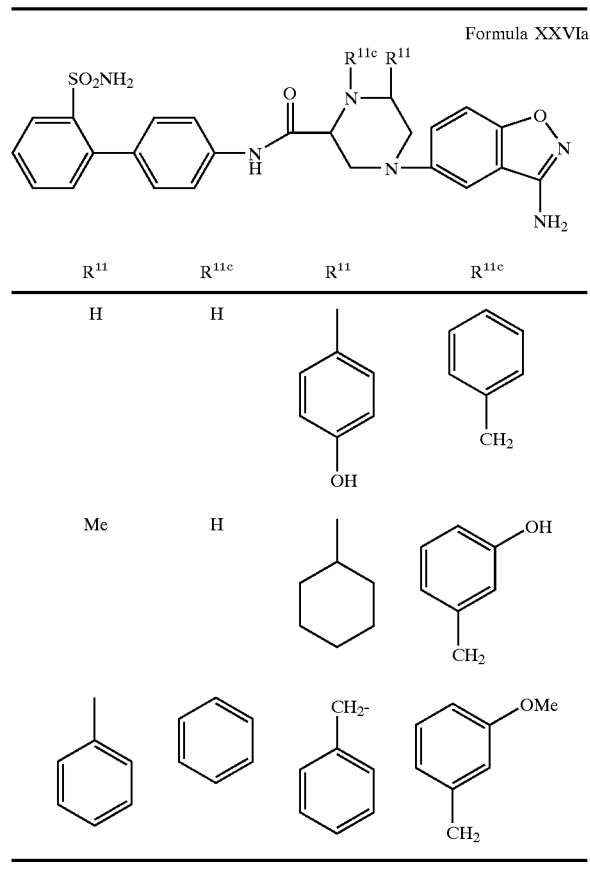
TABLE 26a
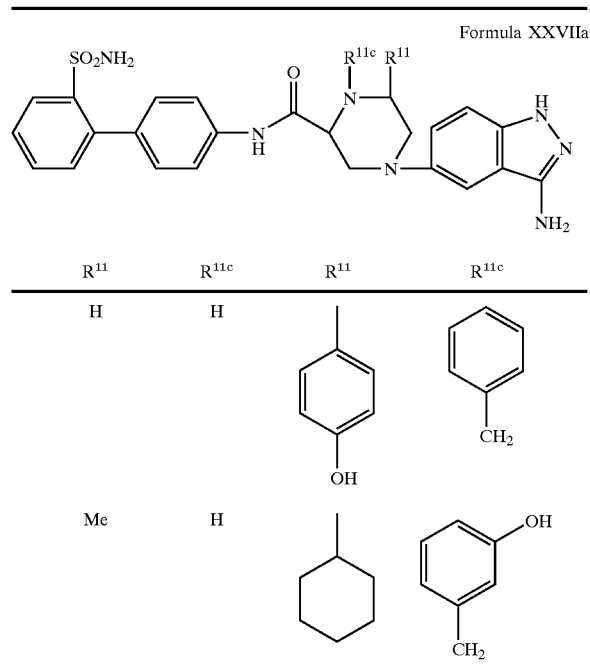
TABLE 26a-continued
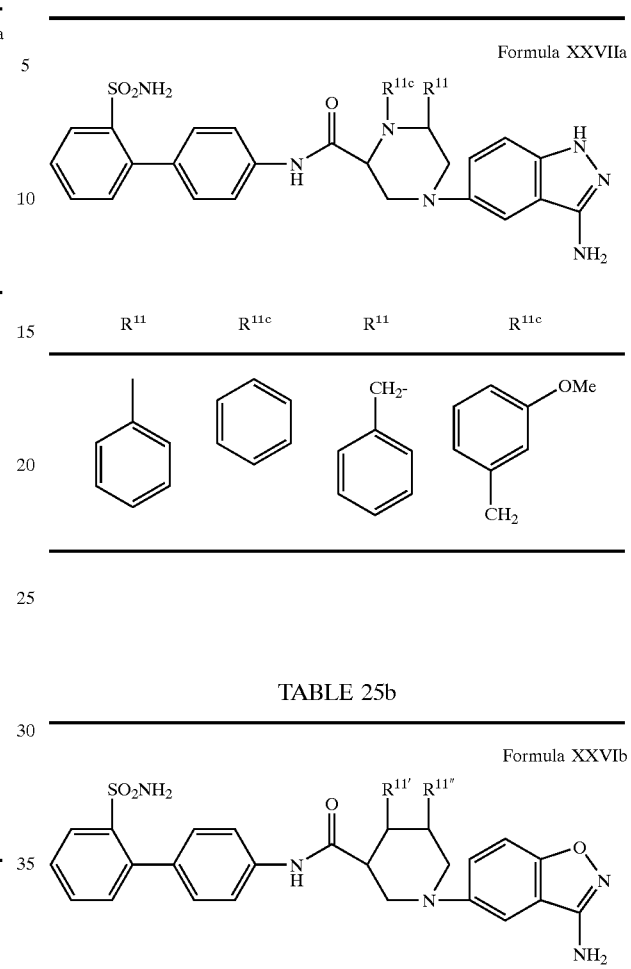
TABLE 25b
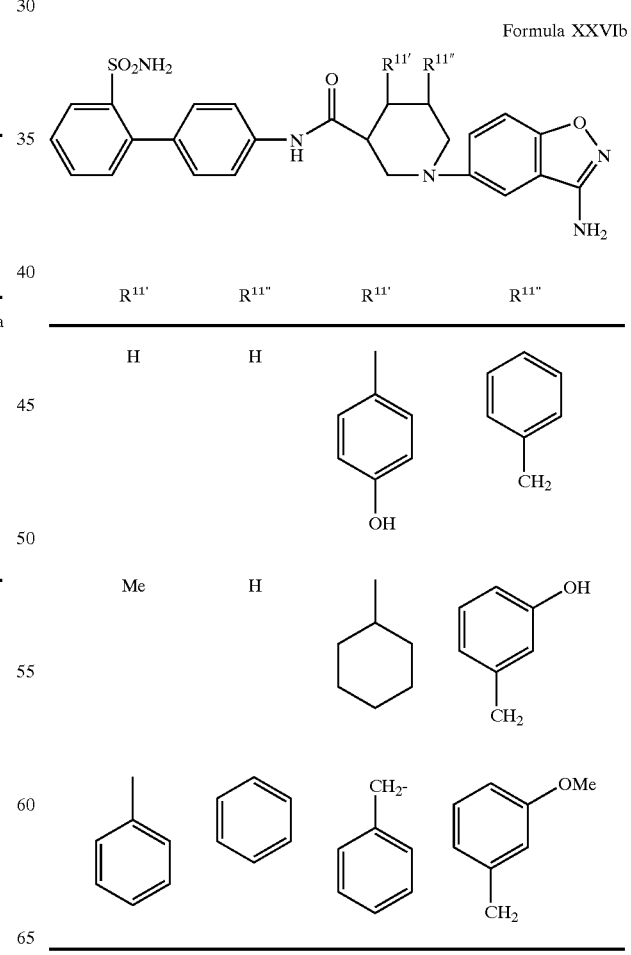

TABLE 26b
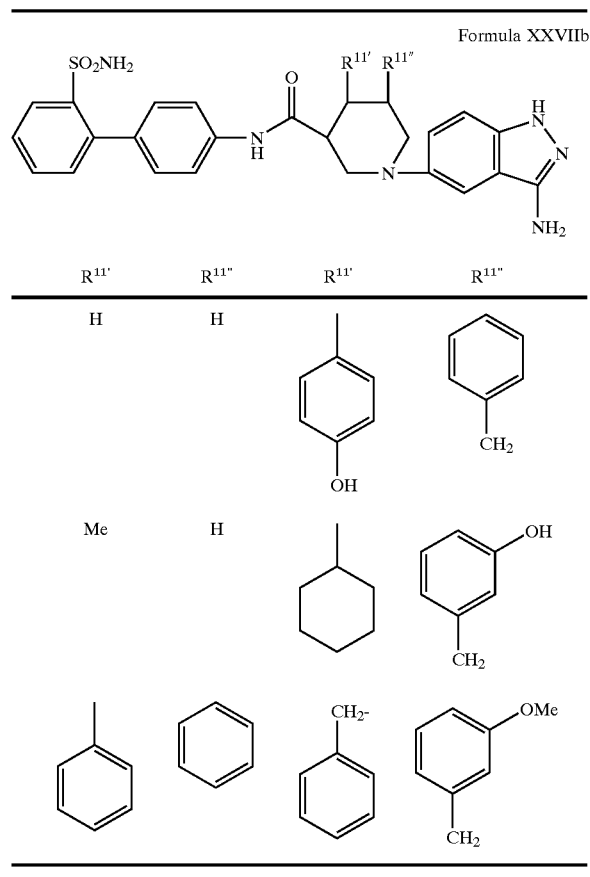
TABLE 25c
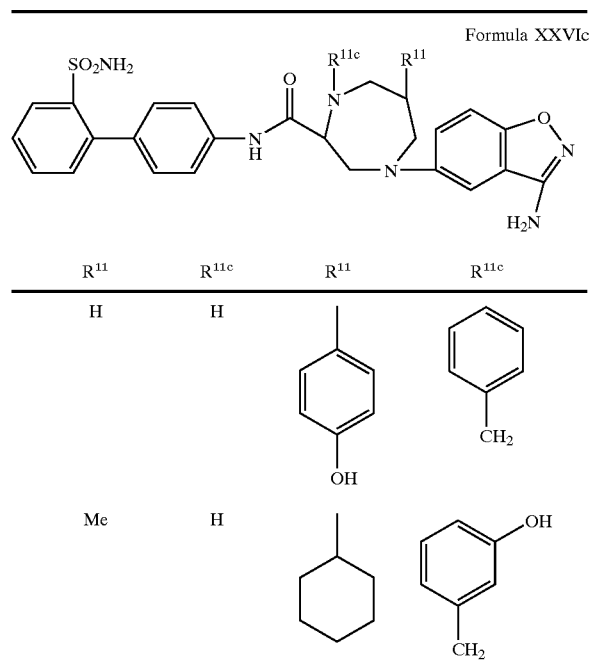
TABLE 25c-continued
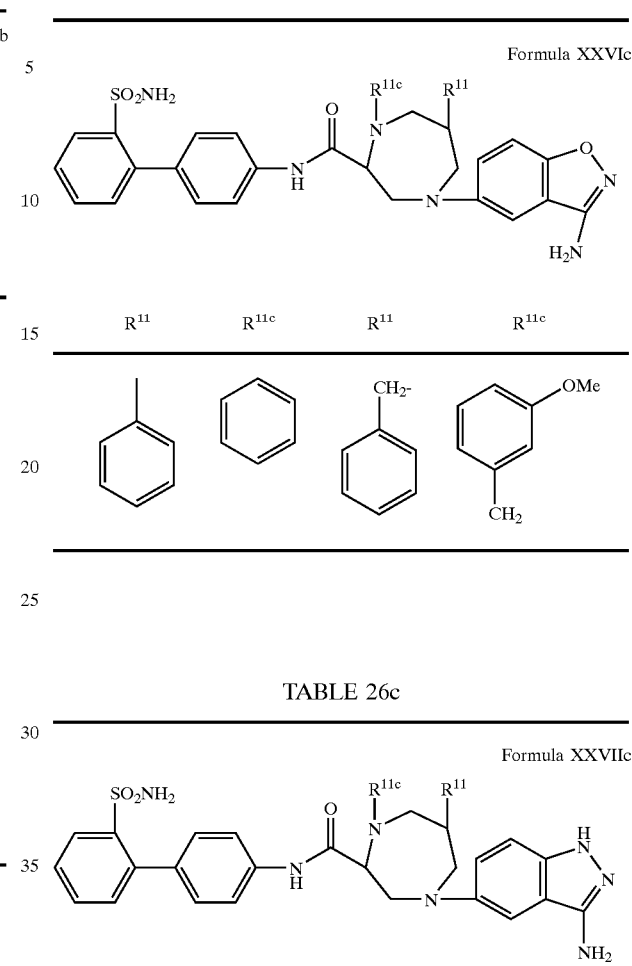
TABLE 26c
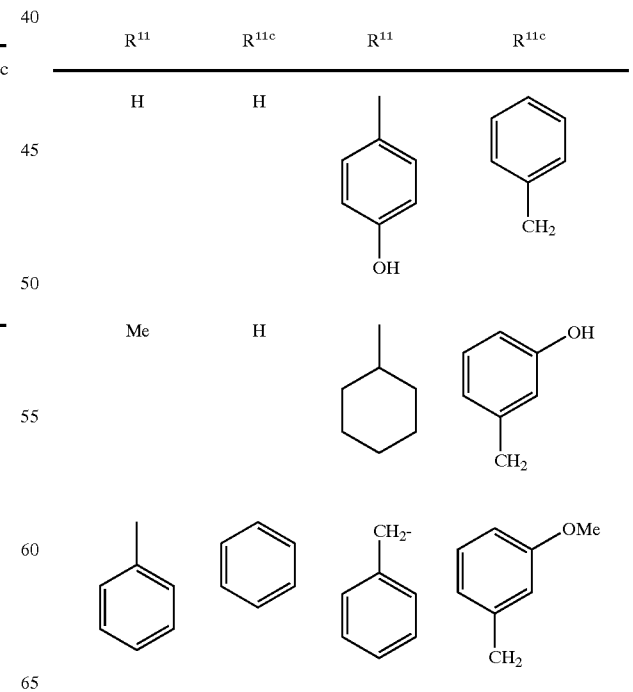

TABLE 27

Formula XXVII

| $R^{11'}$ | $R^{11''}$ | $R^{11'}$ | $R^{11''}$ |
|---|---|---|---|
| H | H | 4-hydroxyphenyl | benzyl |
| Me | H | cyclohexyl | 3-hydroxybenzyl |
| 4-methylphenyl | phenyl | benzyl | 3-methoxybenzyl |

TABLE 28

Formula XXIX

| $R^{11'}$ | $R^{11''}$ | $R^{11'}$ | $R^{11''}$ |
|---|---|---|---|
| H | H | 4-hydroxyphenyl | benzyl |

TABLE 28-continued

Formula XXIX

| $R^{11'}$ | $R^{11''}$ | $R^{11'}$ | $R^{11''}$ |
|---|---|---|---|
| Me | H | cyclohexyl | 3-hydroxybenzyl |
| 4-methylphenyl | phenyl | benzyl | 3-methoxybenzyl |

TABLE 27a

Formula XXVIIIa

| $R^{11}$ | $R^{11c}$ | $R^{11}$ | $R^{11c}$ |
|---|---|---|---|
| H | H | 4-hydroxyphenyl | benzyl |
| Me | H | cyclohexyl | 3-hydroxybenzyl |
| 4-methylphenyl | phenyl | benzyl | 3-methoxybenzyl |

TABLE 28a

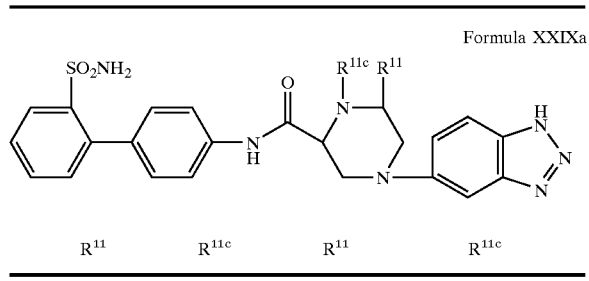

Formula XXIXa

| R[11] | R[11c] | R[11] | R[11c] |
|---|---|---|---|
| H | H | 4-hydroxyphenyl | benzyl |
| Me | H | cyclohexyl | 3-hydroxybenzyl |
| 4-methylphenyl | phenyl | benzyl | 3-methoxybenzyl |

TABLE 27b

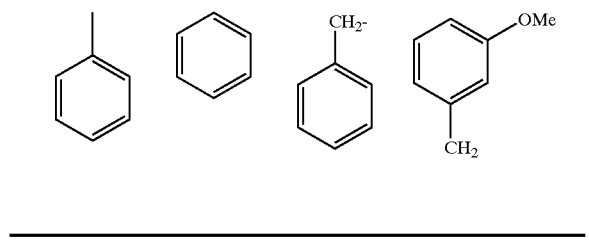

Formula XXVIIIb

| R[11'] | R[11''] | R[11'] | R[11''] |
|---|---|---|---|
| H | H | 4-hydroxyphenyl | benzyl |

TABLE 27b-continued

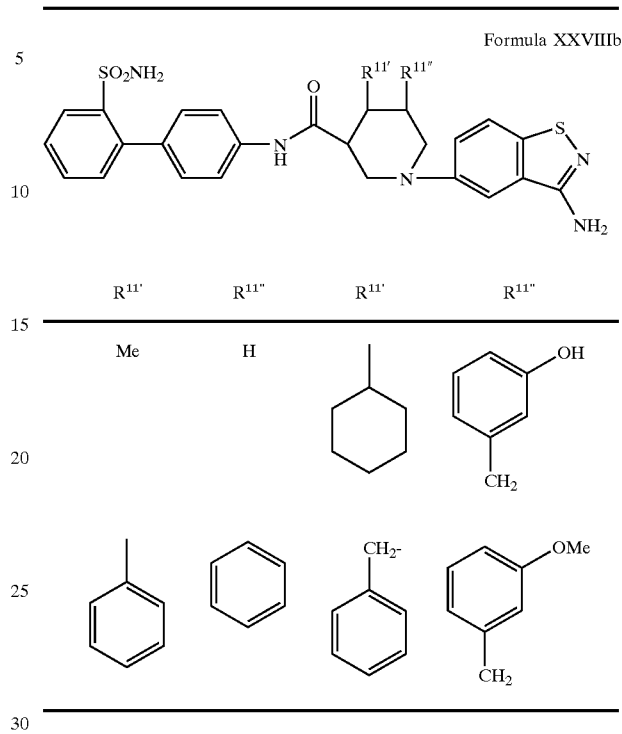

Formula XXVIIIb

| R[11'] | R[11''] | R[11'] | R[11''] |
|---|---|---|---|
| Me | H | cyclohexyl | 3-hydroxybenzyl |
| 4-methylphenyl | phenyl | benzyl | 3-methoxybenzyl |

TABLE 28b

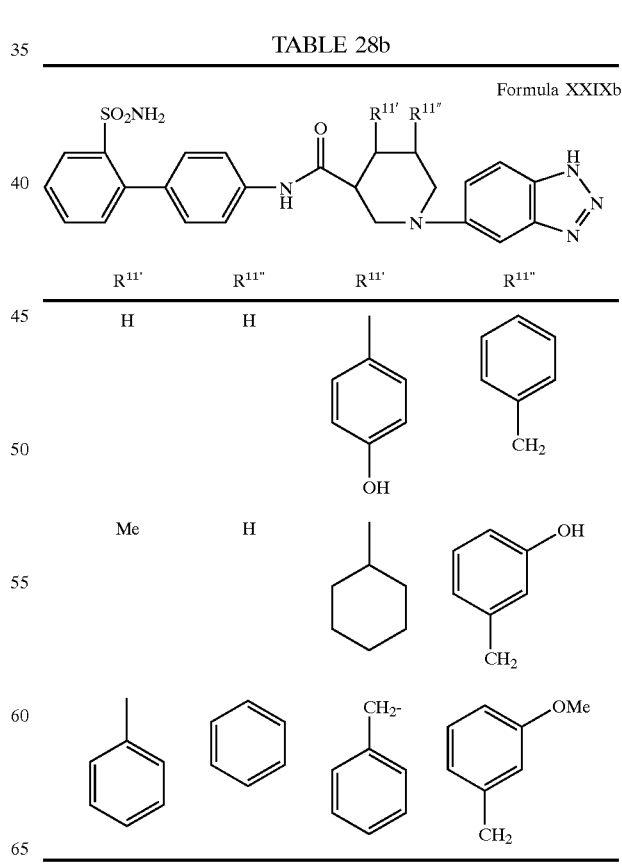

Formula XXIXb

| R[11'] | R[11''] | R[11'] | R[11''] |
|---|---|---|---|
| H | H | 4-hydroxyphenyl | benzyl |
| Me | H | cyclohexyl | 3-hydroxybenzyl |
| 4-methylphenyl | phenyl | benzyl | 3-methoxybenzyl |

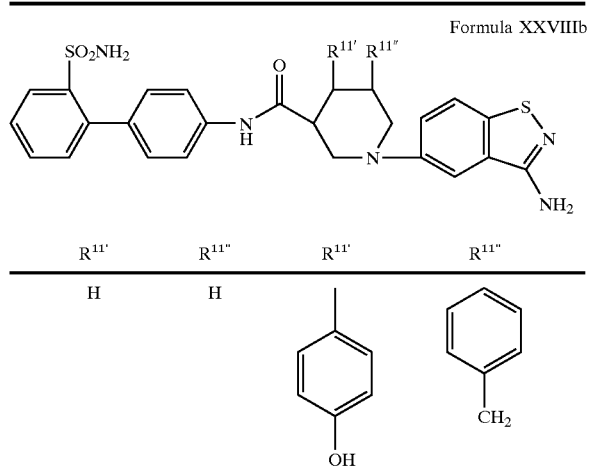

TABLE 27c
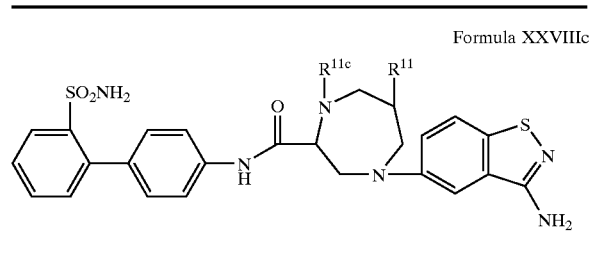
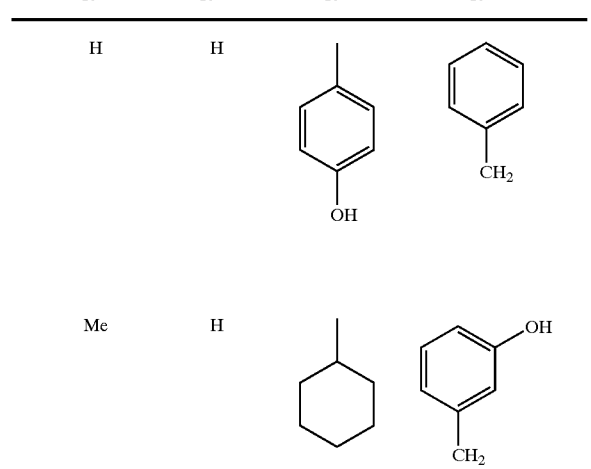
TABLE 28c
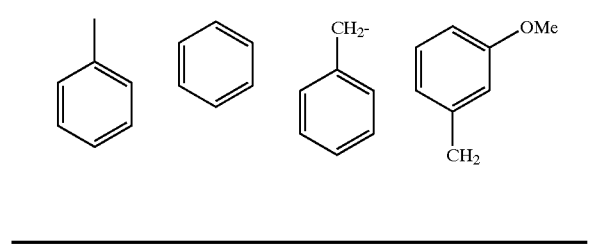
TABLE 28c-continued
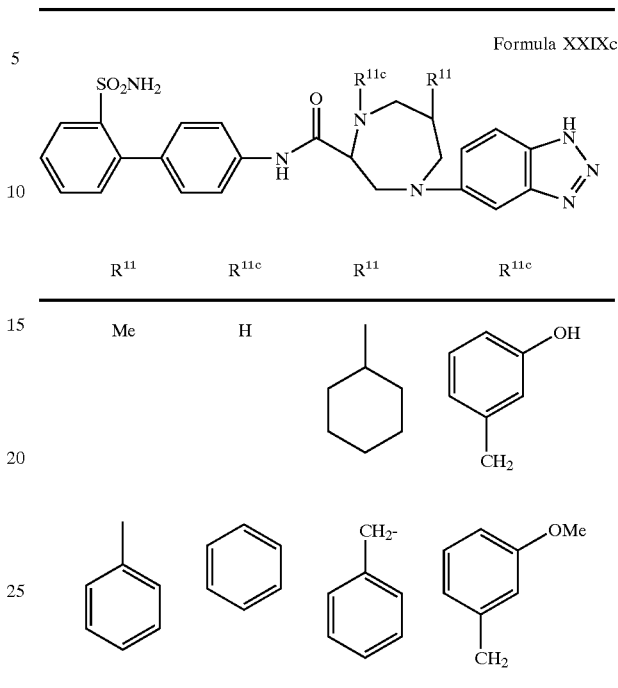
TABLE 29
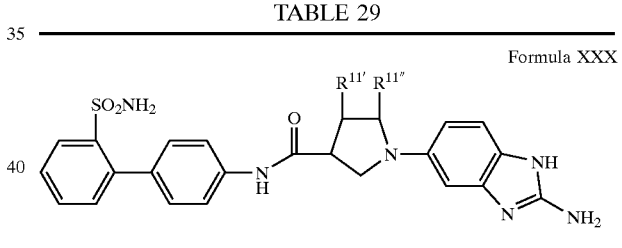
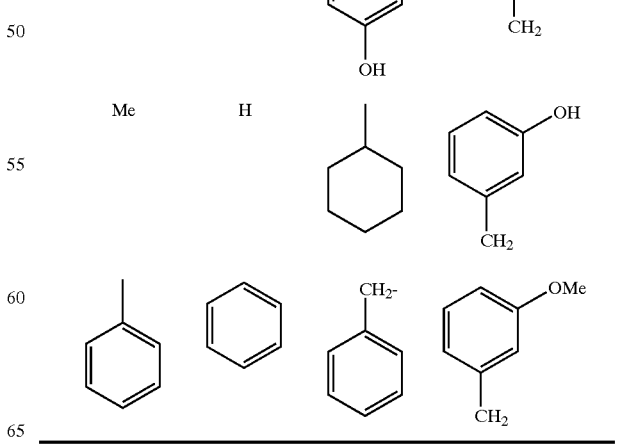

TABLE 29a

Formula XXXa

| $R^{11'}$ | $R^{11c}$ | $R^{11'}$ | $R^{11c}$ |
|---|---|---|---|
| H | H | 4-hydroxyphenyl | phenyl-CH2 |
| Me | H | cyclohexyl | 3-hydroxyphenyl-CH2 |
| 4-methylphenyl | phenyl | phenyl-CH2- | 3-methoxyphenyl-CH2 |

TABLE 29b

Formula XXXb

| $R^{11'}$ | $R^{11''}$ | $R^{11'}$ | $R^{11''}$ |
|---|---|---|---|
| H | H | 4-hydroxyphenyl | phenyl-CH2 |
| Me | H | cyclohexyl | 3-hydroxyphenyl-CH2 |
| 4-methylphenyl | phenyl | phenyl-CH2- | 3-methoxyphenyl-CH2 |

TABLE 29c

Formula XXXc

| $R^{11}$ | $R^{11c}$ | $R^{11}$ | $R^{11c}$ |
|---|---|---|---|
| H | H | 4-hydroxyphenyl | phenyl-CH2 |
| Me | H | cyclohexyl | 3-hydroxyphenyl-CH2 |
| 4-methylphenyl | phenyl | phenyl-CH2- | 3-methoxyphenyl-CH2 |

Also preferred are compounds according to Tables 1 through Table 24c, wherein the following groups:

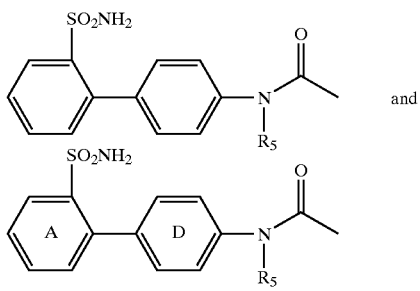

and when they occur in each of the formulae of the Tables are exchanged for a group having the carboxamide group in a reverse horizontal orientation as follows:

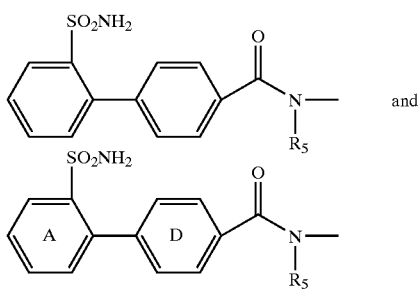

and wherein the $R_5$ substituent is the hydrogen or other amino substituent shown in the respective Tables 1 through 24c.

This invention also encompasses all pharmaceutically acceptable isomers, salts, hydrates and solvates of the compounds of formulas I, II and III. In addition, the compounds of formulas I, II and III can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif. 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilaniellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the finctional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Non-limiting exemplary synthesis schemes are outlined directly below, and specific steps are described in the Examples. The reaction products are isolated and purified by conventional methods, typically by solvent extraction into a compatible solvent. The products may be further purified by column chromatography or other appropriate methods.

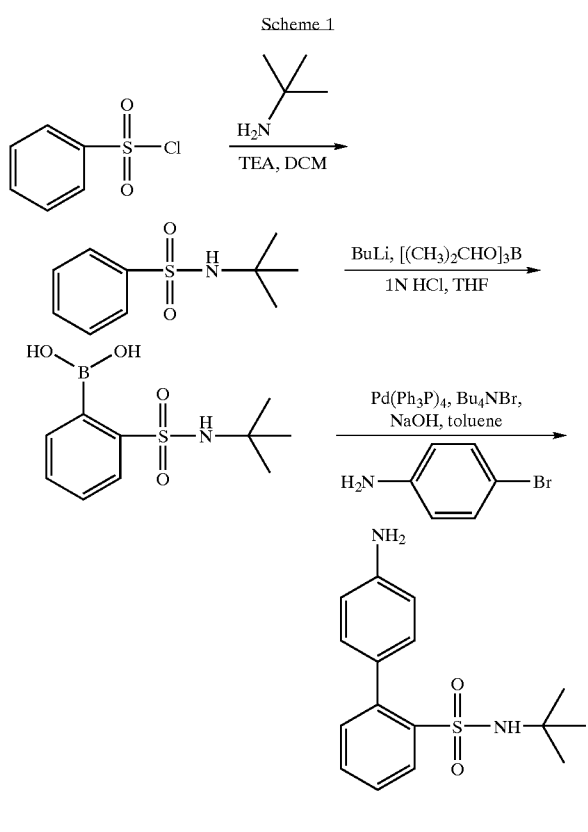

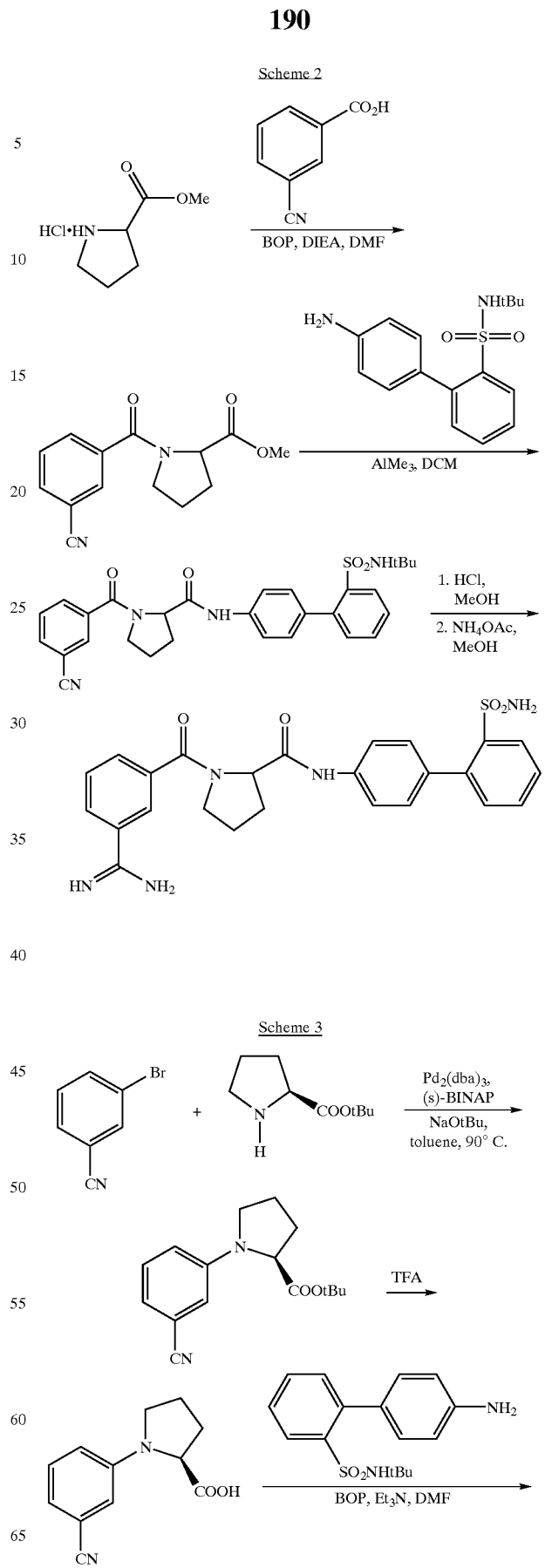

191
-continued
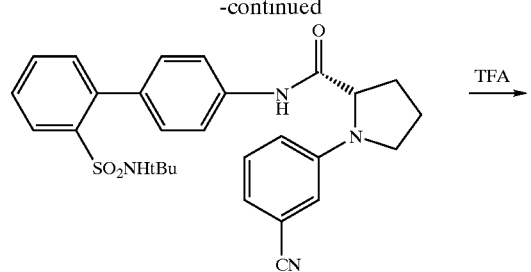
TFA →
192
-continued
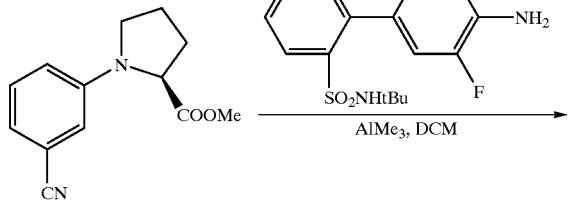
AlMe₃, DCM →
1. NH₂OH·HCl, Et₃N, ethanol, 40° C.
2. Ac₂O, AcOH
3. 50psi H₂, 10% Pd/C, methanol
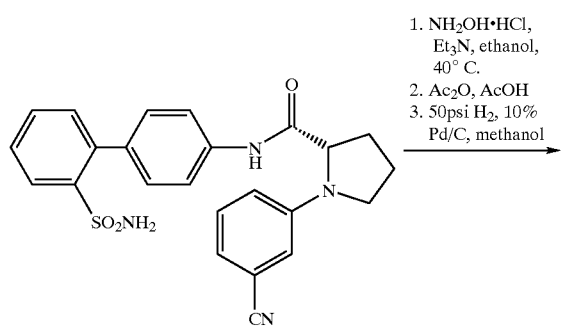
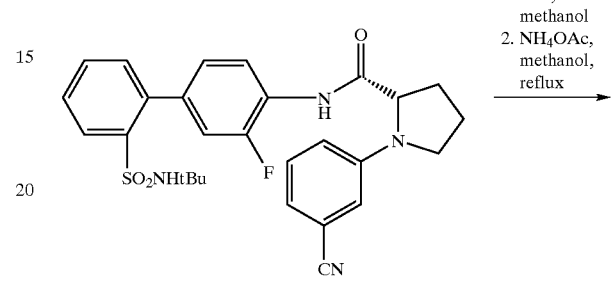
1. HCl, methanol
2. NH₄OAc, methanol, reflux
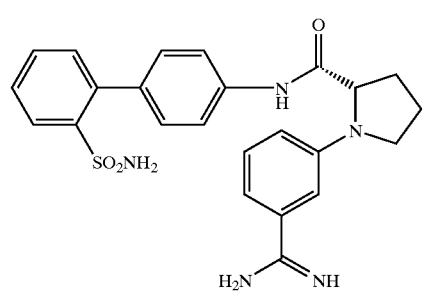
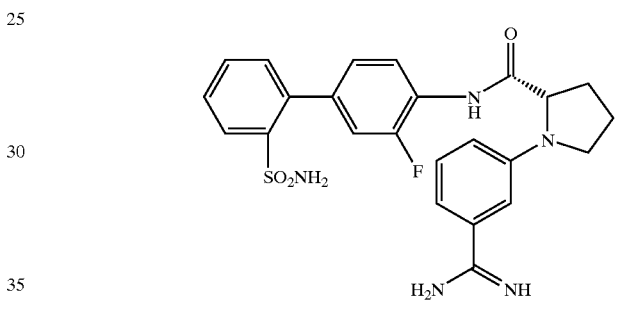
Scheme 4
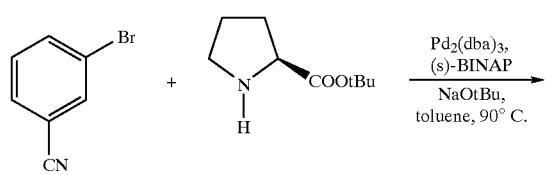
Pd₂(dba)₃, (s)-BINAP
NaOtBu, toluene, 90° C. →
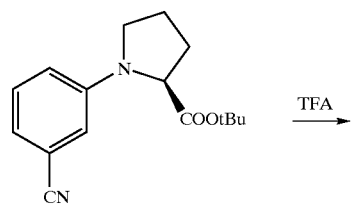
TFA →
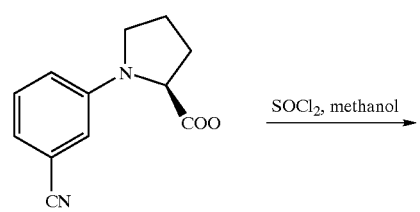
SOCl₂, methanol →
Scheme 5
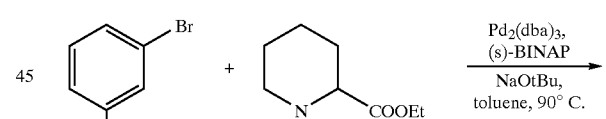
Pd₂(dba)₃, (s)-BINAP
NaOtBu, toluene, 90° C. →
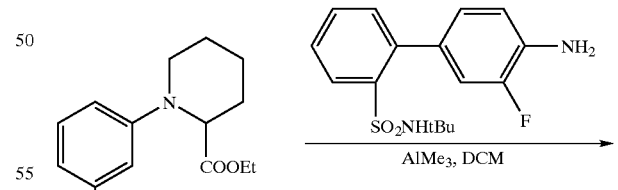
AlMe₃, DCM →
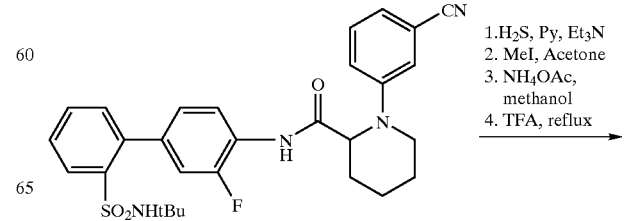
1. H₂S, Py, Et₃N
2. MeI, Acetone
3. NH₄OAc, methanol
4. TFA, reflux →

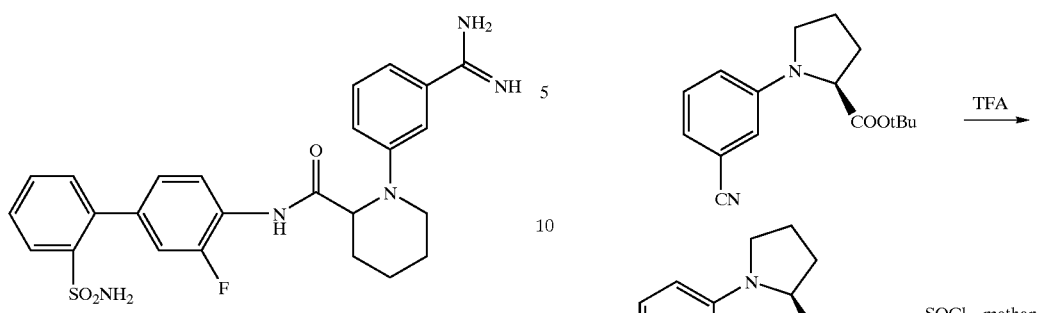
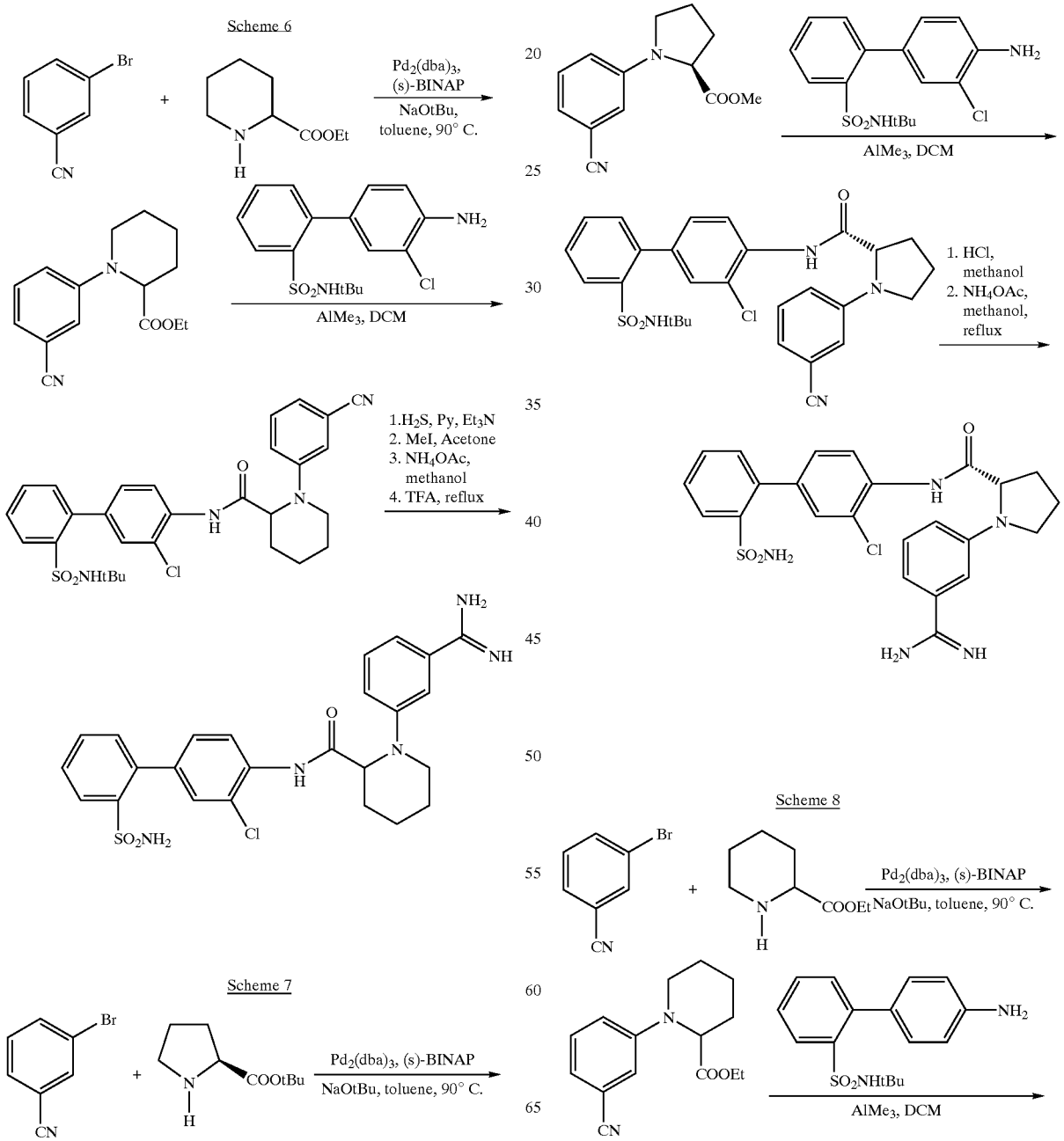

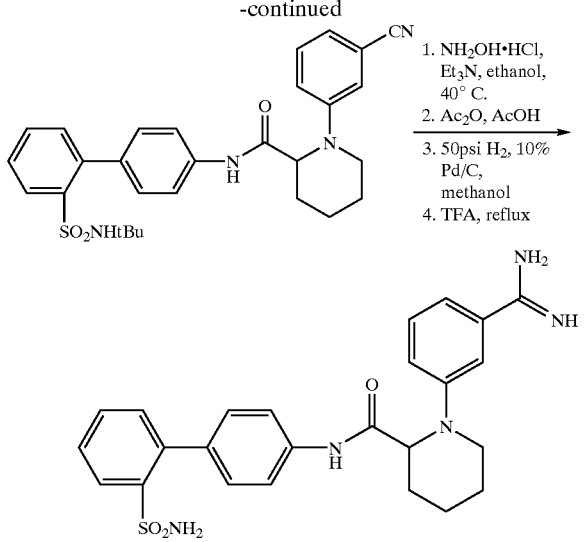

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutarnic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet finction, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without flurther description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

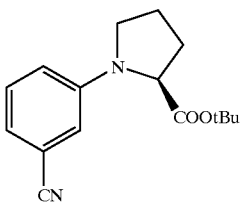

To a solution of 3-bromobenzonitrile (2.73 g, 15 mmol), H(L)-Proline-OtBu (5.14 g, 30 mmol), sodium tert-butoxide (2.02 g, 21 mmol) and (s)-(-)2,2'-bis(diphenylphosphino)-1,1'-binaphthyl (186 mg, 0.3 mmol) in toluene (30 ml) was added tris(dibenzylideneactone)dipalladium (0) (137 mg, 0.15 mmol). The mixture was stirred at 90° C. for 6 hrs. After the filtration of the solid, the filtrate was concentrated in vacuo. The residue was purified by silica gel column chromatography using solvent system 10% ethyl acetate in hexane as eluent to give the title compound as a light yellowish oil (336 mg, 82%). ES-MS (M+H)+=273.

Example 2

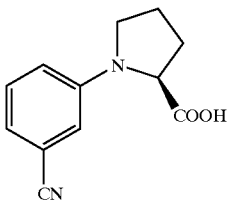

The compound of example 1 (1.4 g, 5.15 mmol) was dissolved in trifluoroacetic acid (5 ml). The mixture was stirred at room temperature for 5 hrs. The solvent was evaporated in vacuo to give the title compound (1.14 g, 100%). ES-MS (M+H)+=217.

Example 3

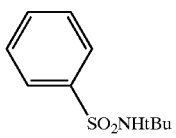

To a solution of tert-butylamine (5.73 g, 78.4 mmol) and triethylamine (16.6 ml, 119 mmol) in dichloromethane (200 ml) in an ice bath was added benzenesulfonyl chloride (13.85 g, 78.4 mmol) dropwise. The mixture was stirred at room temperature overnight. It was washed with saturated sodium carbonate (60 ml) and brine (60 ml). The organic layer was separated, and the aqueous layer was extracted with dichloromethane (2×50 ml). The combined organic extracts were dried over magnesium sulfate. The solvent was evaporated in vacuo to give the title compound as a light yellowish solid (15.92 g, 95%). ES-MS (M+H)+=214.

Example 4

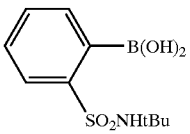

To a solution of the compound of example 3 (15.92 g, 74.7 mmol) in tetrahydrofuran (200 ml) in an ice bath was added 1.6M n-butyllithium in hexane (100 ml, 164 mmol) dropwise over 30 minutes. The mixture remained a clear solution. In an ice bath it was added triisopropylborate (24.1 ml, 104 mmol) dropwise. The mixture was stirred at room temperature for 3.5 hrs, solution becoming cloudy. After it was cooled in an ice bath, 1N hydrochloride (200 ml) was added. The mixture was stirred at room temperature overnight. It was extracted with ether (2×50 ml). The organic extract was washed with 1N sodium hydroxide (2×60 ml). The aqueous solution was acidified to pH=1 with 6N hydrochloride, and then extracted with ether (2×100 ml). The ether extract was dried over magnesium sulfate, and concentrated in vacuo. The crude product was recrystallized by ether and hexane to give the title compound as a while solid (11.5 g, 60%). ES-MS (M+H)+=258.

Example 5

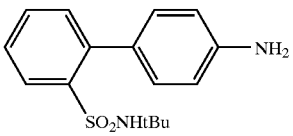

To a solution of the compound of example 4 (6.4 g, 25 mmol) in toluene (120 ml) was added water (15 ml), 5N sodium hydroxide (40 ml), isopropanol (60 ml), 4-bromoaniline (8.57 g, 50 mmol) and tetrakis(triphenylphosphine)palladium (0) (1.44 g, 1.25 mmol). The mixture was refluxed for 6 hrs, cooled to room temperature, and diluted with ethyl acetate. The organic layer was washed with water (50 ml), and dried over magnesium sulfate. After the evaporation of the solvent in vacuo, the crude reside was purified by silica gel chromatography using solvent system 30% ethyl acetate in hexane as eluent to give the title compound as a light yellowish solid (5 g, 66%). ES-MS (M+H)+=305.

Example 6

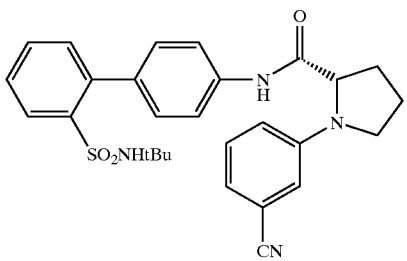

To a solution of the compound of example 2 (216 mg, 1 mmol) in dimethylformamide (5 ml) was added triethylamine (279 ul, 2 mmol), the compound of example 5 (304 mg, 1 mmol) and the coupling reagent BOP (531 mg, 1.2 mmol). The mixture was stirred at room temperature overnight. After the evaporation of the solvent in vacuo, the crude product was purified by silica gel column chromatography using solvent system 30–50% ethyl acetate in hexane as eluent to give the title compound as an oil (220 mg, 44%). ES-MS (M+H)+=503.

Example 7

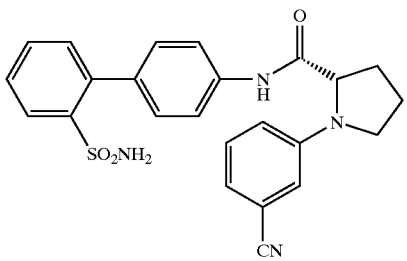

The compound of example 6 (220 mg, 0.44 mmol) was dissolved in trifluoroacetic acid (3 ml). The mixture was refluxed for 1.5 hrs. The solvent was evaporated in vacuo to give the title compound as an oil (200 mg, 100%). MS-ES (M+H)+=447.

Example 8

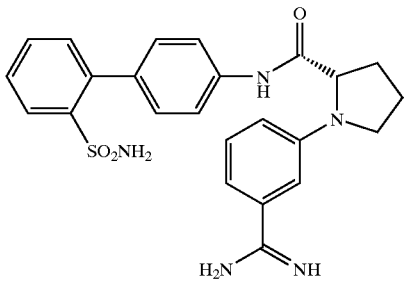

A solution of the compound of example 7 (200 mg, 0.44 mmol), hydroxylamine hydrochloride (76 mg, 1.1 mmol) and triethylamine (153 ul, 1.1 mmol) in absolute ethanol (3 ml) was stirred at 40° C. for 15 hrs. After the evaporation of the solvent in vacuo, the residue was dissolved in acetic acid (2 ml), and acetic anhydride (83 ul, 0.88mmol) was added. The mixture was stirred at room temperature for 3 hrs. It was diluted with absolute methanol (5 ml), and 10% Pd/C (catalytic amount) was added. The mixture was applied with 50 psi hydrogen for 6 hrs. After the filtration through Celite to remove the catalyst, the filtrate was concentrated in vacuo. The crude residue was purified by RP-HPLC to give the title compound as a white powder (89 mg, 46%). ES-MS (M+H)+=464.

Example 9

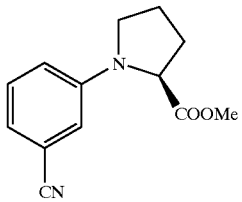

To a solution of the compound of example 2 (210 mg, 1 mmol) in methanol (5 ml) in an ice bath was added thionyl chloride (142 ul, 2 mmol) dropwise. The mixture was stirred at room temperature overnight. After the concentration in vacuo, it was dissolved in dichloromethane (10 ml), and washed with water (5 ml). The organic extract was dried over magnesium sulfate, and concentrated in vacuo to give the title compound as an oil (290 mg, 100%). ES-MS (M+H)+=231.

Example 10

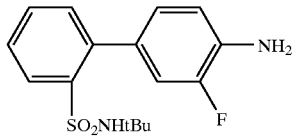

To a solution of the compound of example 4 (2.06 g, 8 mmol) in toluene (60 ml) was added water (4 ml), 8N sodium hydroxide (8 ml), isopropanol (16 ml), 2-fluoro-4-iodoaniline (3.8 g, 16 mmol) and tetrakis(triphenylphosphine)palladium (0) (464 mg, 0.4 mmol). The mixture was refluxed for 3–4 hrs, cooled to room temperature, and diluted with ethyl acetate. The organic layer was washed with water (25 ml), and dried over magnesium sulfate. After the evaporation of the solvent in vacuo, the crude reside was purified by silica gel column chromatography using solvent system 20–30% ethyl acetate in hexane as eluent to give the title compound as a white solid (1.49 g, 58%). ES-MS (M+H)+=323.

Example 11

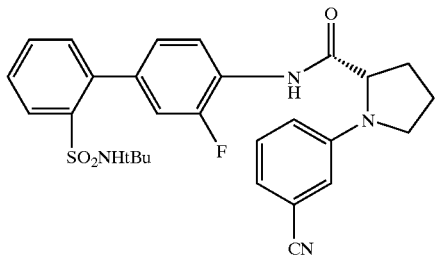

To a solution of the compound of example 10 (110 mg, 0.34 mmol) in dichloromethane (5 ml) was added 2.0M trimethylaluminum in hexane (0.51 ml, 1.02 mmol). The mixture was stirred at room temperature for 30 minutes, methane gas evolved. A solution of the compound of example 9 (78 mg, 0.34 mmol) in dichloromethane (1 ml) was added. The mixture was stirred at room temperature overnight. 1N hydrochloride was added to acidify the solution to pH=2. After the addition of water and dichloromethane, the organic layer was separated, and the aqueous layer was extracted with dichloromethane. The combined organic extracts were dried over magnesium sulfate, and concentrated in vacuo. The crude residue was purified by silica gel column chromatography using solvent system 25% ethyl acetate in hexane as eluent to give the title compound as a solid (90 mg, 51%). ES-MS (M+H)+=521.

Example 12

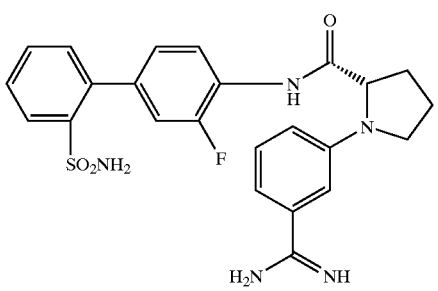

To a solution of the compound of example 11 (90 mg, 0.17 mmol) in absolute methanol (3 ml) in an ice bath was saturated with hydrochloride gas for 10 minutes. The mixture was stirred at room temperature for 3 hrs. After the evaporation of the solvent in vacuo, the residue was dissolved in absolute methanol (3 ml), and ammonia acetate (80 mg, 1.04 mmol) was added. The mixture was refluxed for 3 hrs. The solvent was evaporated in vacuo. The crude residue was purified by RP-HPLC to give the title compound as a white powder (36 mg, 44%). ES-MS (M+H)+=482.

Example 13

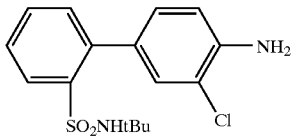

To a solution of the compound of example 4 (2.06 g, 8 mmol) in toluene (60 ml) was added water (4 ml), 8N sodium hydroxide (8 ml), isopropanol (16 ml), 2-chloro-4-iodoaniline (4.06 g, 16 mmol) and tetrakis(triphenylphosphine)palladium(0) (464 mg, 0.4 mmol). The mixture was refluxed for 3–4 hrs, cooled to room temperature, and diluted with ethyl acetate. The organic layer was washed with water (25 ml), and dried over magnesium sulfate. After the evaporation of the solvent in vacuo, the crude reside was purified by silica gel column chromatography using solvent system 20–30% ethyl acetate in hexane as eluent to give the title compound as a white solid (1.43 g, 53%). ES-MS (M+H)+=339.

Example 14

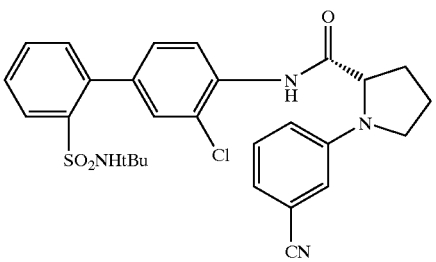

To a solution of the compound of example 13 (147 mg, 0.43 mmol) in dichloromethane (5 ml) was added 2.0M trimethylaluminum in hexane (0.65 ml, 1.30 mmol). The mixture was stirred at room temperature for 30 minutes, methane gas evolved. A solution of the compound of example 9 (100 mg, 0.43 mmol) in dichloromethane (1 ml) was added. The mixture was stirred at room temperature overnight. 1N hydrochloride was added to acidify the solution to pH=2. After the addition of water and dichloromethane, the organic layer was separated, and the aqueous layer was extracted with dichloromethane. The combined organic extracts were dried over magnesium sulfate, and concentrated in vacuo. The crude residue was purified by silica gel column chromatography using solvent system 25% ethyl acetate in hexane as eluent to give the title compound as a solid (180 mg, 78%). ES-MS (M+H)+=537.

Example 15

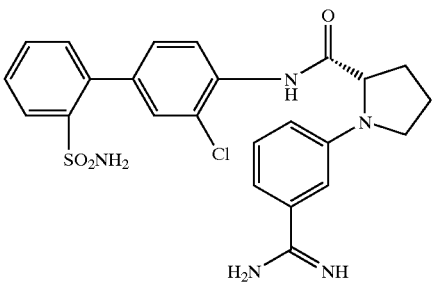

To a solution of the compound of example 14 (180 mg, 0.34 mmol) in absolute methanol (3 ml) in an ice bath was saturated with hydrochloride gas for 10 minutes. The mixture was stirred at room temperature for 3 hrs. After the evaporation of the solvent in vacuo, the residue was dissolved in absolute methanol (3 ml), and ammonia acetate (155 mg, 2 mmol) was added. The mixture was refluxed for 3 hrs. The solvent was evaporated in vacuo. The crude residue was purified by RP-HPLC to give the title compound as a white powder (55 mg, 33%). ES-MS (M+H)+=498.

Example 16

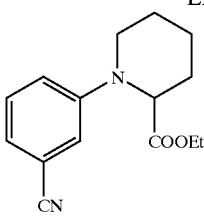

To a solution of 3-bromobenzonitrile (1.82 g, 10 mmol), ethyl pipecolinate (3.14 g, 20 mmol), sodium tert-butoxide (1.35 g, 14 mmol) and (s)-(−)2,2′-bis (diphenylphosphino)-1,1′-binaphthyl (125 mg, 0.2 mmol) in toluene (20 ml) was added tris(dibenzylideneacetone)dipalladium (0) (92 mg, 0.1 mmol). The mixture was stirred at 90° C. for 6 hrs. After the filtration of the solid, the filtrate was concentrated in vacuo. The residue was purified by silica gel column chromatography using solvent system 5–10% ethyl acetate in hexane as eluent to give the title compound as an oil (770 mg, 30%). ES-MS (M+H)+=259.

Example 17

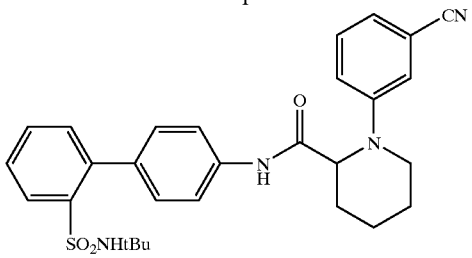

To a solution of the compound of example 5 (189 mg, 0.62 mmol) in dichloromethane (2 ml) was added 2.0M trimethylaluminum in hexane (0.93 ml, 1.86 mmol). The mixture was stirred at room temperature for 30 minutes, methane gas evolved. A solution of the compound of example 16 (160 mg, 0.62 mmol) in dichloromethane (1 ml) was added. The mixture was stirred at room temperature overnight. 1N hydrochloride was added to acidify the solution to pH=2. After the addition of water and dichloromethane, the organic layer was separated, and the aqueous layer was extracted with dichloromethane. The combined organic extracts were dried over magnesium sulfate, and concentrated in vacuo to give the title compound as a yellow solid (330 mg, 100%). ES-MS (M+H)+=517.

Example 18

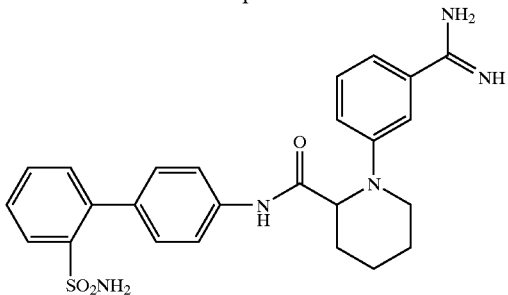

A solution of the compound of example 17 (330 mg, 0.64 mmol), hydroxylamine hydrochloride (110 mg, 1.6 mmol) and triethylamine (223 ul, 1.6 mmol) in absolute ethanol (10 ml) was stirred at 40° C. for 15 hrs. After the evaporation of the solvent in vacuo, the residue was dissolved in acetic acid (4 ml), and acetic anhydride (121 ul, 1.28 mmol) was added. The mixture was stirred at room temperature for 3 hrs. It was diluted with absolute methanol (7 ml), and 10% Pd/C (catalytic amount) was added. The mixture was applied with 50 psi hydrogen for 6 hrs. After the filtration through Celite to remove the catalyst, the filtrate was concentrated in vacuo. The residue was dissolved in trifluoroacetic acid (5 ml). The mixture was refluxed for 1.5 hrs. After the evaporation of the solvent in vacuo, the crude residue was purified by RP-HPLC to give the title compound as a white powder (200 mg, 62%). ES-MS (M+H)+=478.

Example 19

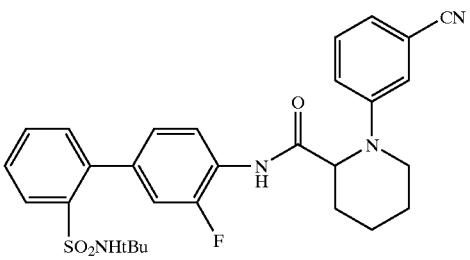

To a solution of the compound of example 10 (125 mg, 0.39 mmol) in dichloromethane (5 ml) was added 2.0M trimethylaluminum in hexane (0.58 ml, 1.16 mmol). The mixture was stirred at room temperature for 30 minutes, methane gas evolved. A solution of the compound of example 16 (100 mg, 0.39 mmol) in dichlodomethane (1 ml) was added. The mixture was stirred at room temperature overnight. 1N hydrochloride was added to acidify the solution to pH=2. After the addition of water and dichloromethane, the organic layer was separated and the aqueous layer was extracted with dichloromethane. The combined organic extracts were dried over magnesium sulfate, and concentrated in vacuo. The crude residue was purified by silica gel column chromatography using solvent system 20% ethyl acetate in hexane as eluent to give the title compound as a solid (150 mg, 72%). ES-MS (M+H)+=535.

Example 20

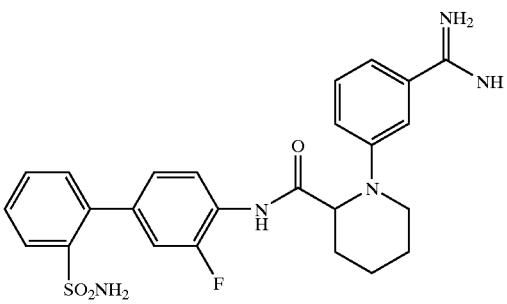

To a solution of the compound of example 19 (100 mg, 0.19 mmol) and triethylamine (1 ml) in absolute pyridine (10 ml) was saturated with hydrosulfide gas for 10 minutes. The mixture was stirred at room temperature for 15 hrs. After the evaporation of the solvent in vacuo, the green residue was dissolved in acetone (10 ml). Iodomethane (118 ul, 1.9 mmol) was added. The mixture was refluxed for 1 hr. After the evaporation of the solvent in vacuo, the residue was dissolved in absolute methanol (15 ml), and ammonia acetate (176 mg, 3.28 mmol) was added. The mixture was refluxed for 3 hrs. After the concentration in vacuo, the residue was dissolved in trifluoroacetic acid (5 ml), and was refluxed for 1 hr. The solvent was evaporated in vacuo. The crude residue was purified by RP-HPLC to give the title compound as a white powder. ES-MS (M+H)+=496.

Exmple 21

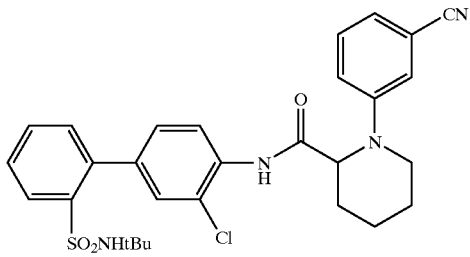

To a solution of the compound of example 13 (132 mg, 0.39 mmol) in dichloromethane (5 ml) was added 2.0M trimethylaluminum in hexane (0.58 ml, 1.17 mmol). The mixture was stirred at room temperature for 30 minutes, methane gas evolved. A solution of the compound of example 16 (100 mg, 0.39 mmol) in dichloromethane (1 ml) was added. The mixture was stirred at room temperature overnight. 1N hydrochloride solution was added to acidify the solution to pH=2. After the addition of water and dichloromethane, the organic layer was separated, and the aqueous layer was extracted with dichloromethane. The combined organic extracts were dried over magnesium sulfate, and concentrated in vacuo. The crude residue was purified by silica gel column chromatography using solvent system 20% ethyl acetate in hexane as eluent to give the title compound as an oil (160 mg, 75%). ES-MS (M+H)+=551.

Example 22

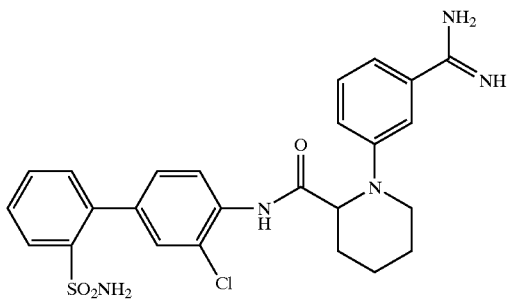

To a solution of the compound of example 21 (100 mg, 0.18 mmol) and triethylamine (1 ml) in absolute pyridine (10 ml) was saturated with hydrosulfide gas for 10 minutes. The mixture was stirred at room temperature for 15 hrs. After the evaporation of the solvent in vacuo, the green residue was dissolved in acetone (10 ml). Iodomethane (112 ul, 1.8 mmol) was added. The mixture was refluxed for 1 hr. After the evaporation of the solvent in vacuo, the residue was dissolved in absolute methanol (15 ml), and ammonia acetate (166 mg, 2.16 mmol) was added. The mixture was refluxed for 3 hrs. After the evaporation of the solvent in vacuo, the residue was dissolved in trifluoroacetic acid (5 ml), and was refluxed for 1 hr. The solvent was evaporated in vacuo. The crude residue was purified by RP-HPLC to give the title compound as a white powder. ES-MS (M+H)+=512.

Example 23

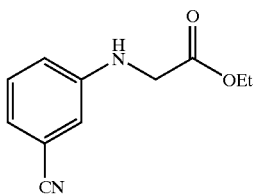

To a solution of ethyl bromoacetate (10.6 g, 60 mmol), 3-aminobenzonitrile (5 g, 40 mmol), and potassium carbonate (17.5 g, 120 mmol) in acetonitrile (30 ml) was added potassium iodide (1.4 g, 8 mmol). The mixture was heated to reflux for 6 hrs. The mixture was cooled to room temperature, and solvent was removed in vacuo. Ether and water were added to the mixture. Organic layer was washed with 1N hydrochloride and brine, and dried over magnesium sulfate. After the concentration in vacuo, the crude residue was purified by silica gel column chromatography using solvent system 15% ethyl acetate in hexane as eluent to give the title compound as light yellowish solid (7.94 g, 97%). ES-MS (M+H)+=205.

Example 24

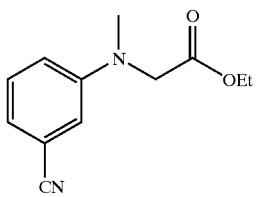

To a solution of the compound of example 23 (200 mg, 1 mmol) and cesium carbonate (650 mg, 2 mmol) in dimethylformamide (5 ml) was added iodomethane (75 ul, 1.2 mmol). The mixture was stirred at 90° C. for 2 hrs. After the filtration of the solid, the filtrate was concentrated in vacuo, and the residue was purified by silica gel column chromatography using solvent system 15% ethyl acetate in hexane as eluent to give the title compound as an oil (270 mg, 100%). ES-MS (M+H)+=219.

Example 25

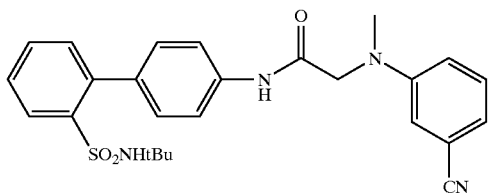

To a solution of the compound of example 5 (126 mg, 0.41 mmol) in dichloromethane (5 ml) was added 20M trimethylaluminum in hexane (0.62 ml, 1.24 mmol). The mixture was stirred at room temperature for 30 minutes, methane gas evolved. A solution of the compound of example 24 (90 mg, 0.41 mmol) in dichlodomethane (1 ml) was added. The mixture was stirred at room temperature overnight. 1N hydrochloride was added to acidify the solution to pH=2. After the addition of water and dichloromethane, the organic layer was separated and the aqueous layer was extracted with dichloromethane. The combined organic extracts were dried over magnesium sulfate, and concentrated in vacuo. The crude residue was purified by silica gel column chromatography using solvent system 30% ethyl acetate in hexane as eluent to give the title compound as a solid (70 mg, 36%). ES-MS (M+H)+=477.

Example 26

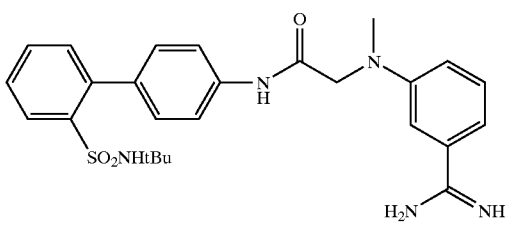

A solution of the compound of example 25 (70 mg, 0.15 mmol), hydroxylamine hydrochloride (26 mg, 0.37 mmol) and triethylamine (52 ul, 0.37 mmol) in absolute ethanol (3 ml) was stirred at 40° C. for 15 hrs. After the evaporation of the solvent in vacuo, the residue was dissolved in acetic acid (3 ml), and acetic anhydride (28 ul, 0.3 mmol) was added. The mixture was stirred at room temperature for 3 hrs. It was diluted with absolute methanol (5 ml), and 10% Pd/C (catalytic amount) was added. The mixture was applied with 50 psi hydrogen for 6 hrs. After the filtration through Celite to remove the catalyst, the filtrate was concentrated in vacuo. The crude residue was purified by RP-HPLC to give the title compound as a white powder. ES-MS (M+H)+=494.

Example 27

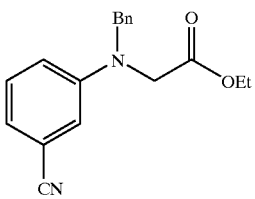

To a solution of the compound of example 23 (200 mg, 1 mmol) and cesium carbonate (650 mg, 2 mmol) in dimethylformamide (5 ml) was added benzyl bromide (180 ul, 1.5 mmol). The mixture was stirred at 90° C. for 2 hrs. After the filtration of the solid, the filtrate was concentrated in vacuo and the residue was purified by silica gel column chromatography using solvent system 10% ethyl acetate in hexane as eluent to give the title compound as an oil (210 mg, 71%). ES-MS (M+H)+=295.

Example 28

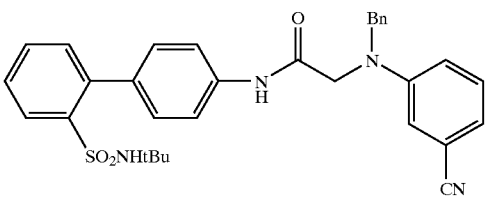

To a solution of the compound of example 5 (126 mg, 0.41 mmol) in dichloromethane (5 ml) was added 2.0 M trimethylaluminum in hexane (0.62 ml, 1.24 mmol). The mixture was stirred at room temperature for 30 minutes, methane gas evolved. A solution of the compound of example 27 (120 mg, 0.41 mmol) in dichlodomethane (1 ml) was added. The mixture was stirred at room temperature overnight. 1N hydrochloride was added to acidify the solution to pH=2. After the addition of water and dichloromethane, the organic layer was separated, and the aqueous layer was extracted with dichloromethane. The combined organic extracts were dried over magnesium sulfate, and concentrated in vacuo. The crude residue was purified by silica gel column chromatography using solvent system 20% ethyl acetate in hexane as eluent to give the title compound as a solid (172 mg, 76%). ES-MS (M+H)+=553.

Example 29

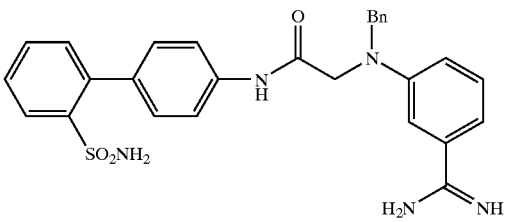

To a solution of the compound of example 28 (100 mg, 0.18 mmol) and absolute methanol (73 ul, 1.8 mmol) in ethyl acetate (3 ml) in an ice bath was saturated with hydrochloride gas for 10 minutes. The mixture was stirred at room temperature for 3 hrs. After the evaporation of the solvent in vacuo, the residue was dissolved in absolute methanol (3 ml), and ammonia acetate (83 mg, 1.08 mmol) was added. The mixture was refluxed for 3 hrs. The solvent was evaporated in vacuo. The crude residue was purified by RP-HPLC to give the title compound as white powder. ES-MS (M+H)+514.

Example 30

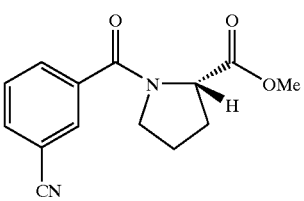

H-Pro-OMe (3.38 g, 20.4 mmol) and 3-cyano-benzoic acid (3 g, 20.4 mmol) were dissolved in DMF (100 mL).

DIEA (7.28 mL, 40.8 mmol) was added followed by the addition of the coupling reagent BOP (9.03 g, 20.4 mmol). The solution was stirred at room temperature for 12 hours. The reaction mixture was diluted in a mixture of EtOAc/H$_2$O (100 mL:40 mL). The organic layer was washed with water, sat. NaHCO$_3$, water, brine, dried over MgSO$_4$, filtered and solvent evaporated. The residue was purified by silica gel column chromatography using solvent system 20% hexane in EtOAc as eluant to give the title compound. ES-MS (M+H)+=259.0.

Example 31

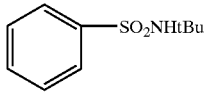

To a solution of tert-Butylamine (41.4 g, 566 mmol) and triethylamine (118 mL, 849 mmol) in DCM (1000 mL) in an ice bath, was added benzenesulfonyl chloride (100 g, 566 mmol) dropwise. The mixture was stirred at room temperature overnight. Water was added to the mixture and organic layer was washed with water, brine, dried over Na$_2$SO$_4$, filtered and filtrated evaporated in vacuo to give the title compound as light yellowish solid (117.63 g, 97.6%). (M+H)+=214.1.

Example 32

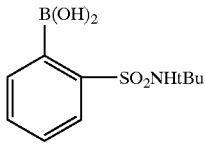

To a solution of compound of example 31 (53.25 g, 250 mmol) in THF (600 mL) in an ice bath, was added n-butyllithium in hexane (200 mL, 500 mmol) dropwise. A thick precipitate was formed when the reaction mixture was warmed up to 10° C. Triisopropylborate was added keeping the temperature below 35° C. After 1 hr., the mixture was cooled in an ice bath, 1N HCl (405 mL) was added, and the mixture was stirred overnight. The mixture was extracted with ether (100 mL) three times. The combined organic extracts were extracted with 1N NaOH (130 mL) three times. The aqueous extracts were acidified to pH 1 with 12 N HCl, and then extracted with ether three times (140 ML). The combined ether extracts were dried over MgSO$_4$, and solvents evaporated in vacuo. Hexane and ether were added and a white precipitate formed. The solid was collected and washed with 10% ether/hexane to give the title compound. (M+H)+=257.1.

Example 33

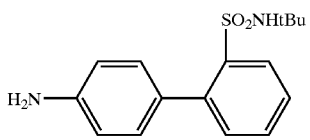

To a solution of compound of example 32 (6.4 g, 25 mmol) in toluene (120 mL) was added water (15 mL), 5N NaOH solution (38.5 mL), isopropanol (60 mL), 4-bromoaniline and tetrakis(triphenylphosphine)palladium (0). The mixture was refluxed for six hours, cooled to room temperature, diluted with EtOAc. The organic layer was washed with water, dried with MgSO$_4$, filtered and concentrated. This was purified by silica gel column chromatography using solvent system 30% EtOAc in hexane as eluant to give the title compound (5 g, 66%). ES-MS (M+H)+=305.1.

Example 34

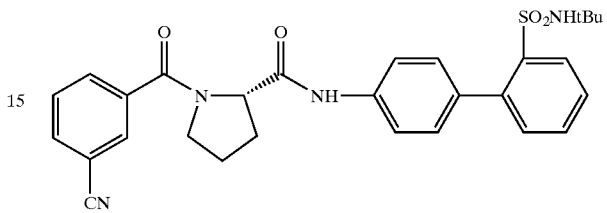

To a solution of compound of example 33 (278 mg, 0.92 mmol) in DCM (5 mL) was added trimethylaluminum (1.37 mL, 2 M in hexane) dropwise. The reaction mixture was stirred at room temperature for 30 min. Compound of example 17 (236 mg, 0.92 mmol) in DCM (3 mL) was added dropwise. The mixture was stirred at room temperature overnight. 2N HCl was added to PH 2 to neutralize excess AlMe$_3$. Water and DCM were added. The organic layer was dried over MgSO$_4$ and concentrated in vacuo. The obtained resudue was purified by silica gel column chromatography using solvent system 50% EtOAc in hexane as eluant to give the title compound. ES-MS (M+Na)+=553.2.

Example 35

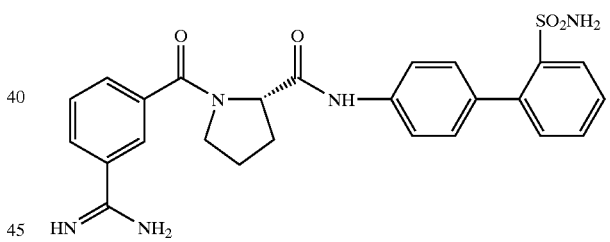

A solution of the compound of example 34(96 mg, 0.18 mmol) in MeOH (3 mL) was treated with a stream of HCl gas for 10 min. at 0° C. The resulting solution was capped, stirred at room temperature overnight and evaporated in vacuo. The residue was reconstituted in MeOH (3 mL) and the mixture was treated with NH$_4$OAc (69 mg, 0.9 mmol). The reaction mixture was refluxed for 1.5 hrs. and concentrated in vacuo. The obtained residue was purified by RP-HPLC to give the title compound as a white powder. ES-MS (M+H)+=492.0

BIOLOGICAL ACTIVITY EXAMPLES

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 μM. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving 50% inhibition of the substrate turnover. The compounds of the present invention desirably have an $IC_{50}$ of less than 500 nM in the factor Xa assay, preferably less than 200 nM, and more preferred compounds have an $IC_{50}$ of about 100 nM or less in the factor Xa assay. The compounds of the present invention desirably have an $IC_{50}$ of less than 4.0 $\mu$M in the prothrombinase assay, preferably less than 200 nM, and more preferred compounds have an $IC_{50}$ of about 10 nM or less in the prothrombinase assay. The compounds of the present Invention desirably have an $IC_{50}$ of greater than 1.0 $\mu$M in the thrombin assay, preferably greater than 10.0 $\mu$M, and more preferred compounds have an $IC_{50}$ of greater than 100.0 $\mu$M in the thrombin assay.

Amidolytic Assays for Determining Protease Inhibition Activity

The factor Xa and thrombin assays are performed at room temperature, in 0.02 M Tris•HCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 75, 427–436 (1994). Specifically, the activity of the prothrombinase complex is determined by measuring the time course of thrombin generation using the p-nitroanilide substrate Chromozym TH. The assay consists of preincubation (5 minutes) of selected compounds to be tested as inhibitors with the complex formed from factor Xa (0.5 nM), factor Va (2 nM), phosphatidyl serine:phosphatidyl choline (25:75, 20 $\mu$M) in 20 mM Tris•HCl buffer, pH 7.5, containing 0.15 M NaCl, 5 mM $CaCl_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis Model

Administration of compounds in the rabbit venous thrombosis model demonstrates antithrombotic efficacy at the higher doses evaluated. There are no significant effects of the compound on the aPTT and PT prolongation with the highest dose (100 $\mu$g/kg+2.57 $\mu$g/kg/min). Compounds have no significant effects on hematological parameters as compared to saline controls. All measurements are an average of all samples after steady state administration of vehicle or (D)-Arg-Gly-Arg-thiazole. Values are expressed as mean±SD.

Without fturther description, it is believed that one of ordinary skill in the art can, using the preceding description and the following illustrative examples, make and utilize the compounds of the present invention and practice the claimed methods.

What is claimed is:

1. A compound according to the formula I:

A-Y-D-E-G-J-Z-L wherein:
A is phenyl, which is independently substituted with 0–2 $R^1$ substituents;
$R^1$ is selected from:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalky, —CN, —$NO_2$, $(CH_2)_m NR^2R^3$, $SO_2NR^2R^3$, $SO_2R^2$, $CF_3$, $OR^2$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;
$R^2$ and $R^3$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;
m is an integer of 0–2;
Y is a direct link,
D is a phenyl, which is independently substituted with 0–2 $R^{1a}$ substituents;
$R^{1a}$ is selected from:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, (CH$_2$)$_m$NR$^{2a}$R$^{3a}$, SO$_2$NR$^{2a}$R$^{3a}$, SO$_2$R$^{2a}$, CF$_3$, OR$^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

R$^{2a}$ and R$^{3a}$ are independently selected from the group consisting of:

H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

E is a member selected from the group consisting of:
—N(R$^5$)—C(=O)—, —C(=O)—N(R$^5$)—, —N(R$^5$)—C(=O)—N(R$^6$)—, —SO$_2$—N(R$^5$)—, —N(R$^5$)—SO$_2$—N(R$^6$)— and —N(R$^5$)—SO$_2$—N(R$^6$)—C(=O)—;

R$^5$ and R$^6$ are independently selected from:

H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl, C$_{0-4}$alkylnaphthyl, C$_{0-4}$alkylheteroaryl, C$_{1-4}$alkylCOOH and C$_{1-4}$alkylCOOC$_{1-4}$alkyl, wherein from 1–4 hydrogen atoms on the ring atoms of the phenyl, naphthyl and heteroaryl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

G is a member selected from the group consisting of from: a direct link, —C(R$^7$,R$^8$)— and —C(R$^{7a}$,R$^{8a}$)C(R$^{7b}$,R$^{8b}$)— wherein R$^7$, R$^8$, R$^{7a}$, R$^{8a}$, R$^{7b}$ and R$^{8b}$ are independently a member selected from the group consisting of:

hydrogen, C$_{1-4}$alkyl, C$_{2-6}$alkenyl, C$_{2-6}$alkynyl, C$_{3-8}$cycloalkyl, C$_{0-4}$alkyl-C$_{3-8}$cycloalkyl, C$_{0-4}$alkylphenyl, C$_{0-4}$alkylnaphthyl, —OR$^9$, —C$_{0-4}$alkylCOOR$^9$, —C$_{0-4}$alkylC(=O)NR$^9$R$^{10}$, —C$_{0-4}$alkylC(=O)NR$^9$—CH$_2$—CH$_2$O—R$^{10}$, —C$_{0-4}$alkylC(=O)NR$^9$(—CH$_2$—CH$_2$—O—R$^{10}$—)$_2$, —N(R$^9$)COR$^{10}$, —N(R$^9$)C(=O)R$^{10}$, —N(R$^9$)SO$_2$R$^{10}$, and a naturally occurring or synthetic amino acid side chain, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkyl-C$_{3-8}$cycloalkyl, —CN and —NO$_2$;

R$^9$ and R$^{10}$ are independently selected from:

H, C$_{1-4}$alkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkyl-C$_{3-8}$cycloalkyl, —CN and —NO$_2$, and wherein R$^9$ and R$^{10}$ taken together can form a 5–8 membered heterocylic ring;

J is

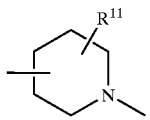

wherein the ring carbons may be independently substituted by a total of 0 to 4 R$^{11}$ groups;

R$^{11}$ is a member selected from the group consisting of:

hydrogen, —OH, —O—C$_{1-4}$alkyl, —C$_{1-4}$alkyl, C$_{2-6}$alkenyl, C$_{2-6}$alkynyl, C$_{3-8}$cycloalkyl, C$_{0-4}$alkyl-C$_{3-8}$cycloalkyl, C$_{0-4}$alkylphenyl, C$_{0-4}$alkylnaphthyl, C$_{0-4}$alkylheterocyclic ring having from 1 to 4 hetero ring atoms selected from the group consisting of N, O and S, CH$_2$COOC$_{1-4}$alkyl, CH$_2$COOC$_{1-4}$alkylphenyl and CH$_2$COOC$_{1-4}$alkylnaphthyl;

Z is a phenyl, which is independently substituted with 0–2 R$^{1b}$ substituents;

R$^{1b}$ is selected from:

Halo, C$_{1-4}$alkyl, C$_{2-6}$alkenyl, C$_{2-6}$alkynyl, C$_{3-8}$cycloalkyl, C$_{0-4}$alkylC$_{3-8}$cyclcloalkyl, —CN, —NO$_2$, NR$^{2b}$R$^{3b}$, SO$_2$NR$^{2b}$R$^{3b}$, SO$_2$R$^{2b}$, CF$_3$, OR$^{2b}$, O—CH$_2$—CH$_2$—OR$^{2b}$, O—CH$_2$—COOR$^{2b}$, N(R$^{2b}$)—CH$_2$—CH$_2$—OR$^{2b}$, N(—CH$_2$—CH$_2$—OR$^{2b}$)$_2$, N(R$^{2b}$)—C(=O)R$^{3b}$, N(R$^{2b}$)—SO$_2$—R$^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

R$^{2b}$ and R$^{3b}$ are independently selected from the group consisting of:

H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

L is C(=NR$^{12}$)NR$^{12}$R$^{13}$;

R$^{12}$ and R$^{13}$ are independently selected from:

hydrogen, —OR$^{14}$, —NR$^{14}$R$^{15}$, C$_{1-4}$alkyl, C$_{0-4}$alkylphenyl, C$_{0-4}$alkylnaphthyl, COOC$_{1-4}$alkyl, COO-C$_{0-4}$alkylphenyl and COO-C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN, and —NO$_2$;

R$^{14}$ and R$^{15}$ are independently selected from:

H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN, and —NO$_2$;

all and prodrug derivatives.

2. A compound of claim 1 wherein

A is phenyl, which is independently substituted with 0–2 $R^1$ substituents;

$R^1$ is selected from:
Halo, $C_{1-4}$alkyl, —CN, $(CH_2)_m NR^2R^3$, $SO_2NR^2R^3$, $SO_2R^2$, $CF_3$, $OR^2$, and a 5–6 membered aromatic heterocyclic system containing from 1–4 heteroatoms selected from N, O and S;

$R^2$ and $R^3$ are independently selected from the group consisting of:
H, $C_{1-4}$alkyl, $C_{0-4}$alkylaryl;

m is an integer of 0–2;

Y is a direct link,

D is a phenyl which is independently substituted with 0–2 $R^{1a}$ substituents;

$R^{1a}$ is selected from:
Halo, $C_{1-4}$alkyl, —CN, —$NO_2$, $(CH_2)_m NR^{2a}R^{3a}$, $SO_2NR^{2a}R^{3a}$, $SO_2R^{2a}$, $CF_3$, $OR^{2a}$, and a 5–6 membered aromatic heterocyclic system containing from 1–4 heteroatoms selected from N, O and S;

$R^{2a}$ and $R^{3a}$ are independently selected from the group consisting of:
H, $C_{1-4}$alkyl, $C_{0-4}$alkylaryl;

E is a member selected from the group consisting of:
—N($R^5$)—C(=O)—, —C(=O)—N($R^5$)—, —N($R^5$)—C(=O)—N($R^6$)—, —$SO_2$—N($R^5$)—, —N($R^5$)—$SO_2$—N($R^6$)— and —N($R^5$)—$SO_2$—N($R^6$)—C(=O)—;

$R^5$ and $R^6$ are independently selected from:
H, $C_{1-4}$alkyl, $C_{0-4}$alkylaryl, $C_{0-4}$alkylheteroaryl, $C_{1-4}$alkylCOOH and $C_{1-4}$alkylCOOC$_{1-4}$alkyl;

G is a member selected from the group consisting of:
a direct link, —$CR^7R^8$— and —$CR^{7a}R^{8a}$—$CR^{7b}R^{8b}$— wherein $R^7$, $R^8$, $R^{7a}$, $R^{8a}$, $R^{7b}$ and $R^{8b}$ are independently a member selected from the group consisting of:
hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —$OR^9$, —$C_{0-4}$alkylCOOR$^9$, —$C_{0-4}$alkylC(=O)NR$^9R^{10}$, —$C_{0-4}$alkylC(=O)NR$^9$—$CH_2$—$CH_2$—O—$R^{10}$, —$C_{0-4}$alkylC(=O)NR$^9$(—$CH_2$—$CH_2$—O—$R^{10}$—)$_2$, —N($R^9$)COR$^{10}$, —N($R^9$)C(=O)R$^{10}$, —N($R^9$)SO$_2R^{10}$, and common amino acid side chains;

$R^9$ and $R^{10}$ are independently selected from:
H, $C_{1-4}$alkyl, $C_{0-4}$alkylphenyl and $C_{0-4}$alkylaryl;

J is

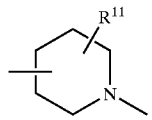

wherein the ring carbons may be independently substituted by a total of 0 to 4 $R^{11}$ groups;

$R^{11}$ is a member selected from the group consisting of:
hydrogen, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, $CH_2COOC_{1-4}$alkyl, $CH_2COOC_{1-4}$alkylphenyl and $CH_2COOC_{1-4}$alkylnaphthyl;

Z is a phenyl, which is independently substituted with 0–2 $R^{1b}$ substituents;

$R^{1b}$ is selected from:
Halo, $C_{1-4}$alkyl, —CN, —$NO_2$, $NR^{2b}R^{3b}$, $SO_2NR^{2b}R^{3b}$, $SO_2R^{2b}$, $CF_3$, $OR^{2b}$, O—$CH_2$—$CH_2$—$OR^{2b}$, O—$CH_2COOR^{2b}$, N($R^{2b}$)—$CH_2$—$CH_2$—$OR^{2b}$, N(—$CH_2$—$CH_2$—$OR^{2b}$)$_2$, N($R^{2b}$)—C(=O)$R^{3b}$, N($R^{2b}$)—$SO_2$—$R^{3b}$, and a 5–6 membered aromatic heterocyclic system containing from 1–4 heteroatoms selected from N, O and S;

$R^{2b}$ and $R^{3b}$ are independently selected from the group consisting of:
H, $C_{1-4}$alkyl, $C_{0-4}$alkylaryl;

L is C(=$NR^{12}$)$NR^{12}R^{13}$, $R^{12}$ and $R^{13}$ are independently selected from:
hydrogen, —$OR^{14}$, —$NR^{14}R^{15}$, $C_{1-4}$alkyl, $C_{0-4}$alkylaryl COO $C_{1-4}$alkyl, COO—$C_{0-4}$alkylaryl; and $R^{14}$ and $R^{15}$ are independently selected from:
H and $C_{1-4}$alkyl.

3. A compound of claim 1, wherein:

A is phenyl, which is independently substituted with 0–2 $R^1$ substituents;

$R^1$ is selected from:
halo, $(CH_2)_m NR^2R^3$, $SO_2NR^2R^3$ and $SO_2R^2$;

$R^2$ and $R^3$ are independently selected from the group consisting of:
H and $C_{1-4}$alkyl;

Y is a direct link,

D is a phenyl which is independently substituted with 0–2 $R^{1a}$ substituents;

$R^{1a}$ is selected from:
Halo and $C_{1-4}$alkyl;

E is a member selected from the group consisting of:
—N($R^5$)—C(=O)— and —C(=O)—N($R^5$)—;

$R^5$ is independently selected from:
H, $C_{1-4}$alkyl, $C_{0-4}$alkylaryl and $C_{0-4}$alkylheteroaryl;

G is a member selected from the group consisting of:
a direct link, —$CR^7R^8$— and —$CR^{7a}R^{8a}$—$CR^{7a}R^{8b}$— wherein $R^7$, $R^8$, $R^{7a}$, $R^{8a}$, $R^{7b}$ and $R^{8b}$ are independently a member selected from the group consisting of:
hydrogen, $C_{1-4}$alkyl, $C_{0-4}$alkyl-$C_{3-8}$cycloalkyl, $C_{0-4}$alkylaryl, —$OR^9$, —$C_{0-4}$alkylCOOR$^9$, —$C_{0-4}$alkylC(=O) NR$^9R^{10}$, —$C_{0-4}$alkylC(=O)NR$^9$—$CH_2$—$CH_2$—O—$R^{10}$, —$C_{0-4}$alkylC(=O)NR$^9$(—$CH_2$—$CH_2$—O—$R^{10}$—)$_2$, —N($R^9$)COR$^{10}$, —N($R^9$)C(=O)$R^{10}$, —N($R^9$)SO$_2R^{10}$, and common amino acid side chains;

$R^9$ and $R^{10}$ are independently selected from:
H and $C_{1-4}$alkyl, wherein the $NR^9R^{10}$ group of $R^7$, $R^8$, $R^{7a}$, $R^{8a}$, $R^{7b}$ and $R^{8b}$ is optionally cyclized to form a 5–8 membered heterocyclic group;

J is

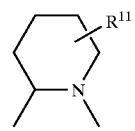

wherein the ring carbons may be substituted by a total of 0 to 2 $R^{11}$ groups;

$R^{11}$ is a member selected from the group consisting of:
hydrogen, —OH, —O—$C_{1-4}$alkyl, —$C_{1-4}$alkyl, $C_{2-6}$alkenyl, $C_{0-4}$alkylaryl, and a $C_{0-4}$alkylheterocyclic ring having from 1 to 4 hetero ring atoms selected from the group consisting of N, O and S;

Z is a phenyl, which is independently substituted with 0–2 $R^{1b}$ substituents;

$R^{1b}$ is selected from:
halo, $C_{1-4}$alkyl, OH, OBn, O—$CH_2$—$CH_2$—OH, O—$CH_2$—$CH_2$—$OCH_3$, O—$CH_2$—COOH, O—$CH_2$—C(=O)—O—$CH_3$, $NH_2$, NH—$CH_2$—$CH_2$—O—$CH_3$, NH—C(=O)—O—$CH_3$, and NH—$SO_2$—$CH_3$;

L is C(=$NR^{12}$)$NR^{12}R^{13}$; and $R^{12}$ and $R^{13}$ are independently selected from:
hydrogen and $C_{1-4}$alkyl.

4. A compound of claim 1, wherein:

A is a member selected from the group consisting of:

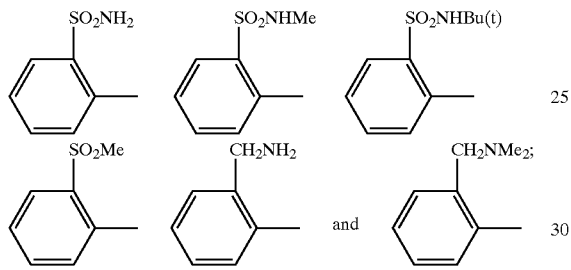

D is a member selected from the group consisting of:

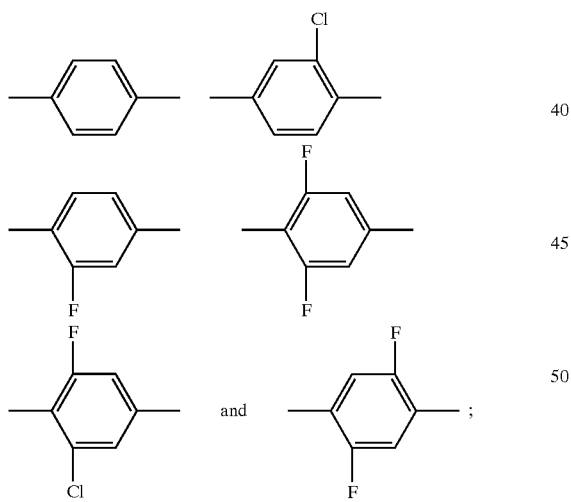

E is a member selected from the group consisting of:
—C(=O)—NH—, —C(=O)—N(—$CH_3$)—, C(=O)—N(—Bn)—, —NH—C(=O)—, —N(—$CH_3$)—C(=O)— and —N(—Bn)C(=O)—;

G is a member selected from the group consisting of:
a direct link, —CH—(—$NH_2$)—$CH_2$—, —CH—(—NH(C(=O)—$CH_3$))—$CH_2$—, —CH—(—NH(C(=O)—Ph))—$CH_2$—, —CH—(C(=O)—$OR^8$)—, —CH(—$R^7$)—, —$CH_2$—CH(C(=O)—$OR^8$)—, and —$CH_2$—CH(C(=O)—N(—$R^8$, —$R^8$))—;

$R^7$ is a member selected from the group consisting of:
H, phenyl, Bn, —O-loweralkyl and cyclohexyl;

$R^8$ is a member selected from the group consisting of:
H, $C_{1-6}$alkyl, —O-loweralkyl and $C_{3-6}$cycloalkyl;

J is

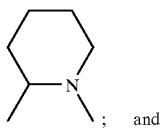

Z and L taken together are a member selected from the group consisting of:

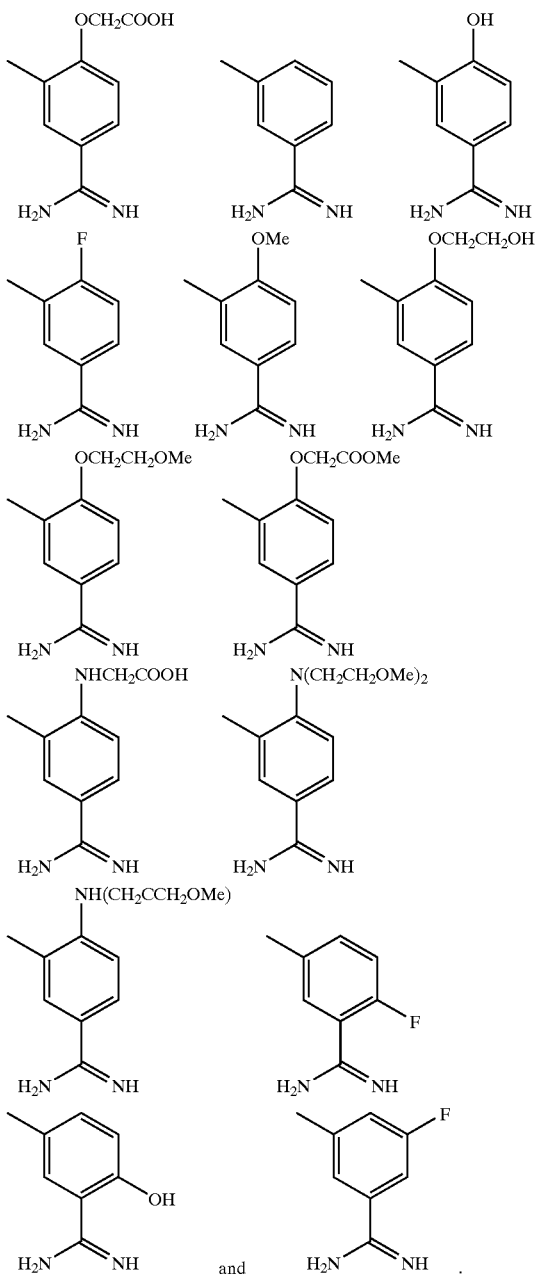

5. A pharmaceutical composition for preventing or treating a condition in a mammal characterized by undesired thrombosis comprising a pharmaceutically acceptable carrier and a compound of claim 1.

6. A pharmaceutical composition for preventing or treating a condition in a mammal characterized by undesired thrombosis comprising a pharmaceutically acceptable carrier and a compound of claim 2.

7. A pharmaceutical composition for preventing or treating a condition in a mammal characterized by undesired thrombosis comprising a pharmaceutically acceptable carrier and a compound of claim 3.

8. A pharmaceutical composition for preventing or treating a condition in a mammal characterized by undesired thrombosis comprising a pharmaceutically acceptable carrier and a compound of claim 4.

9. A method for preventing or treating a condition in a mammal characterized by undesired thrombosis comprising the step of administering to said mammal a therapeutically effective amount of a compound of claim 1.

10. The method of claim 9, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

11. A method for preventing or treating a condition in a mammal characterized by undesired thrombosis comprising the step of administering to said mammal a therapeutically effective amount of a compound of claim 2.

12. The method of claim 11, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

13. A method for preventing or treating a condition in a mammal characterized by undesired thrombosis comprising the step of administering to said mammal a therapeutically effective amount of a compound of claim 3.

14. The method of claim 13, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

15. A method for preventing or treating a condition in a mammal characterized by undesired thrombosis comprising the step of administering to said mammal a therapeutically effective amount of a compound of claim 4.

16. The method of claim 15, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

17. A method for inhibiting the coagulation of biological samples, comprising the administration of a compound of claim 1.

18. A method for inhibiting the coagulation of biological samples, comprising the administration of a compound of claim 2.

19. A method for inhibiting the coagulation of biological samples, comprising the administration of a compound of claim 3.

20. A method for inhibiting the coagulation of biological samples, comprising the administration of a compound of claim 4.

\* \* \* \* \*

UNITED STATES PATENT AND TRADEMARK OFFICE
CERTIFICATE OF CORRECTION

PATENT NO. : 6,673,817 B1
DATED : January 6, 2004
INVENTOR(S) : Zhu et al.

It is certified that error appears in the above-identified patent and that said Letters Patent is hereby corrected as shown below:

Column 215,
Line 48, replace "—$CH_2O$—" with -- —$CH_2$—O— --.

Column 216,
Line 67, replace "all and prodrug derivatives" with -- or pharmaceutically acceptable salts thereof --.

Signed and Sealed this

Twenty-first Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,673,817 B1
DATED : January 6, 2004
INVENTOR(S) : Bing-Yan Zhu and Robert M. Scarborough It is certified that error appears in the above-identified patent and that said Letters Patent is hereby corrected as shown below:

<u>Title page,</u>
Item [22], should read as follows:
-- Filed: May 24, 2000 --.

Signed and Sealed this

Twenty-ninth Day of November, 2005

JON W. DUDAS
*Director of the United States Patent and Trademark Office*